United States Patent
Sasaki et al.

(10) Patent No.: US 9,188,885 B2
(45) Date of Patent: *Nov. 17, 2015

(54) REACTIVE COMPOUND, CHARGE TRANSPORTING FILM, PHOTOELECTRIC CONVERSION DEVICE, ELECTROPHOTOGRAPHIC PHOTORECEPTOR AND METHOD OF PRODUCING THE SAME, PROCESS CARTRIDGE, AND IMAGE FORMING APPARATUS

(71) Applicant: FUJI XEROX CO., LTD., Tokyo (JP)

(72) Inventors: Tomoya Sasaki, Kanagawa (JP); Katsumi Nukada, Kanagawa (JP); Wataru Yamada, Kanagawa (JP); Takatsugu Doi, Kanagawa (JP); Yuko Iwadate, Kanagawa (JP); Kenji Kajiwara, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 77 days.

This patent is subject to a terminal disclaimer.

(21) Appl. No.: 14/086,459

(22) Filed: Nov. 21, 2013

(65) Prior Publication Data

US 2014/0079435 A1    Mar. 20, 2014

Related U.S. Application Data

(62) Division of application No. 13/430,242, filed on Mar. 26, 2012, now Pat. No. 8,669,029.

(30) Foreign Application Priority Data

Aug. 22, 2011 (JP) .................................. 2011-181009
Aug. 22, 2011 (JP) .................................. 2011-181011

(51) Int. Cl.
*G03G 5/06* (2006.01)
*C07C 211/54* (2006.01)
(Continued)

(52) U.S. Cl.
CPC ............ *G03G 5/0618* (2013.01); *C07C 211/54* (2013.01); *C07C 219/32* (2013.01);
(Continued)

(58) Field of Classification Search
CPC ... G03G 5/0618; G03G 15/75; G03G 5/0614; G03G 5/071
USPC ........................................................ 430/58.75
See application file for complete search history.

(56) References Cited

U.S. PATENT DOCUMENTS 8,669,029 B2 * 3/2014 Sasaki et al. .................. 430/58.7
8,808,952 B2 * 8/2014 Iwadate et al. ............... 430/58.7
(Continued)

FOREIGN PATENT DOCUMENTS

JP     H01-172835 A     7/1989
JP     H01-172836 A     7/1989
(Continued)

OTHER PUBLICATIONS

Feb. 25, 2014 Office Action issued in U.S. Appl. No. 13/398,061.
(Continued)

*Primary Examiner* — Stewart Fraser
(74) *Attorney, Agent, or Firm* — Oliff PLC

(57) ABSTRACT

Provided is a reactive compound represented by the following General Formula (I):

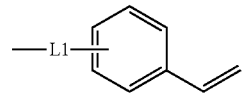

wherein in General Formula (I), F represents a charge transporting skeleton, D represents a group represented by the following General Formula (III), and m represents an integer of from 1 to 8:

(III)

wherein in General Formula (III), L1 represents a divalent linking group including one or more —C(=O)—O— groups.

9 Claims, 17 Drawing Sheets

(51) Int. Cl.
- *C07C 219/32* (2006.01)
- *C07C 229/42* (2006.01)
- *C07C 229/60* (2006.01)
- *C07C 237/20* (2006.01)
- *C07C 251/86* (2006.01)
- *H01L 51/00* (2006.01)
- *G03G 15/00* (2006.01)
- *G03G 5/07* (2006.01)
- *H01L 51/50* (2006.01)

(52) U.S. Cl.
CPC .......... *C07C229/42* (2013.01); *C07C 229/60* (2013.01); *C07C 237/20* (2013.01); *C07C 251/86* (2013.01); *G03G 5/0614* (2013.01); *G03G 5/071* (2013.01); *G03G 15/75* (2013.01); *H01L 51/0059* (2013.01); *C07C 2101/14* (2013.01); *C07C 2103/18* (2013.01); *H01L 51/5056* (2013.01)

(56) References Cited

U.S. PATENT DOCUMENTS

| | | | |
|---|---|---|---|
| 2011/0229809 A1* | 9/2011 | Nukada et al. | 430/56 |
| 2012/0189948 A1* | 7/2012 | Sonobe et al. | 430/56 |
| 2012/0196215 A1* | 8/2012 | Nukada et al. | 430/56 |
| 2013/0052571 A1* | 2/2013 | Yamada et al. | 430/56 |
| 2013/0052573 A1* | 2/2013 | Sasaki et al. | 430/56 |
| 2014/0072907 A1* | 3/2014 | Sasaki et al. | 430/56 |

FOREIGN PATENT DOCUMENTS

| | | |
|---|---|---|
| JP | H01-172837 A | 7/1989 |
| JP | H01-172838 A | 7/1989 |
| JP | H01-172839 A | 7/1989 |
| JP | H09-194535 A | 7/1997 |
| JP | 2000-206715 A | 7/2000 |
| JP | 2004-126136 A | 4/2004 |
| JP | 2007-025275 A | 2/2007 |
| JP | 2008-304664 A | 12/2008 |
| JP | 2012-180682 A | 9/2012 |
| WO | 2011/055792 A1 | 5/2011 |

OTHER PUBLICATIONS

Apr. 21, 2015 Office Action issued in Japanese Application No. 2011-181009.

Jul. 7, 2015 Office Action issued in Japanese Application No. 2011-181011.

* cited by examiner

REACTIVE COMPOUND, CHARGE TRANSPORTING FILM, PHOTOELECTRIC CONVERSION DEVICE, ELECTROPHOTOGRAPHIC PHOTORECEPTOR AND METHOD OF PRODUCING THE SAME, PROCESS CARTRIDGE, AND IMAGE FORMING APPARATUS

CROSS-REFERENCE TO RELATED APPLICATIONS

This application is a Divisional of application Ser. No. 13/430,242 filed Mar. 26, 2012 which is based on and claims priority under 35 USC 119 from Japanese Patent Application Nos. 2011-181009 and 2011-181011 both filed Aug. 22, 2011. The disclosure of the prior applications is hereby incorporated by reference herein in its entirety.

BACKGROUND

1. Technical Field

The present invention relates to a novel reactive compound, a charge transporting film, a photoelectric conversion device, an electrophotographic photoreceptor and a method of producing the same, a process cartridge, and an image forming apparatus.

2. Related Art

A cured film having a charge transport property is used in various fields such as in an electrophotographic photoreceptor, an organic electroluminescence element, a memory device, and a photoelectric conversion device such as a wavelength conversion device.

For example, in an electrophotographic image forming apparatus, the surface of an electrophotographic photoreceptor is charged with a predetermined polarity and potential by a charging device, and the surface of the charged electrophotographic photoreceptor is selectively erased by image exposure, whereby an electrostatic latent image is formed. Thereafter, a developing device attaches a toner to the electrostatic latent image so as to develop the latent image as a toner image, and the toner image is transferred to a recording medium by a transfer unit, whereby the toner image is discharged as a formed image.

In view of improving the strength of the electrophotographic photoreceptor, a suggestion for providing a protective layer on the surface of the electrophotographic photoreceptor has been offered.

SUMMARY

According to an aspect of the invention, there is provided a reactive compound represented by the following General Formula (I):

(I)

wherein in General Formula (I), F represents a charge transporting skeleton, D represents a group represented by the following General Formula (III), and m represents an integer of from 1 to 8:

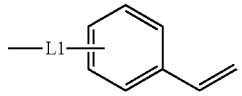

wherein in General Formula (III), L1 represents a divalent linking group including one or more —C(=O)—O— groups.

BRIEF DESCRIPTION OF THE DRAWINGS

Exemplary embodiments of the present invention will be described in detail based on the following figures, wherein.

DETAILED DESCRIPTION

Figure 1:
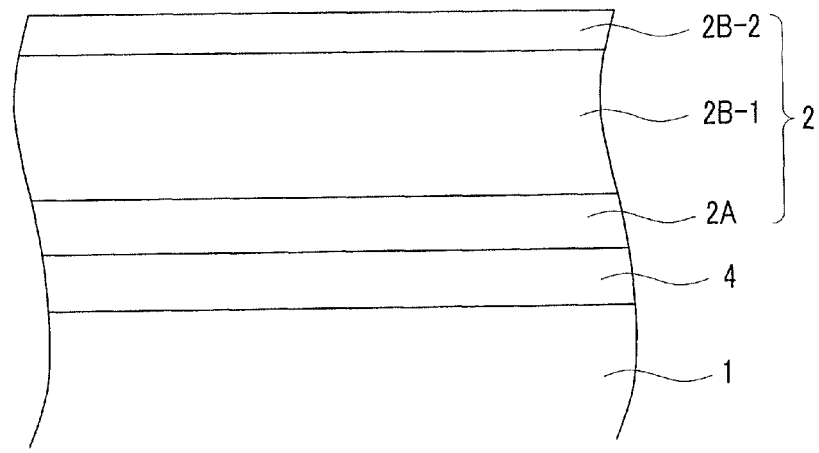
FIG. 1 is a schematic partial cross-sectional view showing an electrophotographic photoreceptor according to the exemplary embodiment.

Hereinafter, the exemplary embodiments of the invention will be described with appropriate reference to attached drawings.

[Reactive Compound]

A novel reactive compound according to the exemplary embodiment is a reactive compound represented by the following General Formula (I).

$$F\text{—}(D)_m \quad (I)$$

In General Formula (I), F represents a charge transporting skeleton, and D represents a group represented by the following General Formula (III). m represents an integer of from 1 to 8.

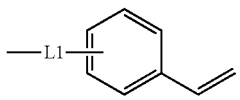
(III)

General Formula (III), L1 represents a divalent linking group including one or more —C(=O)—O— groups.

The reactive compound according to the exemplary embodiment includes a styrene skeleton as a chain-polymerizable group that has a structure in which a vinyl group (—CH=CH$_2$) directly binds to a benzene ring, and shows excellent compatibility with an aryl group which is a main skeleton of a charge transport agent. In a cured film using this compound, the aggregation of a charge transport structure and structures around the chain-polymerizable group that is caused by film shrinkage or curing is inhibited. Accordingly, it is considered that the fluctuation of mobility is inhibited even if the film is repeatedly used. In addition, in the reactive compound of the exemplary embodiment, the charge transporting skeleton and the styrene skeleton is linked to each other via a linking group including a —C(=O)—O— group. Therefore, it is considered that the strength of the cured film is further improved due to the interaction between the ester group and a nitrogen atom of the charge transporting skeleton or between the ester groups.

The reactive compound of the exemplary embodiment is desirably a compound represented by the following General Formula (II), in view of an excellent charge transport property.

General Formula (II)

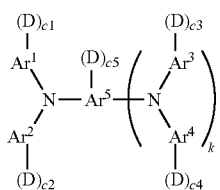
(II)

In General Formula (II), each of $Ar^1$ to $Ar^4$ independently represents a substituted or unsubstituted aryl group. $Ar^5$ represents a substituted or unsubstituted aryl group or a substituted or unsubstituted arylene group. D has the same definition as that of D in General Formula (I). Each of c1 to c5 represents an integer of from 0 to 2, and the sum of c1 to c5 is an integer of from 1 to 8. k is 0 or 1.

L1 in General Formula (III) is desirably a divalent linking group formed by combining —C(=O)—O— with —(CH$_2$)$_n$— (here, n is an integer of from 1 to 10).

Specifically, the group represented by General Formula (III) is desirably a group represented by the following General Formula (IV), and more desirably a group represented by the following General Formula (V).

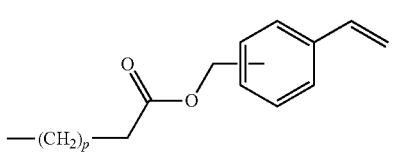
(IV)

In General Formula (IV), p represents an integer of from 0 to 4.

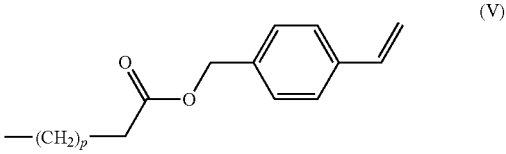
(V)

In General Formula (V), p represents an integer of from 0 to 4.

m in General Formula (I) or the sum of c1 to c5 in General Formula (II) is desirably an integer of from 2 to 6, more desirably an integer of from 3 to 6, and particularly desirably an integer of from 4 to 6.

Hereinafter, as a specific example to which the reactive compound according to the exemplary embodiment is applied, an electrophotographic photoreceptor will be described.

If the surface of an electrophotographic photoreceptor is made into a cured film, mechanical strength of the photoreceptor against repeated use is improved, but image quality itself and the stability of the image quality against repeated use are insufficient. Though unclear, the reason is considered to be as follows. By curing, the intermolecular distance and conformation of a chemical structure providing the charge transport property is changed from the state before curing, or chemical structures around the chain-polymerizable group and the chemical structures providing the charge transport property aggregate respectively, the state of the film before curing is changed. In addition, when a film that includes a binder resin in addition to a charge transport material having a chain-polymerizable functional group is cured, the compatibility between the structure of the charge transport material and the binder resin is reduced due to the curing, which is also considered as the reason.

In this respect, the compatibility between the mechanical strength and image quality that aims to the extension of the life of the electrophotographic photoreceptor is important.

The electrophotographic photoreceptor (hereinafter, simply referred to as a "photoreceptor" in some cases) according to the exemplary embodiment includes at least a conductive substrate and a photosensitive layer provided on the conductive substrate. The electrophotographic photoreceptor also includes a layer (Oc) as an uppermost surface layer which includes a polymerized or cured film of a composition containing the compound represented by General Formula (I), that is, a compound (referred to as a "charge transport material (A1)" appropriately) with a charge transport property that has a structure in which one or more charge transporting skeletons are linked to one or more styrene skeletons not conjugated with the charge transporting skeleton in the same molecule and includes a —C(=O)—O— group (that is, an ester group) in a linking group that links the charge transporting skeleton to the styrene skeleton.

In this exemplary embodiment, an electrophotographic photoreceptor is provided in which scratches do not easily leave even if the photoreceptor is repeatedly used, and image quality deterioration and image degradation rarely occur.

The reason causing the photoreceptor of the exemplary embodiment to exert effects is not clarified. However, the reason why the image quality deterioration rarely occurs even if the photoreceptor is repeatedly used is assumed to be as below. It is considered that in the photoreceptor that has a polymerized or cured film as an uppermost surface, film shrinkage or aggregation of the charge transport structure and the structure around the chain-polymerizable group is caused by the polymerization or curing. Consequently, if the photoreceptor surface receives mechanical stress due to the repeated use, the film itself is abraded or the chemical structure in a molecule is broken. Accordingly, the film shrinkage or aggregation state is changed greatly, and electrical characteristics of the photoreceptor are changed, which leads to the image quality deterioration.

On the other hand, in the exemplary embodiment, a styrene skeleton is used as the chain-polymerizable group, and the styrene skeleton has excellent compatibility with an aryl group which is a main skeleton of a charge transport agent. Therefore, it is considered that the image quality deterioration caused by the repeated use is inhibited since the aggregation of the charge transport structure and the structure around the chain-polymerizable group caused by the film shrinkage or curing is inhibited.

Moreover, in the exemplary embodiment, the charge transporting skeleton is linked to the styrene skeleton via a linking group including a —C(=O)—O— group. Therefore, it is considered that the strength of the polymerized or cured film is further improved due to the interaction between the ester group and a nitrogen atom in the charge transporting skeleton or between the ester groups.

The ester group included in the linking group may cause the deterioration of the charge transport property or image quality deterioration in a highly humid condition, due to the polarity or hydrophilicity of the ester group. However, in the exemplary embodiment, a styrene skeleton more hydrophobic than (meth)acryl or the like is used as a chain-polymerizable group, and accordingly, the deterioration of charge transport property or image quality deterioration such as image degradation is inhibited.

The photoreceptor according to the exemplary embodiment is not particularly limited in terms of the layer configuration or the like, as long as the photoreceptor has at least a conductive substrate and a photosensitive layer provided on the conductive substrate and includes a layer (Oc) as an uppermost surface layer which includes a polymerized or cured film of a composition containing a charge transport material (A1) which is the reactive compound represented by General Formula (I).

The photosensitive layer according to the exemplary embodiment may be a functional integration type of photosensitive layer having both a charge transporting function and a charge generating function or a functional separation type of photosensitive layer that includes charge transporting layer and a charge generating layer. Moreover, other layers such as an undercoat layer may also be provided.

If the surface of an electrophotographic photoreceptor is made into a polymerized or cured film, mechanical strength of the photoreceptor against repeated use is improved, but image quality itself and the stability of the image quality against repeated use are insufficient. Though unclear, the reason is considered to be as follows. By curing, the intermolecular distance and conformation of a chemical structure providing the charge transport property is changed from the state before curing, or chemical structures around the chain-polymerizable group and the chemical structures providing the charge transport property aggregate respectively, the state of the film before curing is changed. In addition, when a film that includes a binder resin in addition to a charge transport material having a chain-polymerizable functional group is cured, the compatibility between the structure of the charge transport material and the binder resin is reduced due to the curing, which is also considered as the reason.

In this respect, the compatibility between the mechanical strength and image quality that aims to the extension of the life of the electrophotographic photoreceptor is important.

The electrophotographic photoreceptor (hereinafter, simply referred to as a "photoreceptor" in some cases) according to the exemplary embodiment includes at least a conductive substrate and a photosensitive layer provided on the conductive substrate. The electrophotographic photoreceptor also includes a layer (Oc) as an uppermost surface layer which includes a polymerized or cured film of a composition containing one or more kinds of charge transport materials (A2) that have a structure in which one or more charge transporting skeletons are linked to one or more styrene skeletons not conjugated with the charge transporting skeleton in the same molecule and includes one or more groups selected from —C(=O)—, —N(R)—, —S—, or a group formed by combining —C(=O)— with —O—, —N(R)—, or —S— in a linking group that links the charge transporting skeleton to the styrene skeleton.

In this exemplary embodiment, an electrophotographic photoreceptor is provided in which scratches do not easily leave even if the photoreceptor is repeatedly used, and image quality deterioration and image degradation rarely occur.

The styrene skeleton included in the charge transport material (A2) of the exemplary embodiment refers to a structure in which a vinyl group (—CH=CH$_2$) directly binds to a benzene ring. The material may have a substituent instead of a hydrogen atom of the benzene ring, and examples of the substituent include an alkyl group, an alkoxy group, a halogen atom, and the like. However, the material desirably does not have a substituent.

(Presumptive Reasons Producing Effects)

The reason causing the photoreceptor of the exemplary embodiment to exert the effects is not clear. However, the reason why the image quality deterioration rarely occurs even if the photoreceptor is repeatedly used is assumed to be as below. It is considered that in the photoreceptor that has a polymerized or cured film as an uppermost surface, film shrinkage or aggregation of the charge transport structure and the structure around the chain-polymerizable group is caused by the polymerization or curing. Consequently, if the photoreceptor surface receives mechanical stress due to the repeated use, the film itself is abraded or the chemical structure in a molecule is broken. Accordingly, the film shrinkage or the aggregation state is changed greatly, and electrical characteristics of the photoreceptor are changed, which leads to the image quality deterioration. On the other hand, in the exemplary embodiment, a styrene skeleton is used as the chain-polymerizable group, and the styrene skeleton has excellent compatibility with an aryl group which is a main skeleton of a charge transport agent. Therefore, it is considered that the image quality deterioration caused by the repeated use is inhibited since the aggregation of the charge transport structure and the structure around the chain-polymerizable group caused by the film shrinkage or curing is inhibited.

Moreover, in the exemplary embodiment, the charge transporting skeleton is linked to the styrene skeleton via a linking group having a specific group such as —C(=O)—, —N(R)—, or —S—. Therefore, it is considered that the strength of the polymerized or cured film is further improved due to the interaction between the specific group and a nitrogen atom in the charge transporting skeleton or between the specific groups.

The specific group such as —C(=O)—, —N(R)—, or —S— may cause the deterioration of the charge transport property or image quality deterioration in a highly humid condition, due to the polarity or hydrophilicity of the group. However, in the exemplary embodiment, a styrene skeleton more hydrophobic than (meth)acryl or the like is used as a chain-polymerizable group, and accordingly, the deterioration of charge transport property or image quality deterioration such as ghost is not found.

[Electrophotographic Photoreceptor]

Hereinafter, the configuration of the electrophotographic photoreceptor of the exemplary embodiment will be described.

The photoreceptor according to the exemplary embodiment is not particularly limited in terms of the layer configuration or the like, as long as the photoreceptor includes at least a conductive substrate and a photosensitive layer provided on the conductive substrate, and has a layer (Oc) as an uppermost surface layer which includes a polymerized or cured film of a composition containing one or more kinds of charge transport materials (A2) that have a structure in which one or more charge transporting skeleton are linked to one or more styrene skeletons in the same molecule and includes one or more groups selected from —C(=O)—, —N(R)—, —S—, or a group formed by combining —C(=O)— with —O—, —N(R)—, or —S— in a linking group that links the charge transporting skeleton to the styrene skeleton.

The photosensitive layer according to the exemplary embodiment may be a functional integration type of photosensitive layer having both a charge transporting function and a charge generating function or a functional separation type of photosensitive layer that includes a charge transporting layer and a charge generating layer. Moreover, other layers such as an undercoat layer may also be provided.

Hereinafter, the configuration of the photoreceptor according to the exemplary embodiment will be described with reference to FIGS. 1 to 3, but the exemplary embodiment is not limited to FIGS. 1 to 3.

FIG. 1 is a schematic view showing an example of the layer configuration of the photoreceptor according to the exemplary embodiment. The photoreceptor shown in FIG. 1 has a layer configuration in which an undercoat layer 4, a charge generating layer 2A, a charge transporting layer 2B-1, and a charge transporting layer 2B-2 are laminated on a substrate 1 in this order, and a photosensitive layer is configured with three layers including the charge generating layer 2A and the charge transporting layers 2B-1 and 2B-2 (a first embodiment). In the photoreceptor shown in FIG. 1, the charge transporting layer 2B-2 corresponds the layer (Oc) of the exemplary embodiment that includes the reactive compound represented by General Formula (I). Hereinafter, this layer of the exemplary embodiment in the first embodiment will be referred to as a layer (Oc1) of the exemplary embodiment. The charge transporting layer 2B-2 serves as the uppermost surface layer also functions as a protective layer that protects the charge transporting layer 2B-1.

Figure 2:
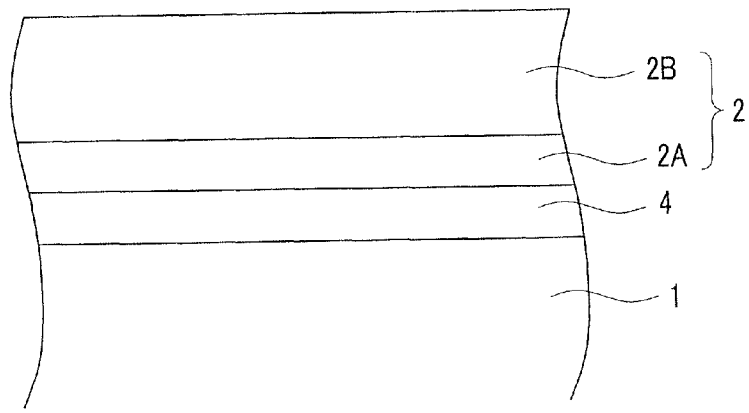
FIG. 2 is a schematic partial cross-sectional view showing an electrophotographic photoreceptor according to the exemplary embodiment.

FIG. 2 is a schematic view showing another example of the layer configuration in the photoreceptor according to the exemplary embodiment. The photoreceptor shown in FIG. 2 has a layer configuration in which the undercoat layer 4, a charge generating layer 2A, and a charge transporting layer 2B are laminated on the substrate 1 in this order, and the photosensitive layer 2 is configured with two layers including the charge generating layer 2A and the charge transporting layer 2B (a second embodiment). In the photoreceptor shown in FIG. 2, the charge transporting layer 2B corresponds to the layer (Oc) of the exemplary embodiment that includes the reactive compound represented by General Formula (I). Hereinafter, this layer of the exemplary embodiment in the second embodiment will be referred to as a layer (Oc2) of the exemplary embodiment.

Figure 3:
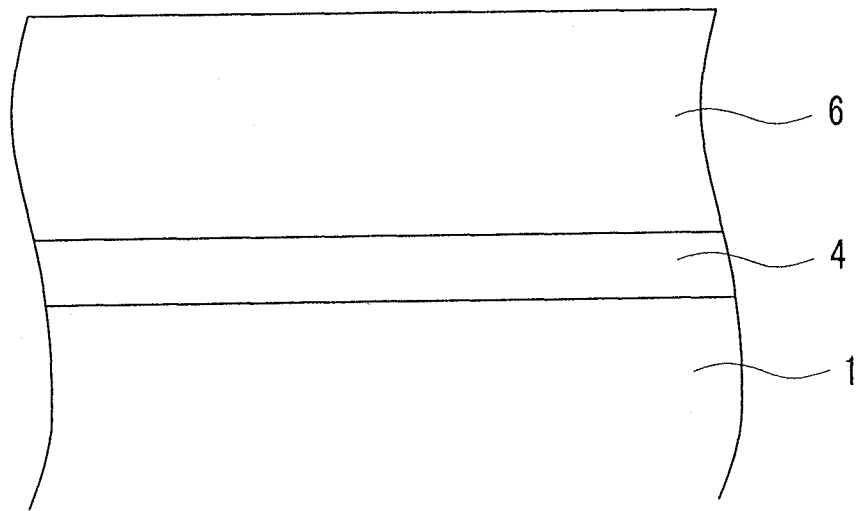
FIG. 3 is a schematic partial cross-sectional view showing an electrophotographic photoreceptor according to the exemplary embodiment.

FIG. 3 is a schematic view showing the other example of the layer configuration in the photoreceptor according to the exemplary embodiment. The photoreceptor shown in FIG. 3 has a layer configuration in which the undercoat layer 4 and a photosensitive layer 6 are laminated on the substrate 1 in this order, and the photosensitive layer 6 is a layer in which the functions of the charge generating layer 2A and the charge transporting layer 2B shown in FIG. 2 are integrated (a third embodiment). In the photoreceptor shown in FIG. 3, the functional integration type of photosensitive layer 6 corresponds to the layer (Oc) of the exemplary embodiment that includes the reactive compound represented by General Formula (I). Hereinafter, this layer of the exemplary embodiment in the third embodiment will be referred to as a layer (Oc3) of the exemplary embodiment.

Hereinafter, the first to third embodiments will be described respectively as examples of the photoreceptor according to the exemplary embodiment.

Conductive Substrate

Any material may be used as the conductive substrate so long as the material has been used in the related art. Examples of the material include paper, plastic film, or the like coated or impregnated with a conductivity-imparting agent, such as a plastic film provided with a thin film (for example, metals such as aluminum, nickel, chromium, and stainless steel; and a film of aluminum, titanium, nickel, chromium, stainless steel, gold, vanadium, tin oxide, indium oxide, indium tin oxide (ITO), or the like). The shape of the substrate is not limited to a cylindrical shape, and the substrate may have an approximately sheet shape or plate shape.

The conductive substrate particles desirably have conductivity in which volume resistivity is less than $10^7$ Ω·cm, for example.

When a metal pipe is used as the conductive substrate, the surface of the pipe may remain as it is or may be treated in advance with mirror surface cutting, etching, anodization, rough cutting, centerless grinding, sand blasting, wet honing, or the like.

—Undercoat Layer—

The undercoat layer is provided optionally, for the purposes of preventing light reflection in the surface of the conductive substrate, preventing unnecessary inflow of a carrier to the photosensitive layer from the conductive substrate, and the like.

The undercoat layer is configured with, for example, a binder resin and optionally other additives.

Examples of the binder resin included in the undercoat layer include known polymeric resin compounds such as an acetal resin including polyvinyl butyral, a polyvinyl alcohol resin, casein, a polyamide resin, a cellulose resin, gelatin, a polyurethane resin, a polyester resin, a methacrylic resin, an acrylic resin, a polyvinyl chloride resin, a polyvinyl acetate resin, a vinyl chloride-vinyl acetate-maleic anhydride resin, a silicone resin, a silicone-alkyd resin, a phenol resin, a phenol-formaldehyde resin, a melamine resin, and a urethane resin, a charge transporting resin having a charge transporting group, a conductive resin such as polyaniline, and the like. Among these, a resin insoluble in a coating solvent of the upper layer is desirably used, and particularly, a phenol resin, a phenol-formaldehyde resin, a melamine resin, a urethane resin, an epoxy resin, and the like are desirably used.

The undercoat layer may contain a metal compound such as a silicon compound, an organic zirconium compound, an organic titanium compound, an organic aluminum compound, or the like.

The proportion between the metal compound and the binder resin is not particularly limited and may be set within a range in which desired characteristics of the electrophotographic photoreceptor are obtained.

In order to adjust the surface roughness, resin particles may be added to the undercoat layer. Examples of the resin particles include silicone resin particles, crosslinked polymethyl methacrylate (PMMA) resin particles, and the like. In addition, to adjust the surface roughness, the surface of the formed undercoat layer may be polished. As the polishing method, buffing, sand blasting, wet honing, grinding, and the like are used.

Herein, examples of the configuration of the undercoat layer include a configuration that contains at least a binder resin and conductive particles. The conductive particles desirably have conductivity in which volume resistivity is, for example, less than $10^7$ Ω·cm.

Examples of the conductive particles include metal particles (particles of aluminum, copper, nickel, silver, or the like), conductive metallic oxide particles (particles of antimony oxide, indium oxide, tin oxide, zinc oxide, or the like), and conductive material particles (particles of carbon fiber, carbon black, graphite powder, or the like). Among these, conductive metallic oxide particles are suitable. The conductive particles may be used a mixture of two or more kinds thereof.

The conductive particles may be surface-treated using a hydrophobicizing agent (for example, a coupling agent) to adjust resistance.

The content of the conductive particles in the undercoat layer is, for example, desirably from 10% by weight to 80% by weight, and more desirably from 40% by weight to 80% by weight, based on the binder resin.

For the formation of the undercoat layer, a coating liquid for forming an undercoat layer obtained by adding the above components to a solvent is used.

As methods of dispersing the particles in the coating liquid for forming an undercoat layer, a media dispersing machine such as a ball mill, a vibration ball mill, an attritor, a sand mill, or a horizontal sand mill; stirring; and a media-less dispersing machine such as an ultrasonic dispersing machine, a roll mill, or a high pressure homogenizer are used. Herein, examples of the high pressure homogenizer include a collision type which disperses a dispersion through liquid-to-liquid collision or liquid-to-wall collision in a high pressure state, a penetration type which disperses the dispersion by causing the dispersion to penetrate a fine flow path in a high pressure state, and the like.

Examples of a method coating the coating liquid for forming an undercoat layer onto the conductive substrate include dip coating, push-up coating, wire bar coating, spray coating, blade coating, knife coating, curtain coating, and the like.

The film thickness of the undercoat layer is desirably 15 μm or more, and more desirably from 20 μm to 50 μm.

Though not shown in the drawing, an interlayer may be provided between the undercoat layer and the photosensitive layer.

Examples of the binder resin used for the interlayer include polymeric resin compounds such as an acetal resin including polyvinyl butyral, a polyvinyl alcohol resin, casein, a polyamide resin, a cellulose resin, gelatin, a polyurethane resin, a polyester resin, a methacrylic resin, an acrylic resin, a polyvinyl chloride resin, a polyvinyl acetate resin, a vinyl chloride-vinyl acetate-maleic anhydride resin, a silicone resin, a silicone-alkyd resin, a phenol-formaldehyde resin, a melamine resin, and organic metal compounds containing zirconium, titanium, aluminum, manganese, silicon atoms, and the like. These compounds may be used alone, or may be used as a mixture of plural compounds or as a polycondensate. Among these, an organic metal compound containing zirconium or silicon is suitable in respect that residual potential is low, and potential change caused by environments and repeated use is small in this compound.

For the formation of the interlayer, a coating liquid for forming an interlayer obtained by adding the above components to a solvent is used. As a coating method for forming the interlayer, general methods such as dip coating, push-up coating, wire bar coating, spray coating, blade coating, knife coating, and curtain coating are used.

The interlayer not only plays a role of improving a coating property of the upper layer, but also plays a role of an electrical blocking layer. However, when the film thickness of the interlayer is too large, an electrical barrier becomes too strong, which leads to desensitization or potential increase caused by repeated use in some cases. Accordingly, when the interlayer is formed, the film thickness thereof is desirably set in a range of from 0.1 μm to 3 μm. In addition, the interlayer in this case may be used as an undercoat layer.

—Charge Generating Layer—

The charge generating layer is configured with, for example, a charge generating material and a binder resin. Examples of the charge generating material include phthalocyanine pigments such as metal-free phthalocyanine, chlorogallium phthalocyanine, hydroxygallium phthalocyanine, dichlorotin phthalocyanine, and titanyl phthalocyanine. The examples particularly include chlorogallium phthalocyanine crystals having strong diffraction peaks at Bragg angles ($2\theta \pm 0.2°$) of at least 7.4°, 16.6°, 25.5°, and 28.3° with respect to an X-ray with CuKα characteristics, metal-free phthalocyanine crystals having strong diffraction peaks at Bragg angles ($2\theta \pm 0.2°$) of at least 7.7°, 9.3°, 16.9°, 17.5°, 22.4°, and 28.8° with respect to an X-ray with CuKα characteristics, hydroxygallium phthalocyanine crystals having strong diffraction peaks at Bragg angles ($2\theta \pm 0.2°$) of at least 7.5°, 9.9°, 12.5°, 16.3°, 18.6°, 25.1°, and 28.3° with respect to an X-ray with CuKα characteristics, and titanyl phthalocyanine crystals having strong diffraction peaks at Bragg angles ($2\theta \pm 0.2°$) of at least 9.6°, 24.1°, and 27.2° with respect to an X-ray with CuKα characteristics. Examples of the charge generating material also include a quinone pigment, a perylene pigment, an indigo pigment, a bisbenzimidazole pigment, an anthrone pigment, a quinacridone pigment, and the like. These charge generating materials may be used alone or used as a mixture of two or more kinds thereof.

Examples of the binder resin configuring the charge generating layer include a bisphenol A type or bisphenol Z type polycarbonate resin, an acrylic resin, a methacrylic resin, a polyarylate resin, a polyester resin, a polyvinyl chloride resin, a polystyrene resin, an acrylonitrile-styrene copolymer resin, an acrylonitrile-butadiene copolymer, a polyvinyl acetate resin, a polyvinyl formal resin, a polysulfone resin, a styrene-butadiene copolymer resin, a vinylidene chloride-acrylonitrile copolymer resin, a vinyl chloride-vinyl acetate-maleic anhydride resin, silicone resin, a phenol-formaldehyde resin, a polyacrylamide resin, a polyamide resin, a poly-N-vinylcarbazole resin, and the like. These binder resins may be used alone or used as a mixture of two or more kinds thereof.

The mixing ratio between the charge generating material and the binder resin is desirably in a range of from 10:1 to 1:10, for example.

For the formation of the charge generating layer, a coating liquid for forming a charge generating layer obtained by adding the above components in a solvent is used.

As a method of dispersing particles (for example, the charge generating material) in the coating liquid for forming a charge generating layer, a media dispersing machine such as a ball mill, a vibration ball mill, an attritor, a sand mill, or a horizontal sand mill; stirring; and a media-less dispersing machine such as an ultrasonic dispersing machine, a roll mill, or a high pressure homogenizer are used. Herein, examples of the high pressure homogenizer include a collision type which disperses a dispersion through liquid-to-liquid collision or liquid-to-wall collision in a high pressure state, a penetration type which disperses the dispersion by causing the dispersion to penetrate a fine flow path in a high pressure state, and the like.

Examples of a method coating the coating liquid for forming a charge generating layer onto the undercoat layer include dip coating, push-up coating, wire bar coating, spray coating, blade coating, knife coating, curtain coating, and the like.

The film thickness of the charge generating layer is set desirably in a range of from 0.01 μm to 5 μm, and more desirably in a range of from 0.05 μm to 2.0 μm.

—Charge Transporting Layer 2B-1 (Case of the First Embodiment)—

The charge transporting layer 2B-1 corresponds to the case of the first embodiment, and is configured with a charge transport material and optionally a binder resin.

Examples of the charge transport material include an oxadiazole derivative such as 2,5-bis(p-diethylaminophenyl)-1,3,4-oxadiazole; a pyrazoline derivative such as 1,3,5-triphenyl-pyrazoline or 1-[pyridyl-(2)]-3-(p-diethylaminostyryl)-5-(p-diethylaminostyryl)pyrazoline; an aromatic tertiary amino compound such as triphenylamine, N,N'-bis(3,4-dimethylphenyl)biphenyl-4-amine, tri(p-methylphenyl)aminyl-4-amine, or dibenzylaniline; an aromatic tertiary diamino compound such as N,N'-bis(3-methylphenyl)-N,N'-diphenylbenzidine; a 1,2,4-triazine derivative such as 3-(4'-dimethylaminophenyl)-5,6-di-(4'-methoxyphenyl)-1,2,4-triazine; a hydrazone derivative such as 4-dimethylaminobenzaldehyde-1,1-diphenylhydrazone; a quinazoline derivative such as 2-phenyl-4-styryl-quinazoline; a benzofuran derivative such as 6-hydroxy-2,3-di(p-methoxyphenyl)benzofuran; an α-stilbene derivative such as p-(2,2-diphenylvinyl)-N,N-diphenyl aniline; an enamine derivative; a carbazole derivative such as N-ethylcarbazole; hole transport materials such as poly-N-vinylcarbazole and a derivative thereof; a quinone-based compound such as chloranil or bromoanthraquinone; a tetracyanoquinodimethane-based compound; a fluorenone compound such as 2,4,7-trinitrofluorenone or 2,4,5,7-tetranitro-9-fluorenone; a xanthone-based compound; and an electron transport material such as a thiophene compound; and a polymer having a group including the above compounds in a main chain or a side chain thereof. These charge transport materials may be used alone or in combination of two or more kinds thereof.

Examples of the binder resin configuring the charge transporting layer 2B-1 include bisphenol A type or bisphenol Z type polycarbonate resin, an acrylic resin, a methacrylic resin, a polyarylate resin, a polyester resin, a polyvinyl chloride resin, a polystyrene resin, an acrylonitrile-styrene copolymer resin, an acrylonitrile-butadiene copolymer resin, a polyvinyl acetate resin, a polyvinyl formal resin, a polysulfone resin, a styrene-butadiene copolymer resin, a vinylidene chloride-acrylonitrile copolymer resin, a vinyl chloride-vinyl acetate-maleic anhydride resin, a silicone resin, a phenol-formaldehyde resin, a polyacrylamide resin, a polyamide resin, an insulating resin such as chlorinated rubber, an organic photoconductive polymer such as polyvinyl carbazole, polyvinyl anthracene, or polyvinyl pyrene, and the like. These binder resins may be used alone or used as a mixture of two or more kinds thereof.

The mixing ratio between the charge transport material and the binder resin is desirably from 10:1 to 1:5, for example.

The charge transporting layer 2B-1 is formed using a coating liquid for forming the charge transporting layer 2B-1 obtained by adding the above components to a solvent.

As a method of coating the coating liquid for forming the charge transporting layer 2B-1 onto the charge generating layer, a general method such as dip coating, push-up coating, wire bar coating, spray coating, blade coating, knife coating, or curtain coating is used.

The film thickness of the charge transporting layer 2B-1 is set desirably to a range of from 5 μm to 50 μm, and more desirably to a range of from 10 μm to 40 μm.

—Charge Transporting Layer 2B-2 (Corresponding to Layer (Oc1) of the Exemplary Embodiment in the First Embodiment)—

The layer (Oc1) of the exemplary embodiment is a layer which includes a polymerized or cured film of a composition containing one or more kinds of the charge transport materials (A1) that have a structure in which one or more charge transporting skeletons are linked to one or more styrene skeletons in the same molecule and includes one or more —C(=O)—O— groups in a linking group that links the charge transporting skeleton to the styrene skeleton, or containing one or more kinds of the charge transport materials (A2) that include one or more groups selected from —C(=O)—, —N(R)—, —S—, or a group formed by combining —C(=O)— with —O—, —N(R)—, or —S—.

The styrene skeleton included in the charge transport materials (A1) and (A2) in the exemplary embodiment is a structure in which a vinyl group (—CH=CH$_2$) directly binds to a benzene ring, but the material may have a substituent instead of the hydrogen atom of the benzene ring. Examples of the substituent include an alkyl group, an alkoxy group, a halogen atom, and the like. However, the material more desirably does not have a substituent.

Hereinafter, the composition for forming the charge transporting layer 2B-2 will be described.

As the charge transporting skeleton in the charge transport material (A1) of the exemplary embodiment, the skeleton described for the charge transporting layer 2B-1 is exemplified. As the charge transporting skeleton, those including an arylamine skeleton are desirable, and among these, those including a triarylamine skeleton are more desirable.

Hereinafter, more desirable structure of the charge transport material (A1) of the exemplary embodiment will be shown as General Formula (II).

General Formula (II)

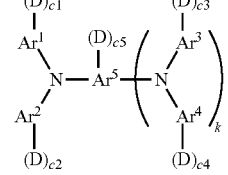

In General Formula (II), each of $Ar^1$ to $Ar^4$ independently represents a substituted or unsubstituted aryl group; $Ar^5$ represents a substituted or unsubstituted aryl group or a substituted or unsubstituted arylene group; and D represents a group represented by General Formula (III). In General Formula (III), L1 represents a divalent linking group including one or more —C(=O)—O— group.

Each of c1 to c5 in General Formula (II) represents an integer of from 0 to 2 and may be the same as or different from each other. Here, the sum of c1 to c5 in General Formula (II) is an integer of from 1 to 8. k is 0 or 1.

The total number of styrene skeletons in General Formula (I) corresponds to m. The total number of styrene skeletons in General Formula (II) corresponds to a value of c1+c2+k×(c3+c4)+c5.

The lower limit of the total number of styrene skeletons in General Formulae (I) and (II) is desirably 2 or greater, more desirably 3 or greater, and even more desirably 4 or greater, in view of obtaining a stronger crosslinked film (cured film). If the number of the chain-polymerizable group in a molecule is too large, as the polymerization (crosslinking) reaction proceeds, it becomes more difficult for molecules to move. Consequently, chain-polymerization reactivity is reduced, and the proportion of unreacted chain-polymerizable groups increases. Therefore, the upper limit of the number of the styrene skeletons in General Formula (II) is desirably 7 or less, and more desirably 6 or less.

D in General Formula (II) is a group represented by General Formula (III), and L1 represents a divalent linking group including one or more —C(=O)—O— groups.

L1 in General Formula (III) represented by D in General Formula (II) is not particularly limited as long as L1 is a divalent linking group including the ester group. Specific examples of L1 include divalent groups formed by arbitrarily combining the ester group with a residue of saturated hydrocarbon (including all of linear, branched, and cyclic hydrocarbons) or aromatic hydrocarbon as well as an oxygen atom. L1 is desirably formed by arbitrarily combining the ester group with a residue of linear saturated hydrocarbon.

The total number of carbon atoms included in L1 in General Formula (II) is desirably from 1 to 20, and more desirably from 2 to 10, in view of the density and chain polymerization reactivity of the styrene skeletons in a molecule.

In General Formula (II), each of $Ar^1$ to $Ar^4$ independently represents a substituted or unsubstituted aryl group. Each of $Ar^1$ to $Ar^4$ may be the same as or different from each other. Herein, examples of the substituent in the substituted aryl group include an alkyl group having from 1 to 4 carbon atoms, an alkoxy group having from 1 to 4 carbon atoms, a phenyl group substituted with an alkoxy group having from 1 to 4 carbon atoms, an unsubstituted phenyl group, an aralkyl group having from 7 to 10 carbon atoms, and a halogen atom, other than D.

$Ar^1$ to $Ar^4$ are desirably any one of the following Structural Formulae (1) to (7). The following Structural Formulae (1) to (7) in common exhibit "-(D)c" that may be linked to each of $Ar^1$ to $Ar^4$. Herein, "-(D)c" has the same definition as "-(D)c1 to -(D)c4" in General Formula (II), and desirable examples thereof are also the same.

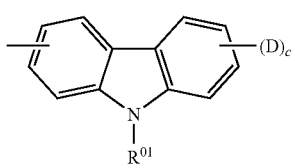

(1)

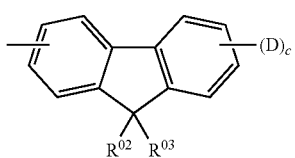

(2)

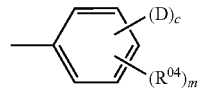

(3)

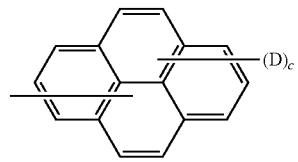

(4)

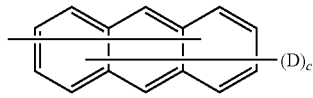

(5)

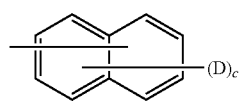

(6)

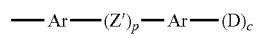

(7)

In the Structural Formula (1), $R^{01}$ represents one kind selected from a group consisting of a hydrogen atom, an alkyl group having from 1 to 4 carbon atoms, a phenyl group substituted with an alkyl group having from 1 to 4 carbon atoms or an alkoxy group having from 1 to 4 carbon atoms, an unsubstituted phenyl group, and an aralkyl group having from 7 to 10 carbon atoms.

In the Structural Formulae (2) and (3), each of $R^{02}$ to $R^{04}$ independently represents one kind selected from a group consisting of a hydrogen atom, an alkyl group having from 1 to 4 carbon atoms, an alkoxy group having from 1 to 4 carbon atoms, a phenyl group substituted with an alkoxy group having from 1 to 4 carbon atoms, an unsubstituted phenyl group, an aralkyl group having from 7 to 10 carbon atoms, and a halogen atom. m represents an integer of from 1 to 3.

In the Structural Formula (7), Ar represents a substituted or unsubstituted arylene group.

Herein, Ar in Formula (7) is desirably represented by the following Structural Formula (8) or (9).

(8)

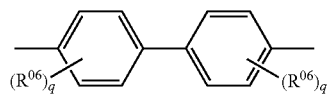

(9)

In the Structural Formulae (8) and (9), each of $R^{05}$ and $R^{06}$ independently represents one kind selected from a group consisting of a hydrogen atom, an alkyl group having from 1 to 4 carbon atoms, an alkoxy group having from 1 to 4 carbon atoms, a phenyl group substituted with an alkoxy group having from 1 to 4 carbon atoms, an unsubstituted phenyl group, an aralkyl group having from 7 to 10 carbon atoms, and a halogen atom. Each q represents an integer of from 1 to 3.

In the Structural Formula (7), Z' represents a divalent organic linking group. Z' is desirably represented by any one of the following Structural Formulae (10) to (17). p represents 0 or 1.

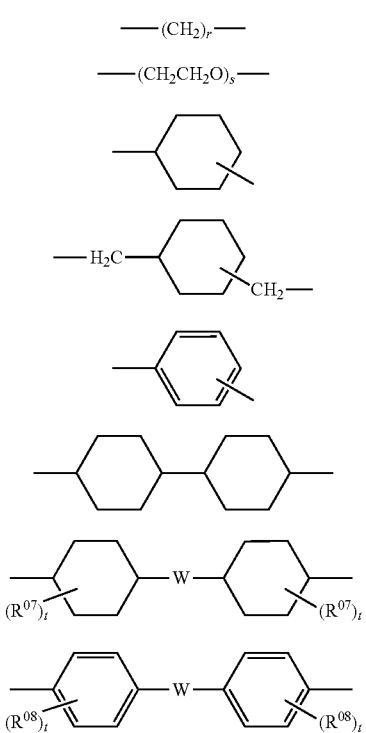

(10)
(11)
(12)
(13)
(14)
(15)
(16)
(17)

In the Structural Formulae (10) to (17), each of $R^{07}$ and $R^{08}$ independently represents one kind selected from a group consisting of a hydrogen atom, an alkyl group having from 1 to 4 carbon atoms, a phenyl group substituted with an alkyl group having from 1 to 4 carbon atoms or an alkoxy group having from 1 to 4 carbon atoms, an unsubstituted phenyl group, an aralkyl group having from 7 to 10 carbon atoms, and a halogen atom; W represents a divalent group; each of r and s independently represents an integer of from 1 to 10; and each t represents an integer of from 1 to 3.

W in the Structural Formulae (16) and (17) is desirably any one of divalent groups represented by the following (18) to (26). Here, in Formula (25), u represents an integer of from 0 to 3.

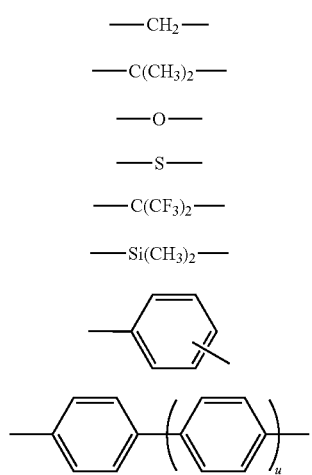

(18)
(19)
(20)
(21)
(22)
(23)
(24)
(25)

(26)

In General Formula (II), when k is 0, $Ar^5$ is a substituted or unsubstituted aryl group, and examples of the aryl group include the same aryl group as exemplified in the description for $Ar^1$ to $Ar^4$. When k is 1, $Ar^5$ is a substituted or unsubstituted arylene group, and examples of the arylene group include an arylene group obtained by removing one hydrogen atom in a desired position from the aryl group exemplified in the description for $Ar^1$ to $Ar^4$.

The composition for forming the charge transporting layer 2B-2 may further contain at least one or more kinds of the charge transport material (A2) of the exemplary embodiment. The charge transport material (A2) of the exemplary embodiment is not particularly limited as long as this material is a compound that has a structure in which one or more charge transporting skeletons are linked to one or more styrene skeletons in the same molecule and includes one or more groups selected from —C(=O)—, —N(R)—, —S—, or a group formed by combining —C(=O)— with —O—, —N(R)—, or —S— in a linking group that links the charge transporting skeleton to the styrene skeleton. Herein, R represents a hydrogen atom, an alkyl group, an aryl group, or an aralkyl group. As the charge transporting skeleton in the charge transport material (A2) of the exemplary embodiment, those described for the charge transporting layer 2B-1 are exemplified. As the charge transporting skeleton, those including an arylamine skeleton are desirable, and among these, those including a triarylamine skeleton are more desirable.

Hereinafter, a more desirable structure of the charge transport material (A2) of the exemplary embodiment will be shown as General Formula (II')

(II')

In General Formula (II'), each of $Ar^1$ to $Ar^4$ independently represents a substituted or unsubstituted aryl group; $Ar^5$ represents a substituted or unsubstituted aryl group or a substituted or unsubstituted arylene group; and D is a group represented by General Formula (III').

(III')

In General Formula (III'), L2 represents a divalent linking group including one or more groups selected from —C(=O)—, —N(R)—, —S—, or a group formed by combining —C(=O)— with —O—, —N(R)—, or —S—. R represents a hydrogen atom, an alkyl group, an aryl group, or an aralkyl group.

Each of c1 to c5 in General Formula (II') represents an integer of from 0 to 2, and may be the same as or different from each other. Here, the sum of c1 to c5 in General Formula (II') is an integer of from 1 to 8. k is 0 or 1.

The total number of styrene skeletons in General Formula (I') corresponds to m. The total number of styrene skeletons in General Formula (II') corresponds to a value of c1+c2+k×(c3+c4)+c5.

The lower limit of the total number of styrene skeletons in General Formulae (I') and (II') is desirably 2 or greater, and more desirably 4 or greater, in view of obtaining a stronger crosslinked film (cured film). Generally, if the number of the chain-polymerizable group in a molecule is too large, as the polymerization (crosslinking) reaction proceeds, it becomes more difficult for molecules to move. Consequently, chain-polymerization reactivity is reduced, and the proportion of unreacted chain-polymerizable groups increases. Therefore, the upper limit of the total number of the styrene skeletons in General Formula (I') is desirably 7 or less, and more desirably 6 or less.

D in General Formula (II') is a group represented by General Formula (III'). L2 is a divalent linking group including one or more groups (hereinafter, referred to as a specific group (Lx)) selected from —C(=O)—, —N(R)—, —S—, or a group formed by combining —C(C=O)— with —O—, —N(R)—, or —S—. Herein, R represents a hydrogen atom, an alkyl group, an aryl group, or an aralkyl group.

The specific group (Lx) is desirably —C(=O)—, —N(R)—, —S—, —C(=O)—O—, —C(=O)—N(R)—, —C(=O)—S—, —O—C—(=O)—O—, or —O—C—(=O)—N(R)—, more desirably —N(R)—, —S—, —C(=O)—O—, or —C(=O)—N(H)—, and most desirably —C(=O)—O—.

L2 in General Formula (III') is not particularly limited as long as L2 includes the specific group (Lx). Specific examples of L2 include divalent groups formed by arbitrarily combining the specific group (Lx) with a residue of saturated hydrocarbon (including all of linear, branched, and cyclic hydrocarbons) or aromatic hydrocarbon, and an oxygen atom. L2 is desirably formed by arbitrarily combining the specific group (Lx) with a residue of linear saturated hydrocarbon and an oxygen atom.

The total number of carbon atoms included in L2 in General Formula (III') is desirably from 1 to 20, and more desirably from 2 to 10, in view of the density and chain polymerization reactivity of the styrene skeletons in a molecule.

In General Formula (II'), each of $Ar^1$ to $Ar^4$ independently represents a substituted or unsubstituted aryl group. Each of $Ar^1$ to $Ar^4$ may be the same as or different from each other. Herein, examples of the substituent in the substituted aryl group include an alkyl group having from 1 to 4 carbon atoms, an alkoxy group having from 1 to 4 carbon atoms, a phenyl group substituted with an alkoxy group having from 1 to 4 carbon atoms, an unsubstituted phenyl group, an aralkyl group having from 7 to 10 carbon atoms, and a halogen atom, other than D.

$Ar^1$ to $Ar^4$ are desirably any one of the above Structural Formulae (1) to (7). The Structural Formulae (1) to (7) in common exhibit "-(D)c" that may be linked to each of $Ar^1$ to $Ar^4$. Herein, "-(D)c" has the same definition as "-(D)c1 to -(D)c4" in General Formula (II'), and desirable examples thereof are also the same.

Hereinafter, specific examples of the compounds represented by General Formulae (I) and (I') will be shown. However, the compounds represented by General Formulae (I) and (I') are not limited to the examples.

First, as specific examples of a charge transporting skeleton F in a case where the total number of D in General Formulae (I) and (I') is 1, "(1)-1" to "(1)-25" will be shown. However, the exemplary embodiment is not limited to the examples. In addition, a portion * in each structural formula shows that this portion is linked to D in General Formulae (I) and (I').

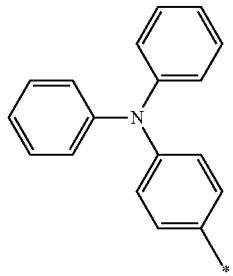

(1)-1

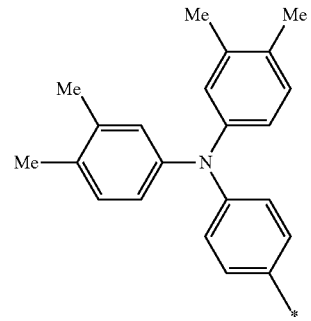

(1)-2

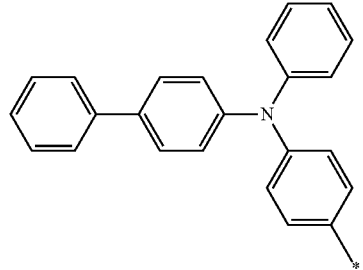

(1)-3

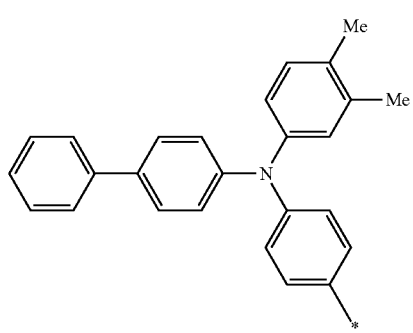

(1)-4

(1)-5
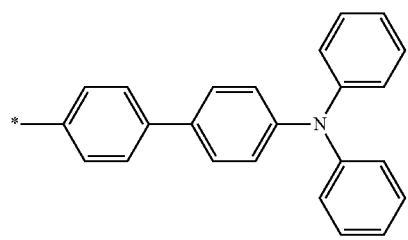
(1)-6
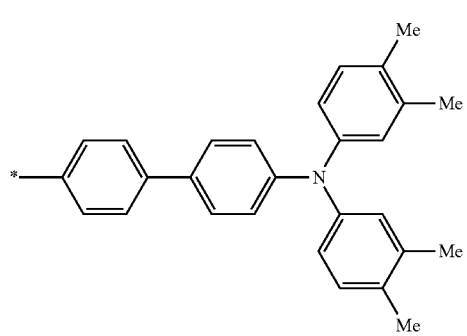
(1)-7
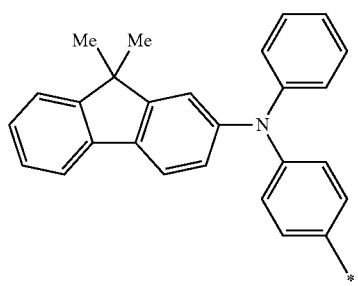
(1)-8
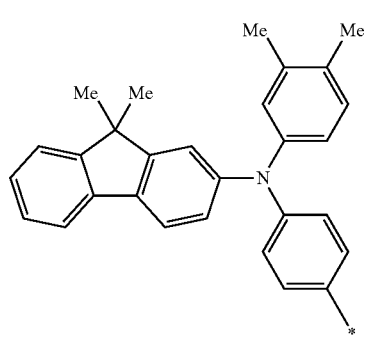
(1)-9
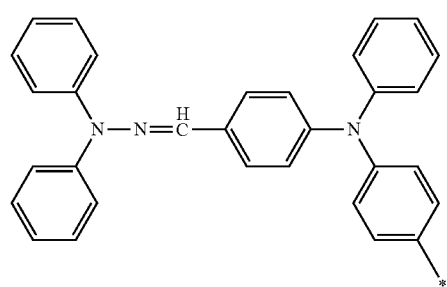
(1)-10
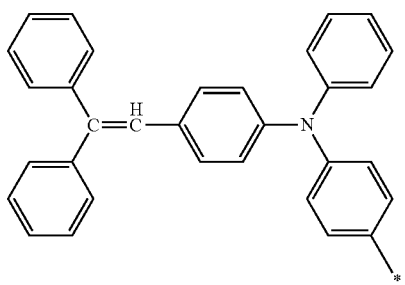
(1)-11
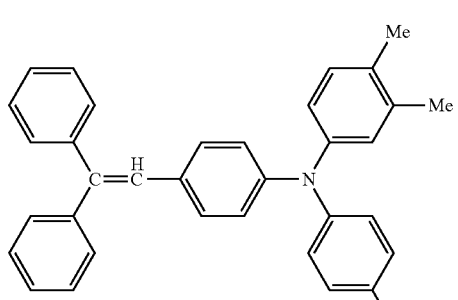
(1)-12
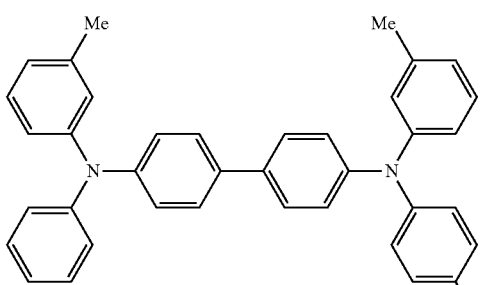
(1)-13
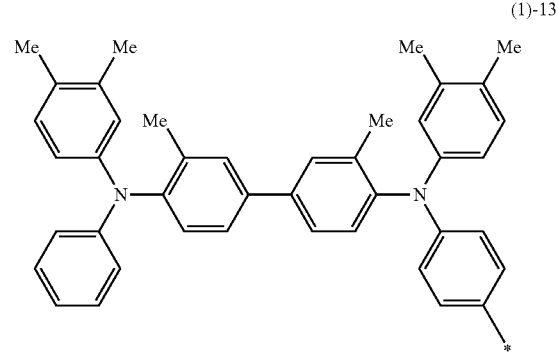

(1)-14
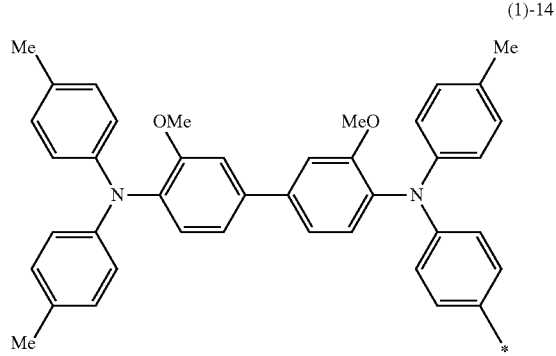
(1)-15
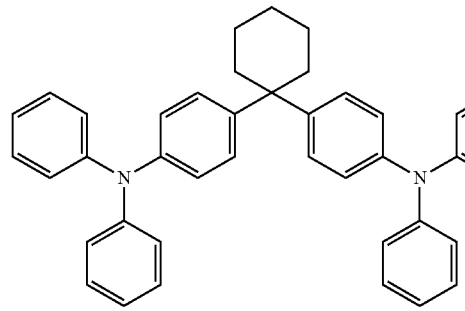
(1)-16
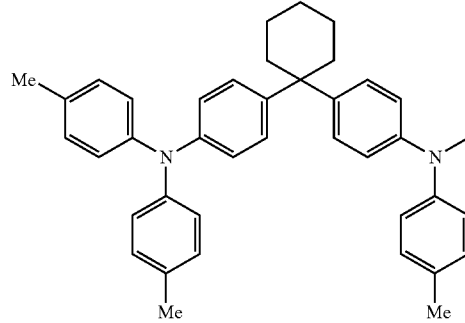
(1)-17
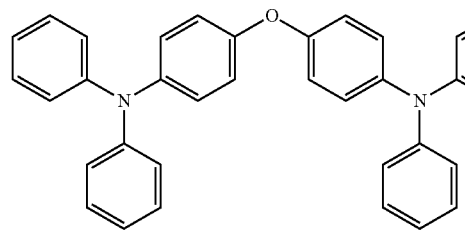
(1)-18
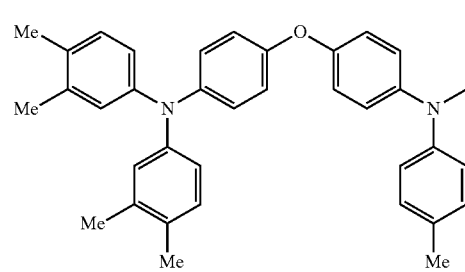
(1)-19
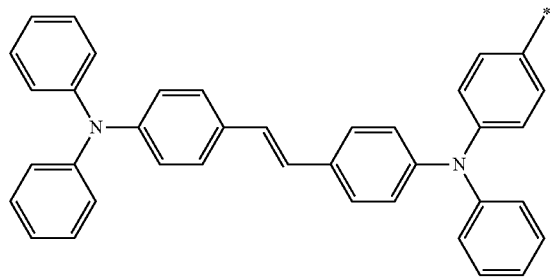
(1)-20
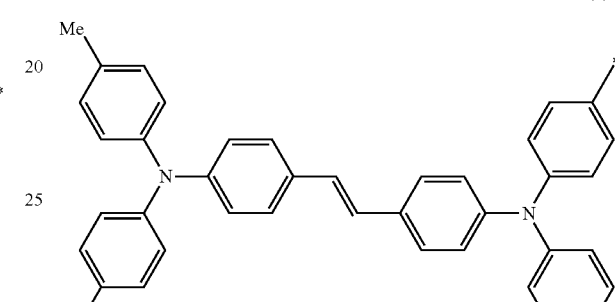
(1)-21
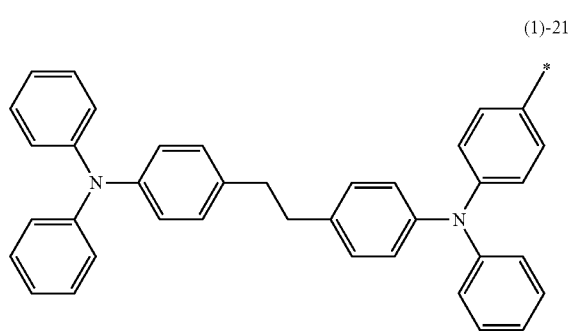
(1)-22
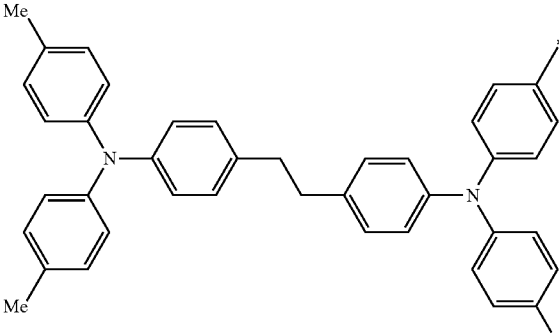

(1)-23
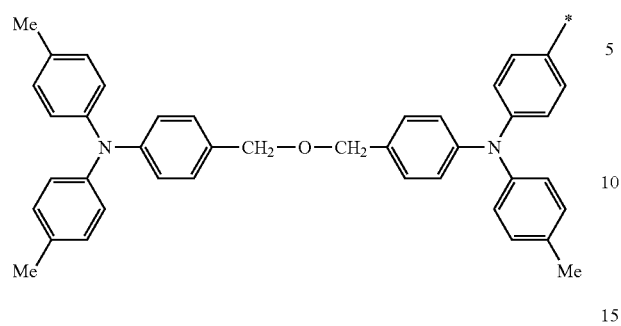
(1)-24
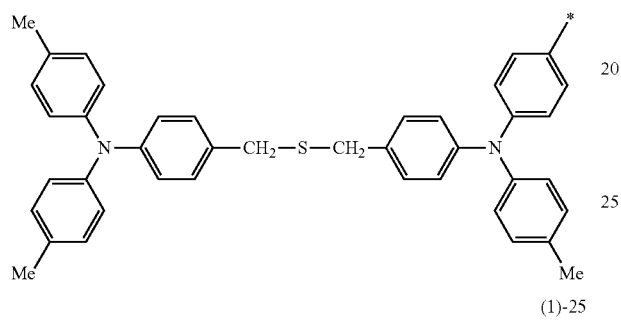
(1)-25
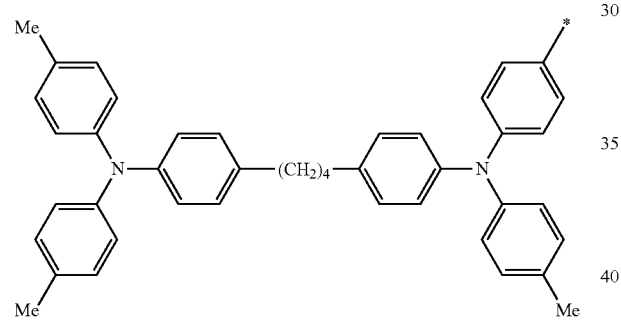
Next, as specific examples of the charge transporting skeleton F in a case where the total number of D in General Formulae (I) and (I') is 2, "(2)-1" to "(2)-29" will be shown. However, the exemplary embodiment is not limited to the examples. In addition, a portion * in each structural formula shows that this portion is linked to D in General Formulae (I) and (I').
(2)-1
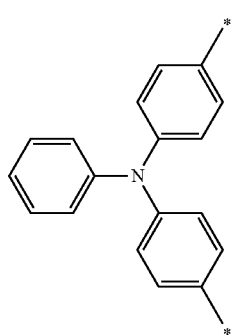
(2)-2
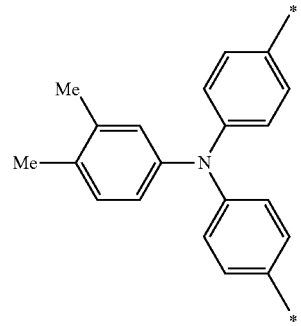
(2)-3
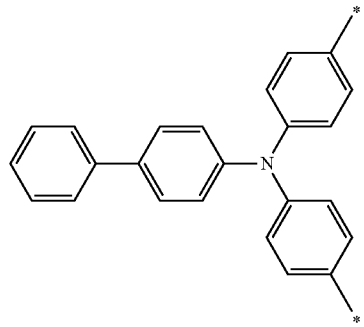
(2)-4
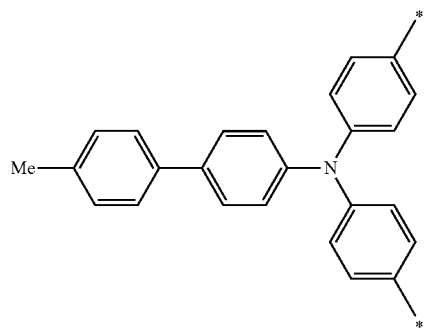
(2)-5
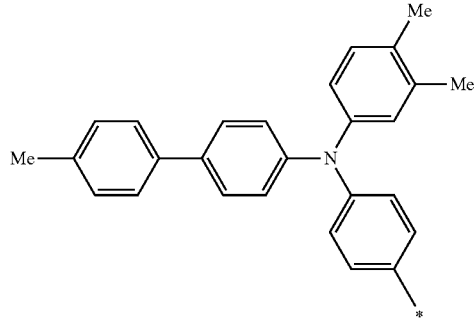

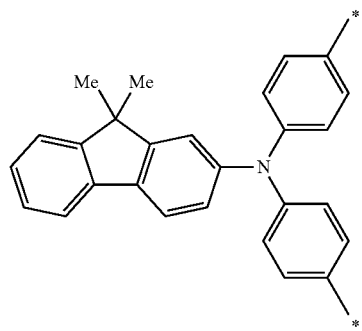
(2)-6
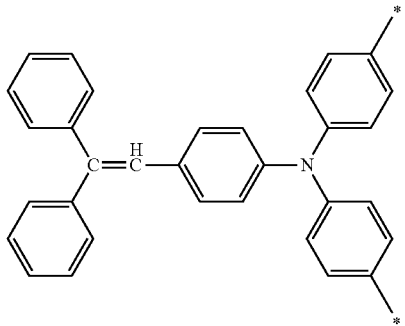
(2)-10
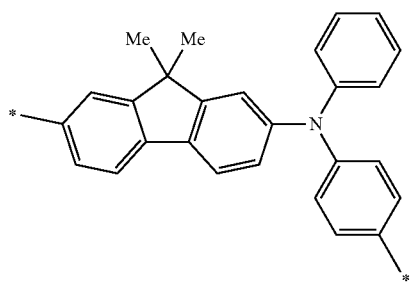
(2)-7
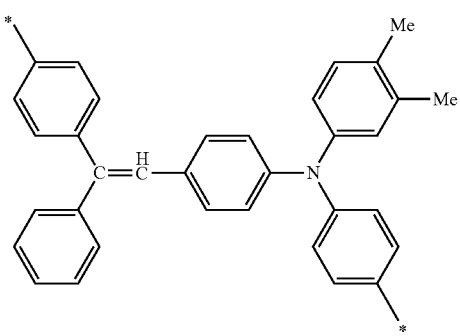
(2)-11
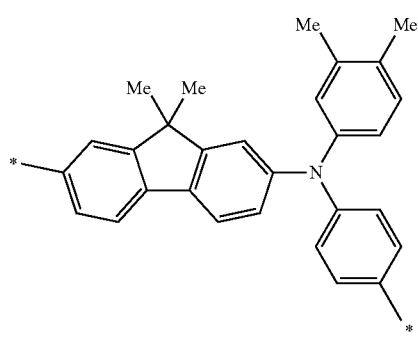
(2)-8
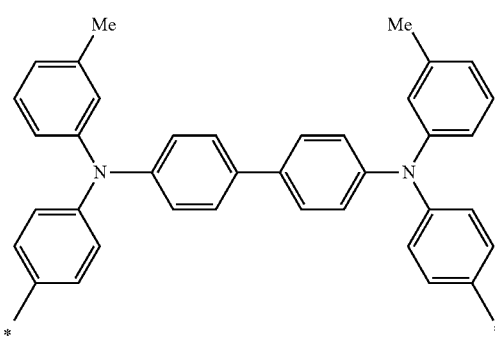
(2)-12
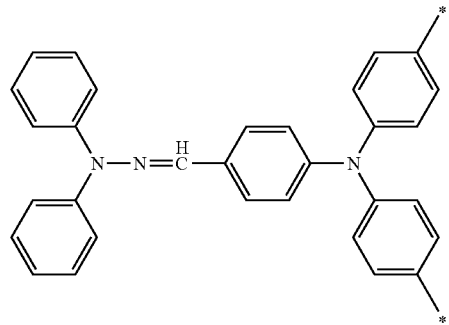
(2)-9
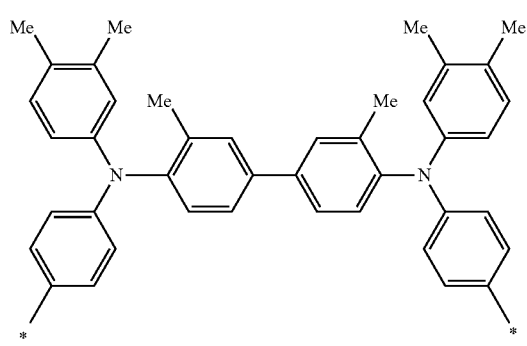
(2)-13

-continued
(2)-14
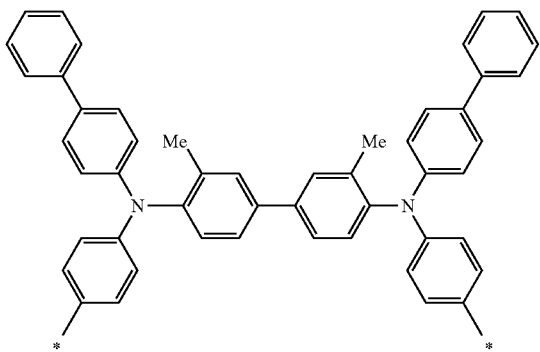
(2)-19
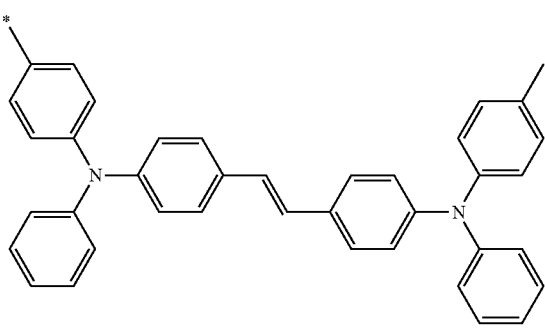
(2)-15
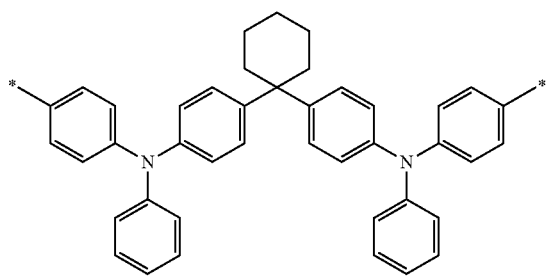
(2)-16
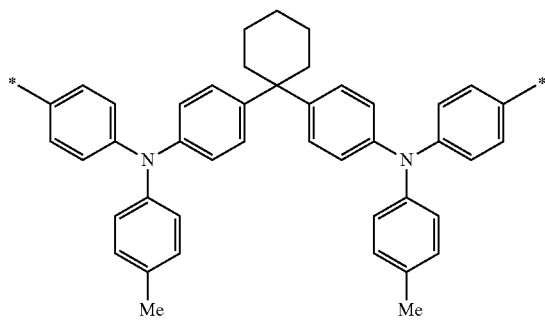
(2)-17
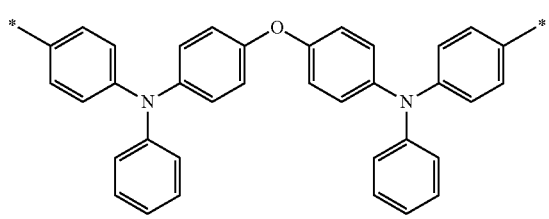
(2)-18
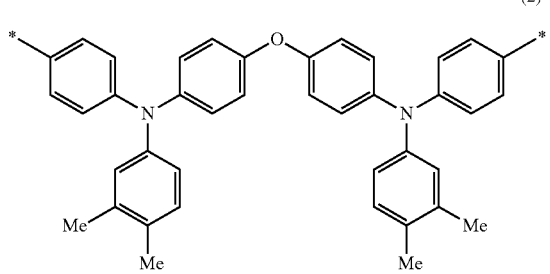
(2)-20
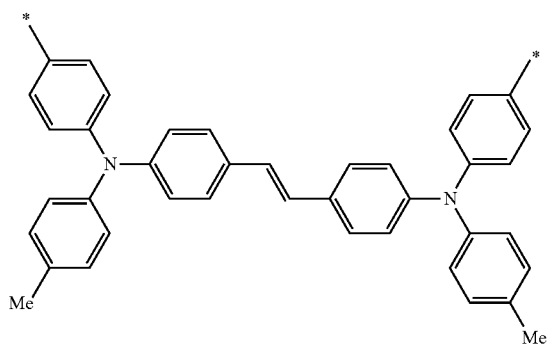
(2)-21
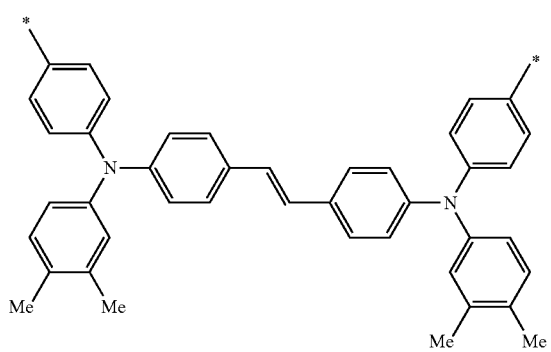
(2)-22
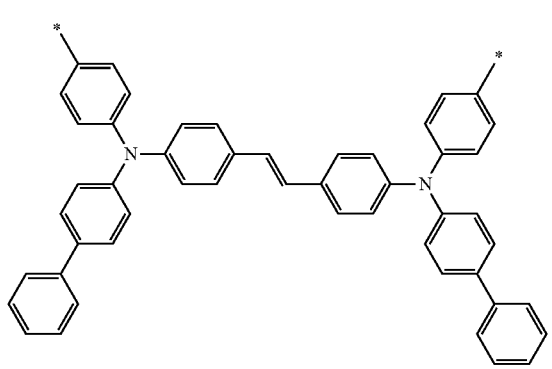

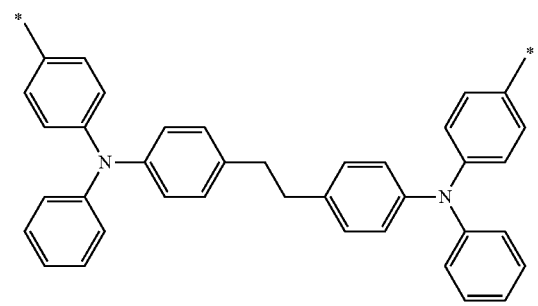
(2)-23
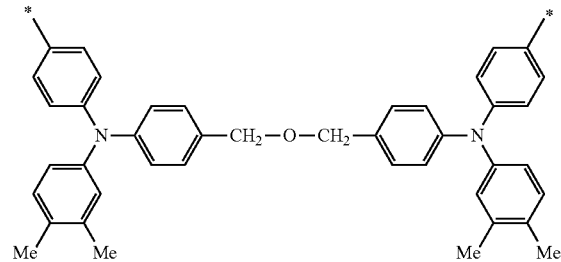
(2)-27
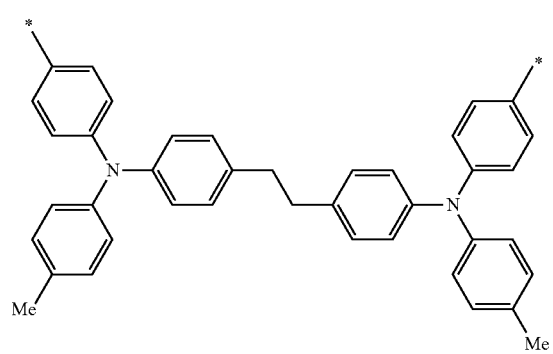
(2)-24
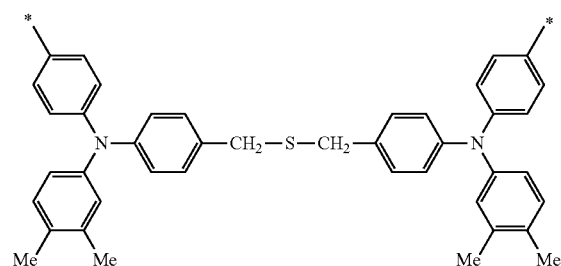
(2)-28
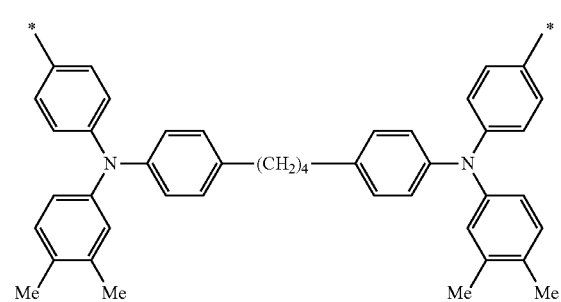
(2)-29
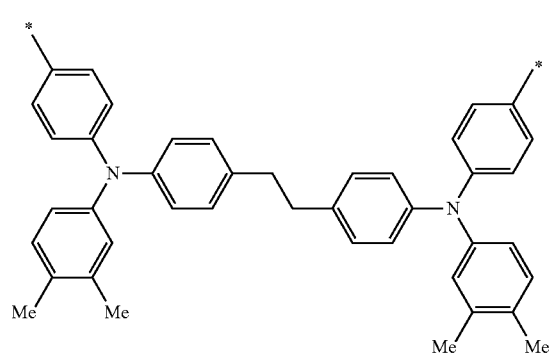
(2)-25
Next, as specific examples of the charge transporting skeleton F in a case where the total number of D in General Formulae (I) and (I') is 3, "(3)-1" to "(3)-29" will be shown. However, the exemplary embodiment is not limited to the examples. In addition, a portion * in each structural formula shows that this portion is linked to D in General Formulae (I) and (I').
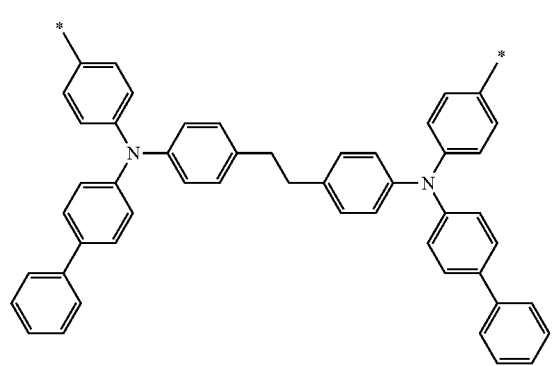
(2)-26
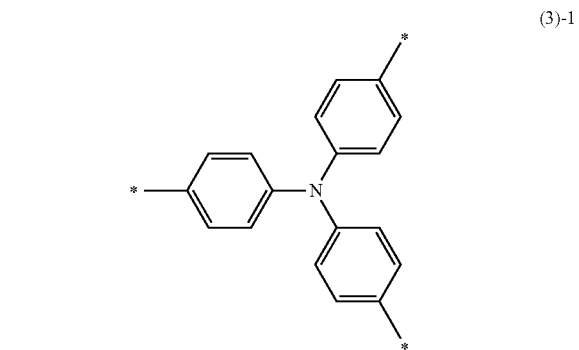
(3)-1

-continued
(3)-2
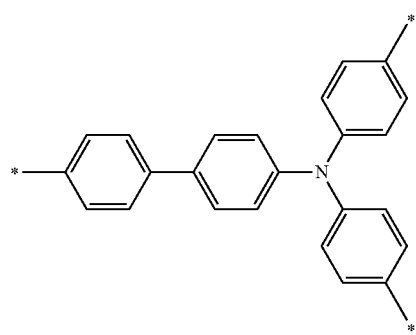
(3)-6
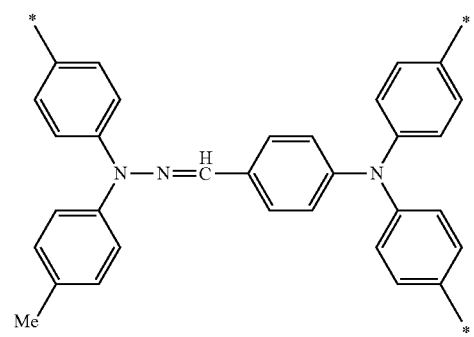
(3)-3
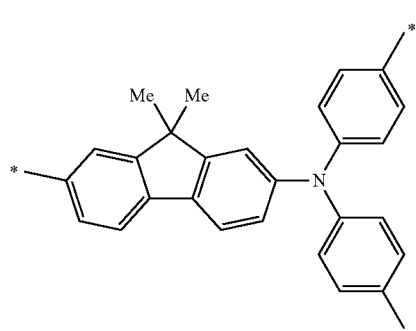
(3)-7
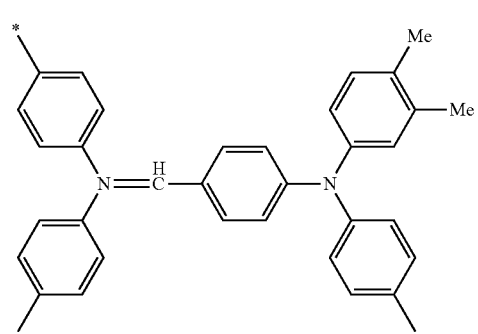
(3)-4
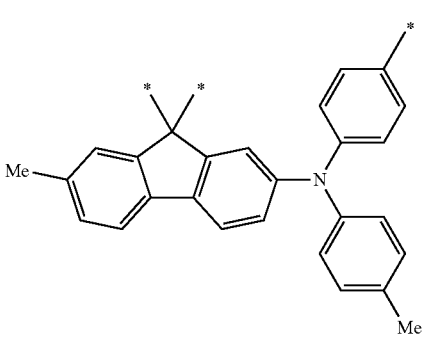
(3)-8
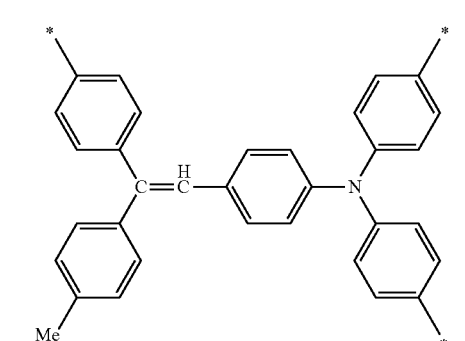
(3)-5
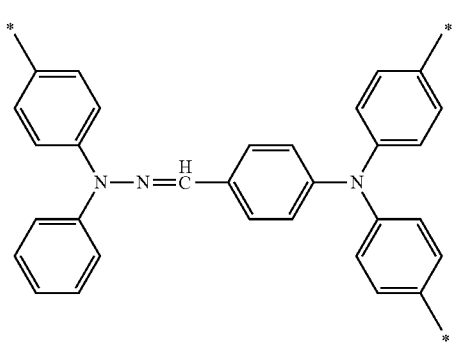
(3)-9
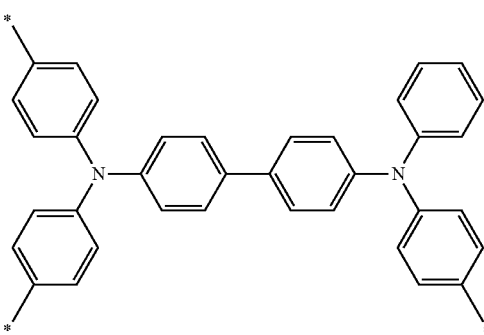

(3)-10
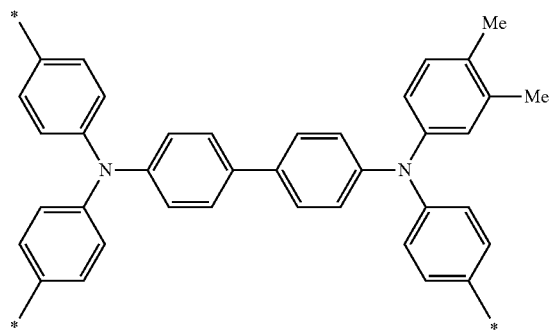
(3)-11
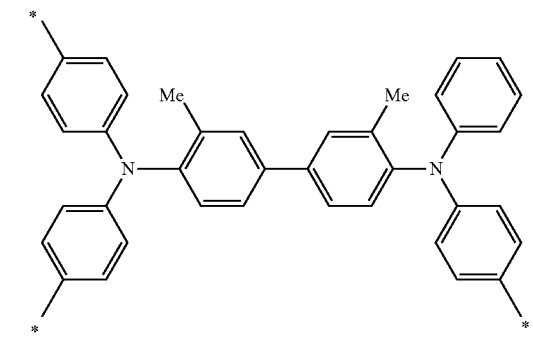
(3)-12
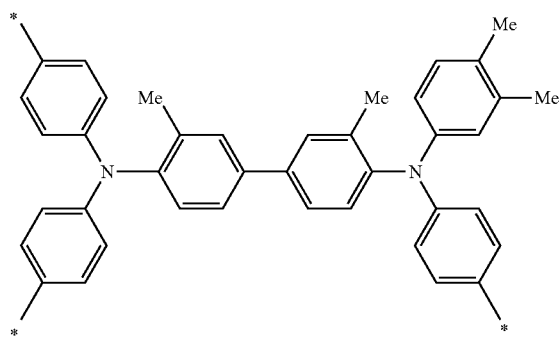
(3)-13
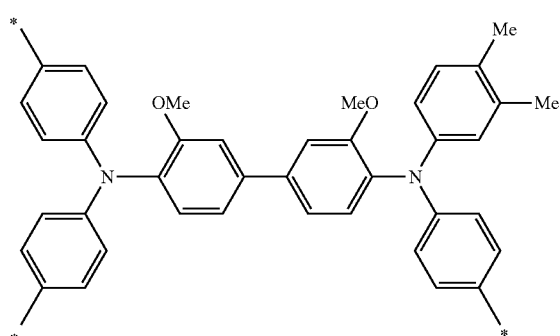
(3)-14
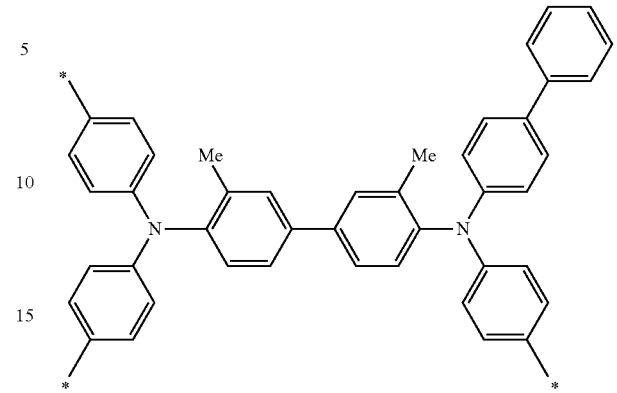
(3)-15
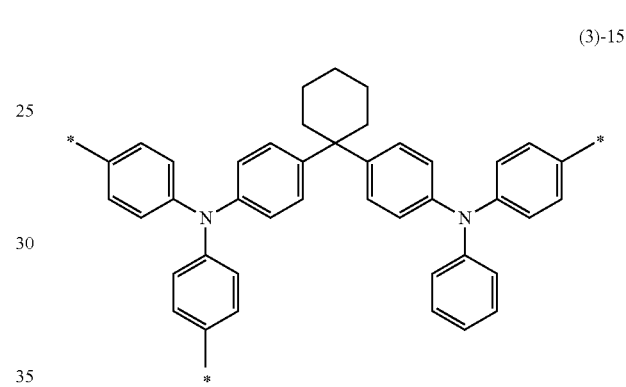
(3)-16
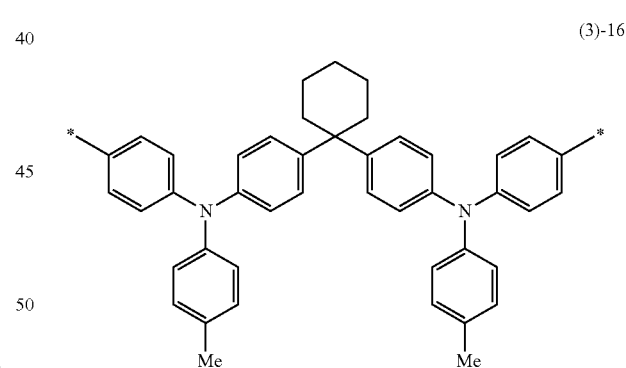
(3)-17
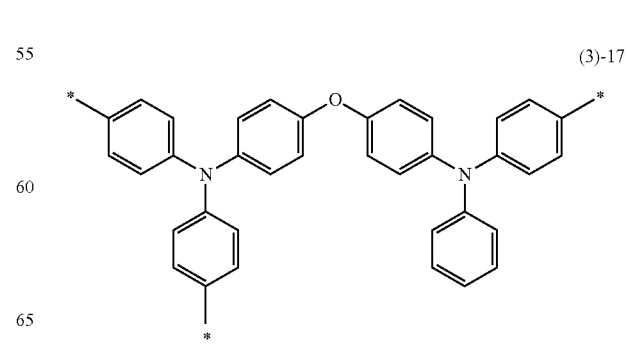

(3)-18
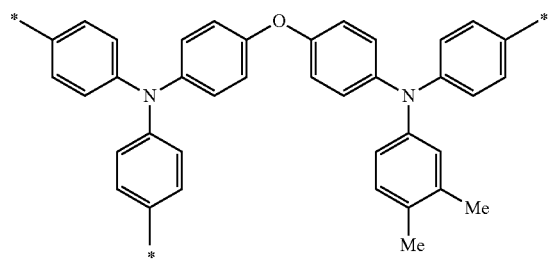
(3)-19
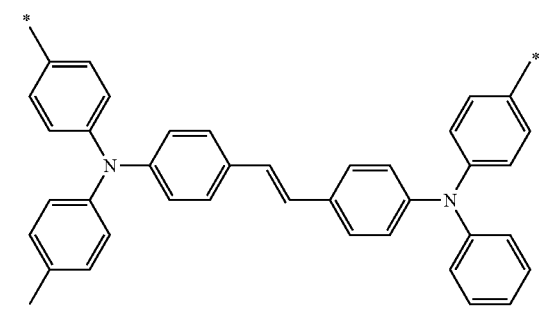
(3)-20
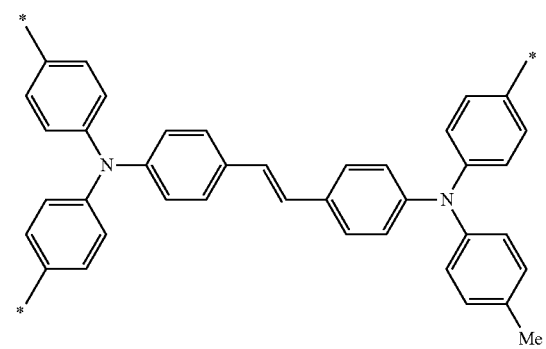
(3)-21
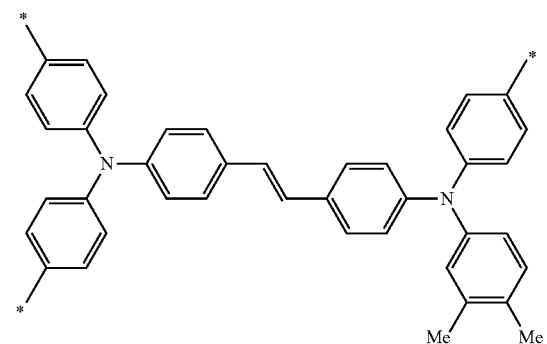
(3)-22
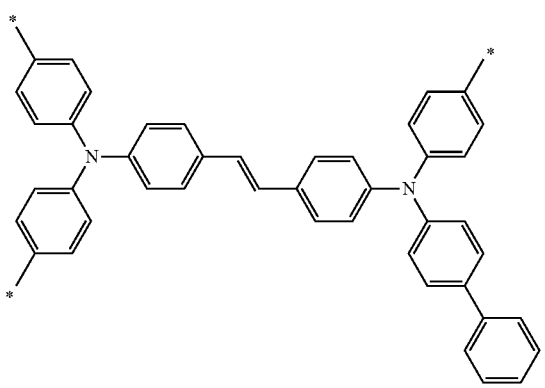
(3)-23
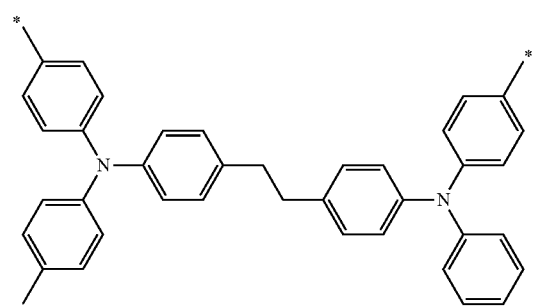
(3)-24
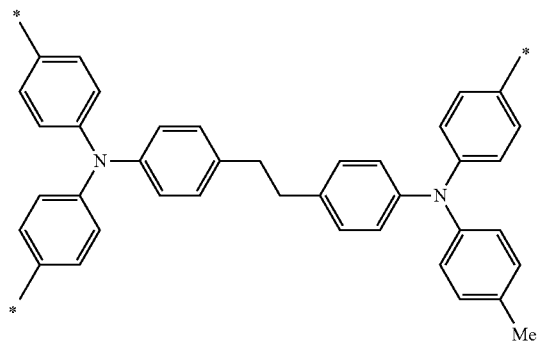
(3)-25
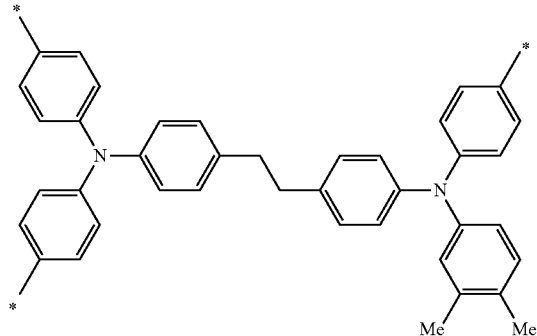

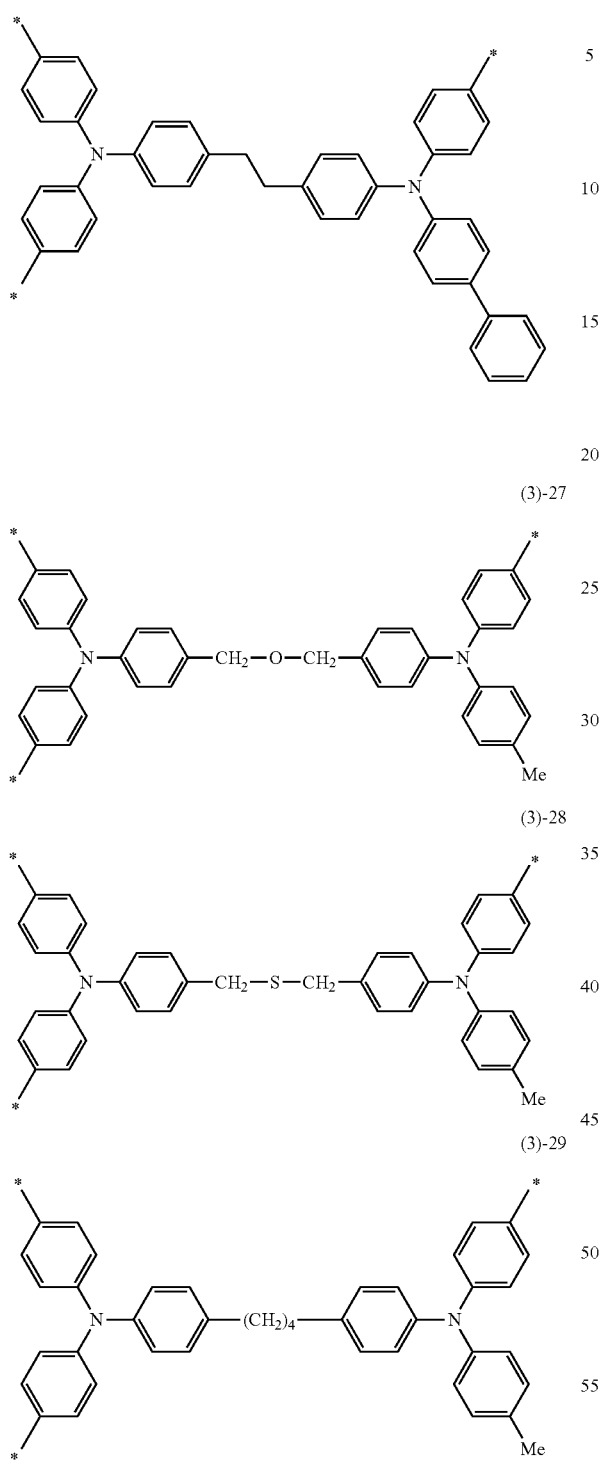
(3)-26
(3)-27
(3)-28
(3)-29
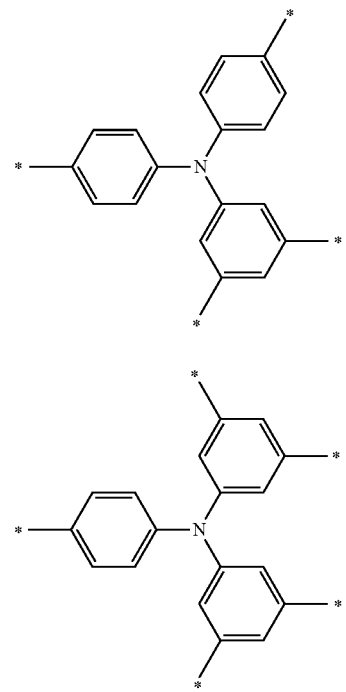
(4)-1
(4)-2
(4)-3
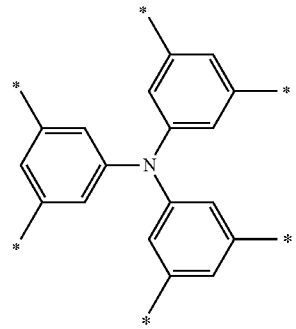
(4)-4
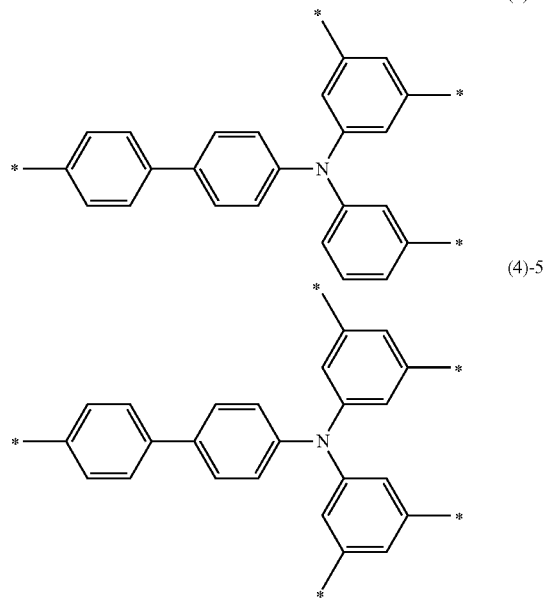
(4)-5
Next, as specific examples of the charge transporting skeleton F in a case where the total number of D in General Formulae (I) and (I') is 4, "(4)-1" to "(4)-31" will be shown. However, the exemplary embodiment is not limited to the examples. In addition, a portion * in each structural formula shows that this portion is linked to D in General Formulae (I) and (I').

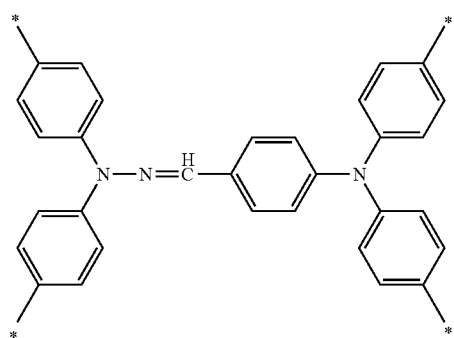
(4)-6
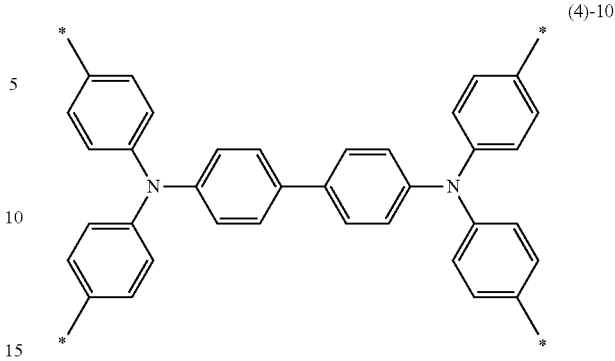
(4)-10
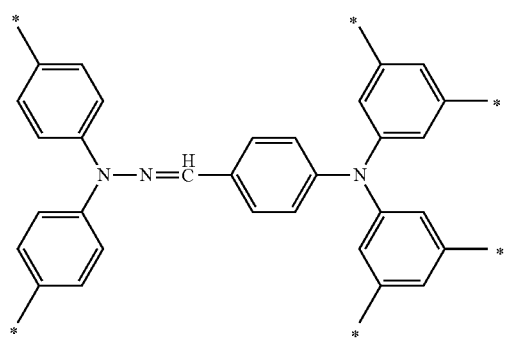
(4)-7
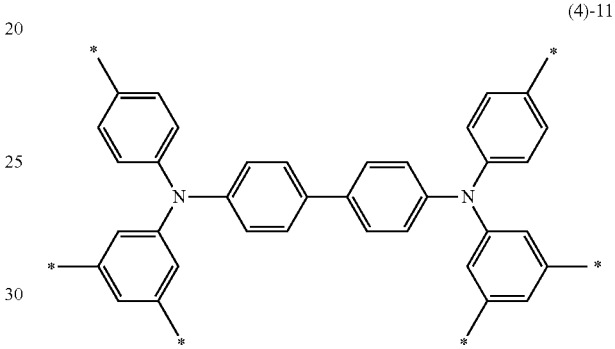
(4)-11
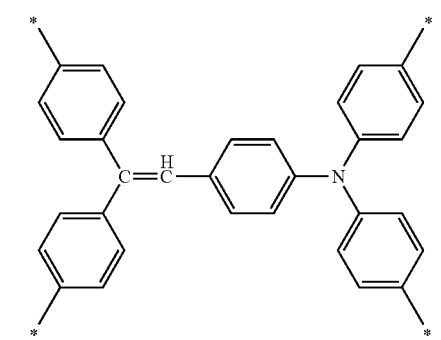
(4)-8
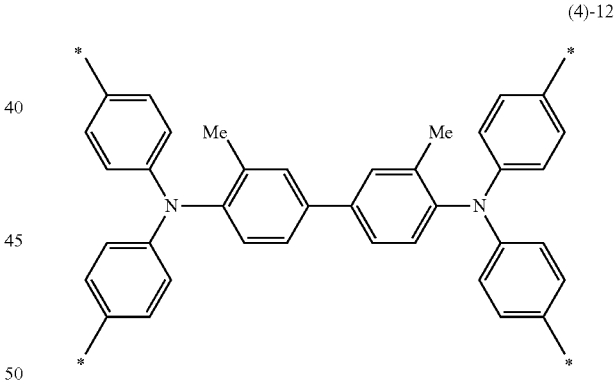
(4)-12
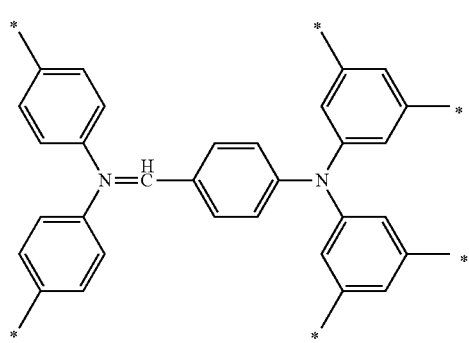
(4)-9
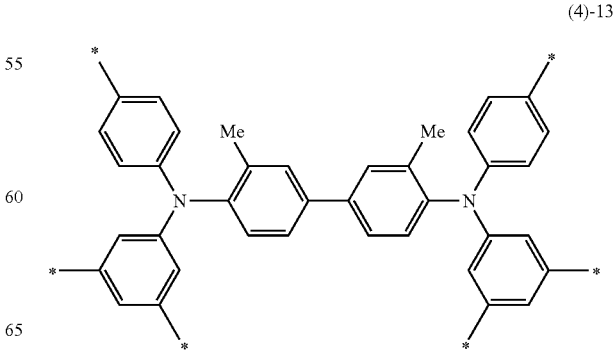
(4)-13

(4)-14
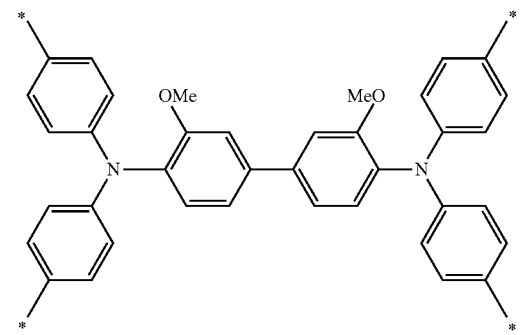
(4)-15
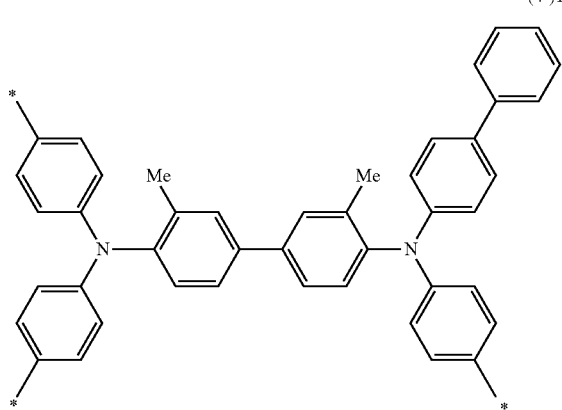
(4)-16
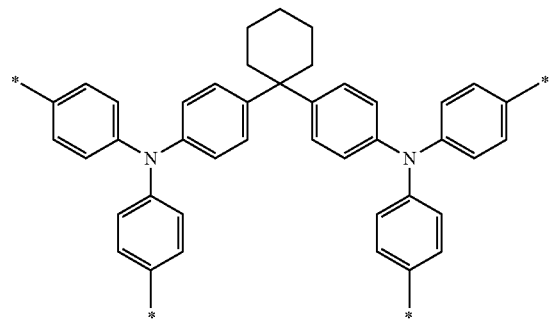
(4)-17
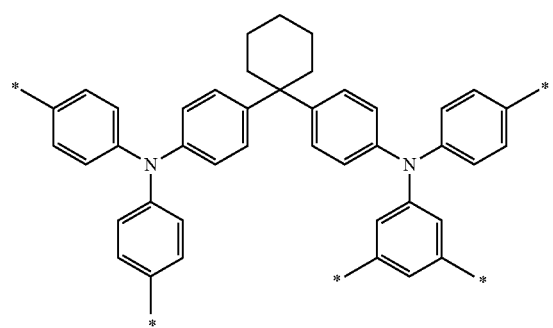
(4)-18
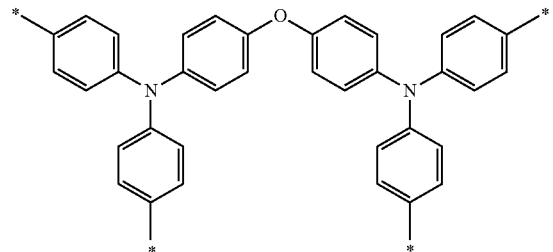
(4)-19
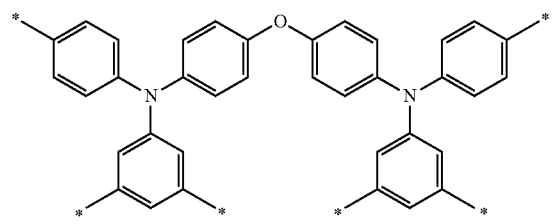
(4)-20
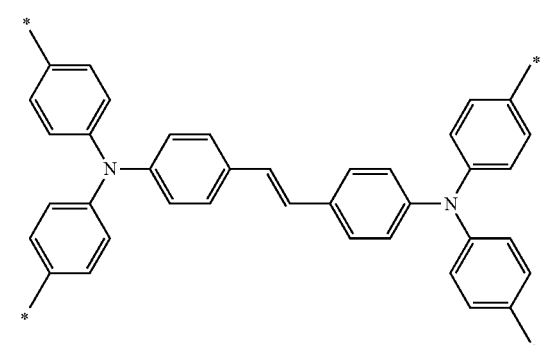
(4)-21
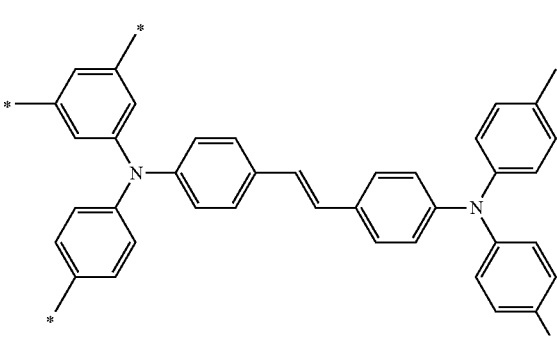
(4)-22
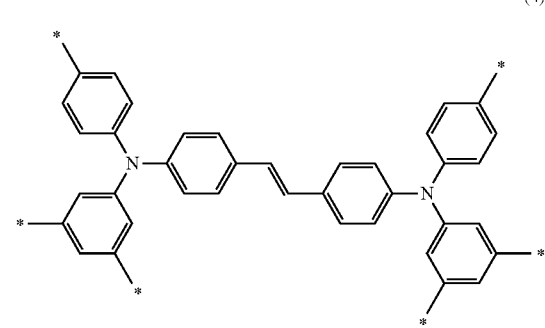

(4)-23
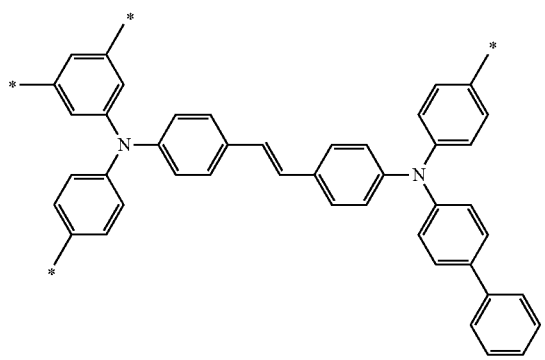
(4)-24
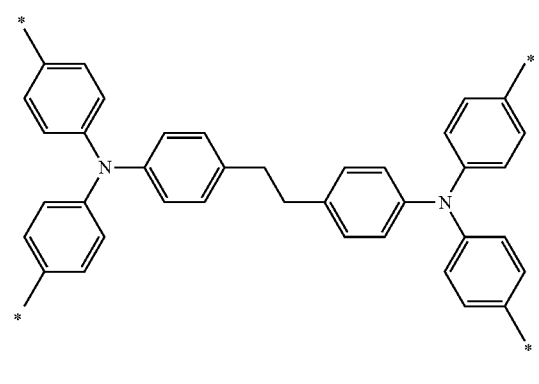
(4)-25
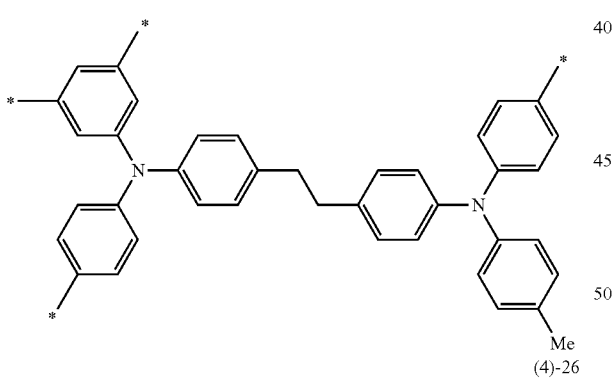
(4)-26
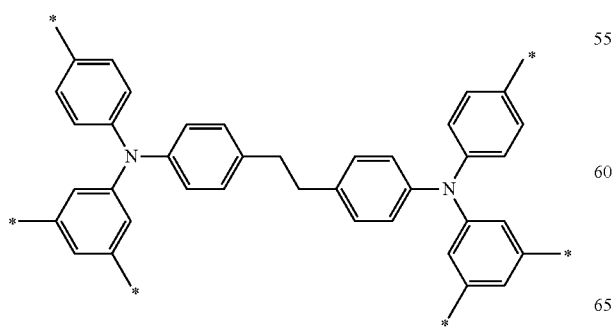
(4)-27
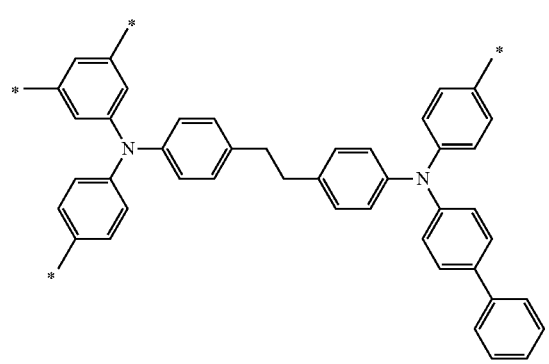
(4)-28
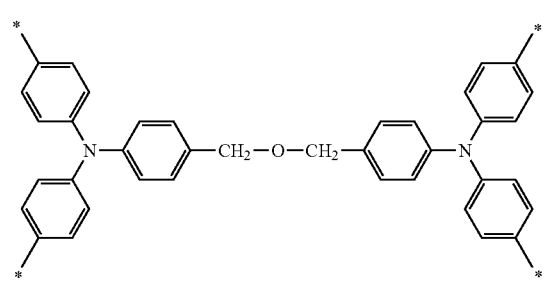
(4)-29
(4)-30
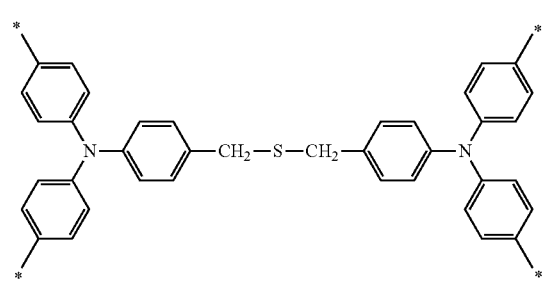

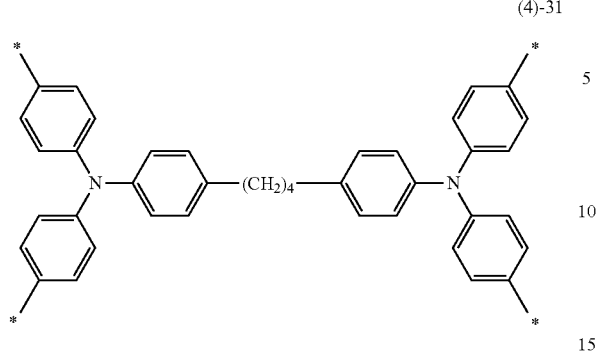

(4)-31

Next, as specific examples of D in General Formula (I) or (II), that is, specific examples the group represented by Formula (III), "(III)-1 to (III)-11" will be shown. A portion * in each structural formula shows that this portion is linked to the charge transporting skeleton F in General Formula (I) or to $Ar^1$ to $Ar^5$ in General Formula (II).

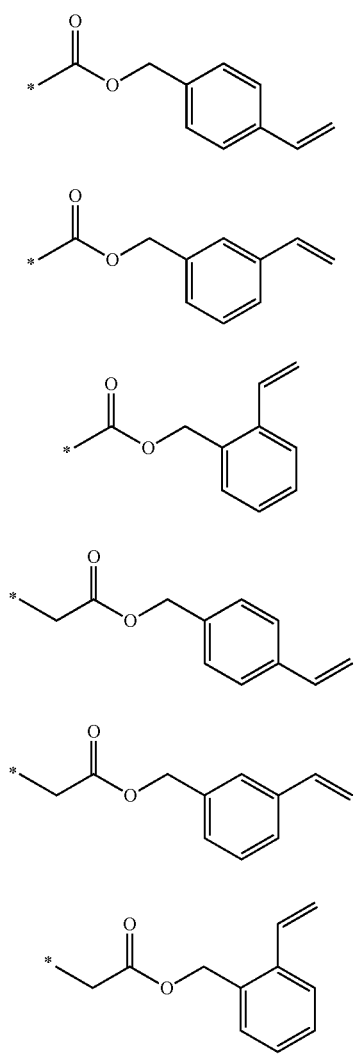

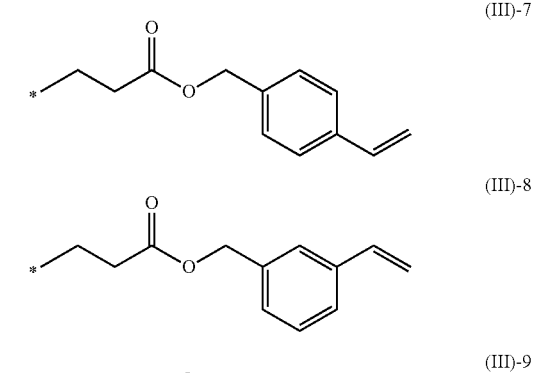

Next, as specific examples of D in General Formula (I) or (II'), that is, specific examples of the group represented by Formula (III'), "(III')-1 to (III')-66" will be shown. A portion * in each structural formula shows that this portion is linked to the charge transporting skeleton F in General Formula (I') or to $Ar^1$ to $Ar^5$ in General Formula (II').

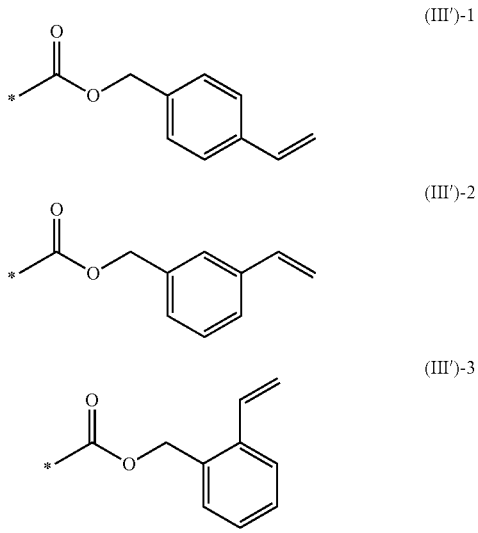

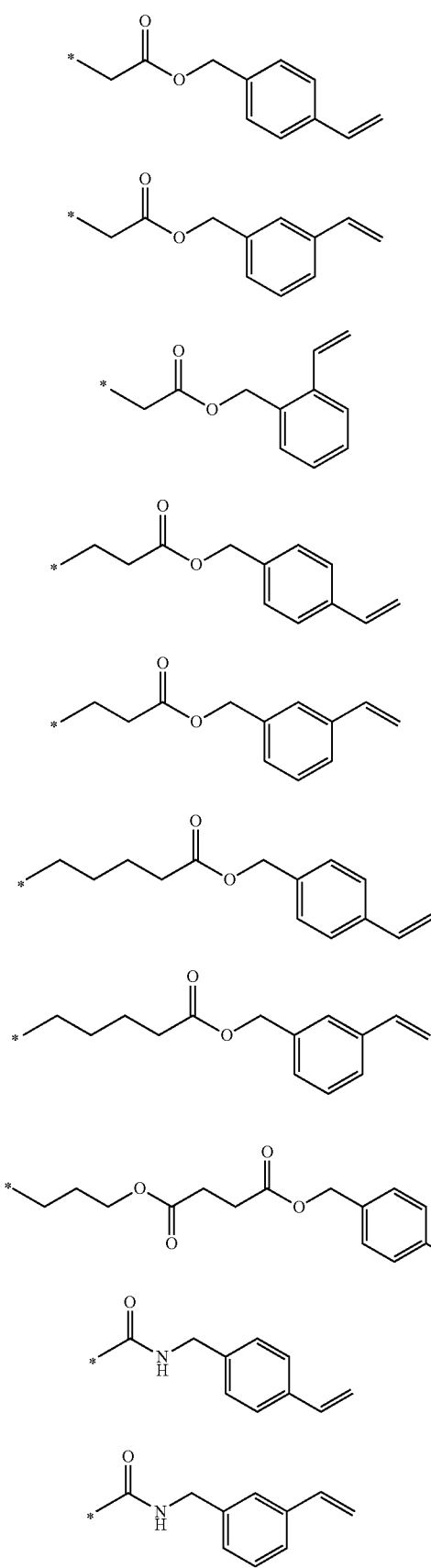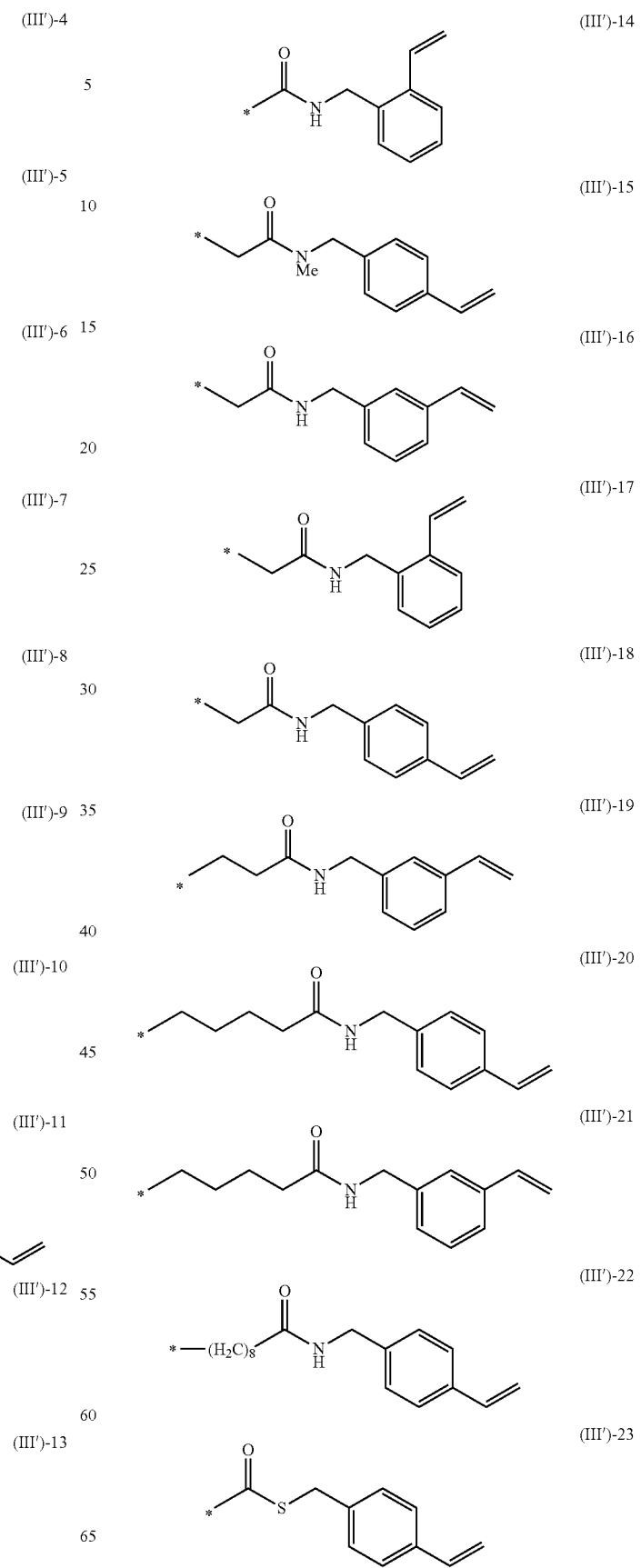

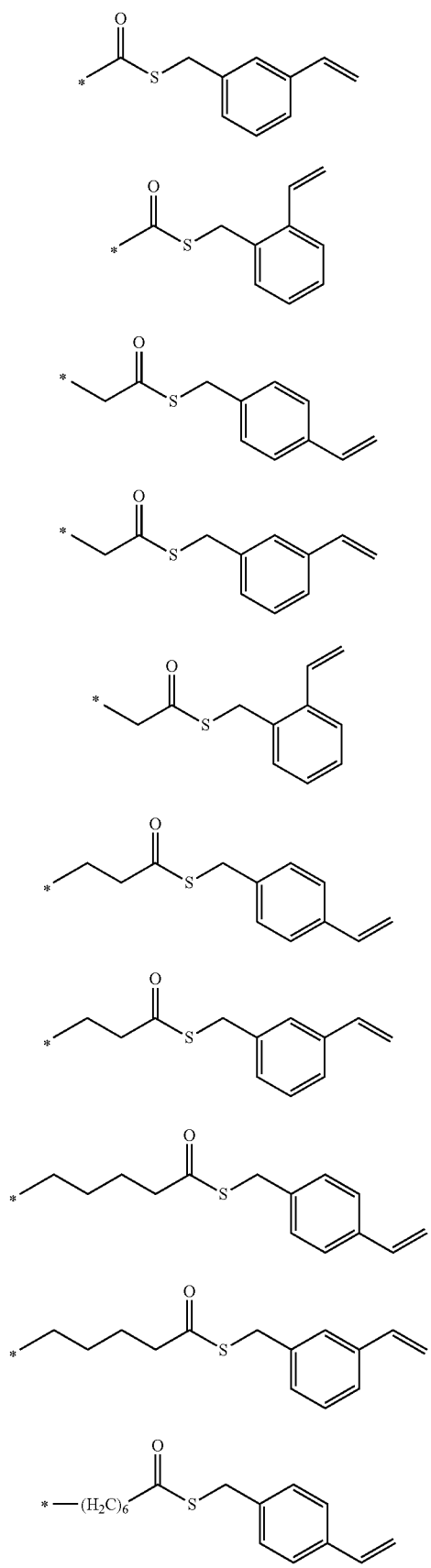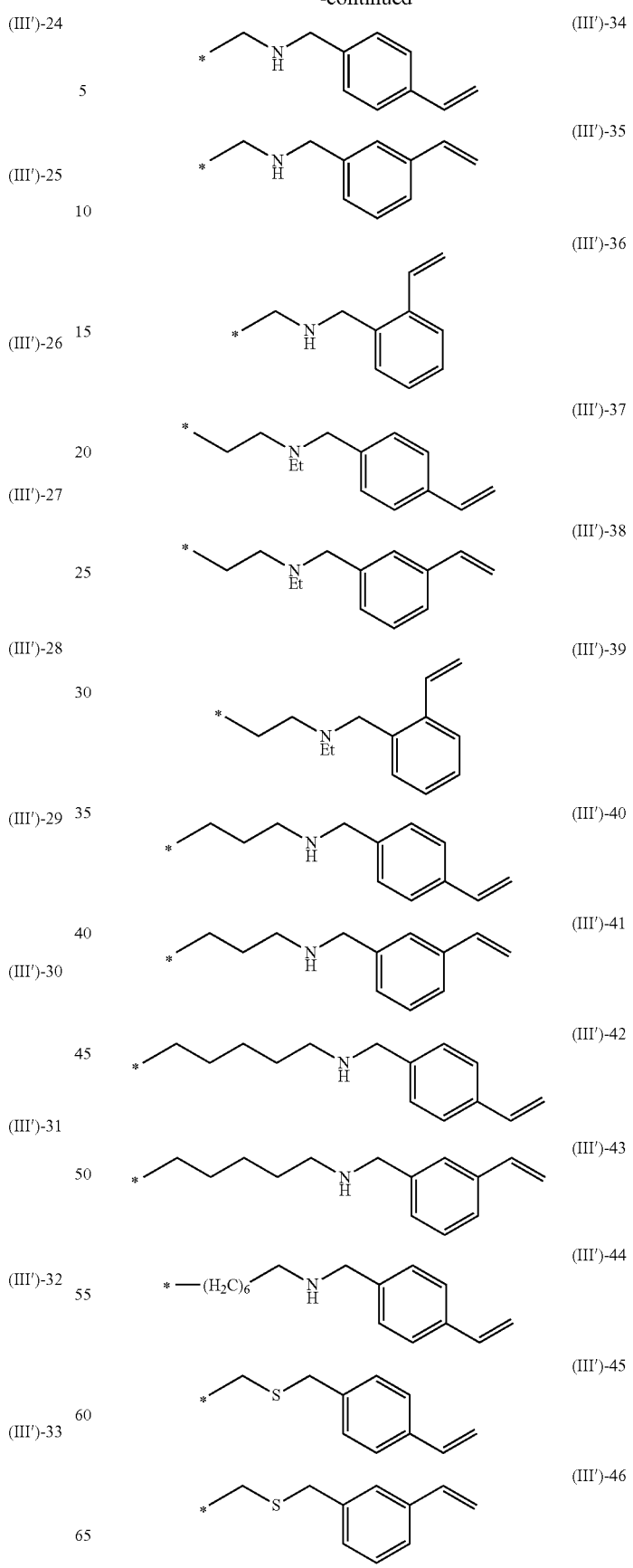

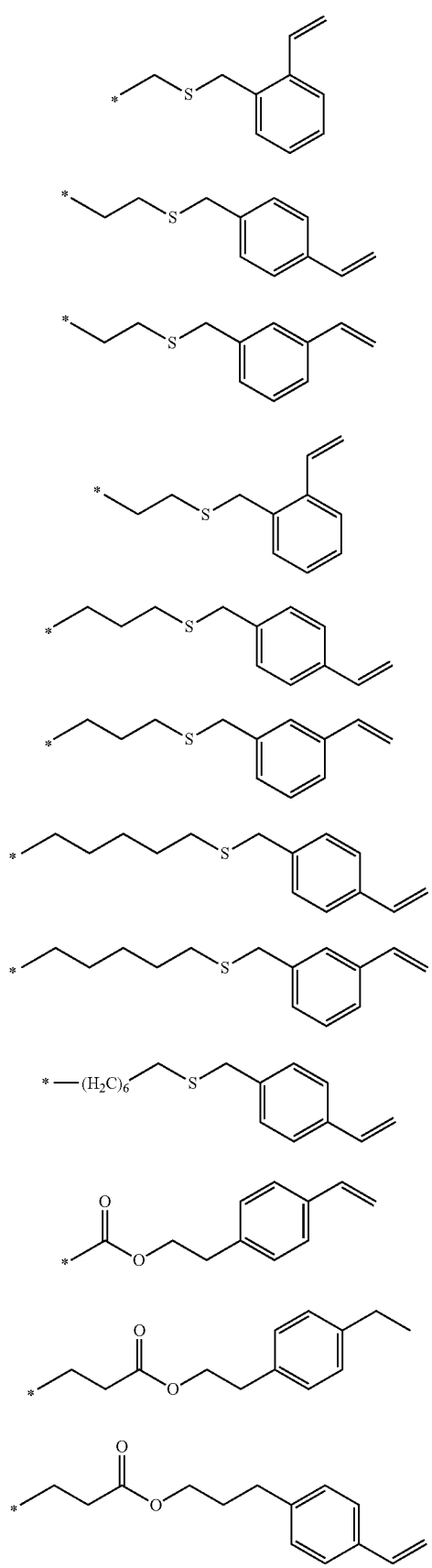
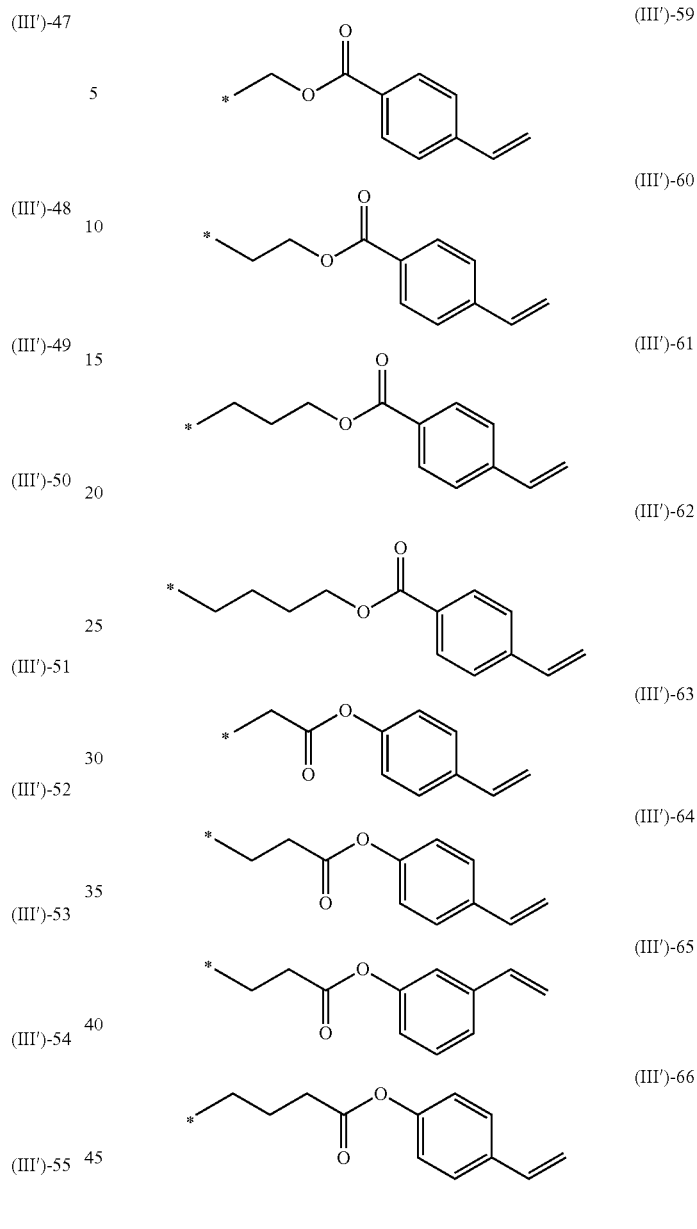

Next, as specific examples of the reactive compound represented by General Formula (I), "(I)-1" to "(I)-60" will be shown below, but the exemplary embodiment is not limited to the examples. In addition, the CTM skeleton structure in the following tables corresponds to the charge transporting skeleton F in General Formula (I).

TABLE 1

| Compound | CTM skeleton structure | General Formula (III) structure |
|---|---|---|
| (I)-1 | (1)-1 | (III)-1 |
| (I)-2 | (1)-1 | (III)-2 |
| (I)-3 | (1)-1 | (III)-4 |
| (I)-4 | (1)-2 | (III)-5 |
| (I)-5 | (1)-2 | (III)-7 |
| (I)-6 | (1)-4 | (III)-3 |
| (I)-7 | (1)-4 | (III)-7 |
| (I)-8 | (1)-7 | (III)-6 |
| (I)-9 | (1)-11 | (III)-4 |

TABLE 1-continued

| Compound | CTM skeleton structure | General Formula (III) structure |
|---|---|---|
| (I)-10 | (1)-15 | (III)-5 |
| (I)-11 | (1)-25 | (III)-1 |
| (I)-12 | (1)-22 | (III)-1 |
| (I)-13 | (2)-2 | (III)-1 |
| (I)-14 | (2)-2 | (III)-3 |
| (I)-15 | (2)-2 | (III)-7 |
| (I)-16 | (2)-3 | (III)-4 |
| (I)-17 | (2)-3 | (III)-7 |
| (I)-18 | (2)-5 | (III)-6 |
| (I)-19 | (2)-10 | (III)-4 |
| (I)-20 | (2)-10 | (III)-5 |
| (I)-21 | (2)-13 | (III)-1 |
| (I)-22 | (2)-13 | (III)-3 |
| (I)-23 | (2)-13 | (III)-7 |
| (I)-24 | (2)-16 | (III)-5 |
| (I)-25 | (2)-23 | (III)-7 |
| (I)-26 | (2)-23 | (III)-4 |
| (I)-27 | (2)-25 | (III)-7 |
| (I)-28 | (2)-25 | (III)-4 |
| (I)-29 | (2)-26 | (III)-5 |
| (I)-30 | (2)-26 | (III)-7 |

TABLE 2

| Compound | CTM skeleton structure | General Formula (III) structure |
|---|---|---|
| (I)-31 | (3)-1 | (III)-2 |
| (I)-32 | (3)-1 | (III)-7 |
| (I)-33 | (3)-5 | (III)-2 |
| (I)-34 | (3)-7 | (III)-4 |

TABLE 2-continued

| Compound | CTM skeleton structure | General Formula (III) structure |
|---|---|---|
| (I)-35 | (3)-7 | (III)-2 |
| (I)-36 | (3)-19 | (III)-4 |
| (I)-37 | (3)-26 | (III)-1 |
| (I)-38 | (3)-26 | (III)-3 |
| (I)-39 | (4)-3 | (III)-3 |
| (I)-40 | (4)-3 | (III)-4 |
| (I)-41 | (4)-8 | (III)-5 |
| (I)-42 | (4)-8 | (III)-6 |
| (I)-43 | (4)-12 | (III)-7 |
| (I)-44 | (4)-12 | (III)-4 |
| (I)-45 | (4)-12 | (III)-2 |
| (I)-46 | (4)-12 | (III)-11 |
| (I)-47 | (4)-16 | (III)-3 |
| (I)-48 | (4)-16 | (III)-4 |
| (I)-49 | (4)-20 | (III)-1 |
| (I)-50 | (4)-20 | (III)-4 |
| (I)-51 | (4)-20 | (III)-7 |
| (I)-52 | (4)-24 | (III)-4 |
| (I)-53 | (4)-24 | (III)-7 |
| (I)-54 | (4)-24 | (III)-3 |
| (I)-55 | (4)-24 | (III)-4 |
| (I)-56 | (4)-25 | (III)-1 |
| (I)-57 | (4)-26 | (III)-3 |
| (I)-58 | (4)-28 | (III)-4 |
| (I)-59 | (4)-28 | (III)-5 |
| (I)-60 | (4)-28 | (III)-6 |
| (I)-61 | (4)-12 | (III)-8 |

Next, an example of a synthesis pathway of the reactive compound of the exemplary embodiment will be shown below.

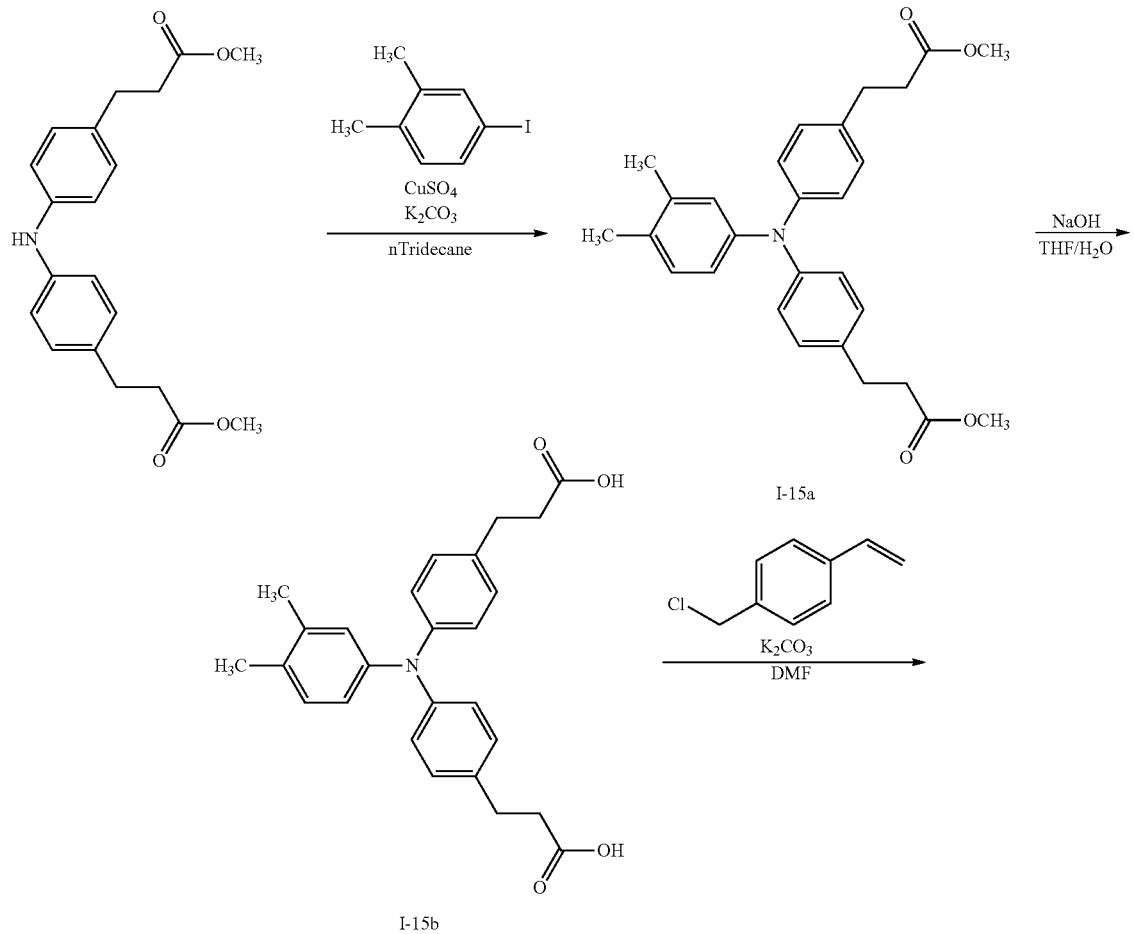

-continued
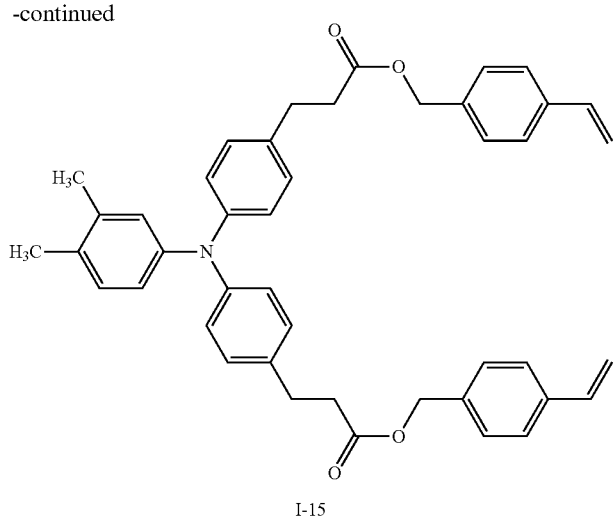
I-15
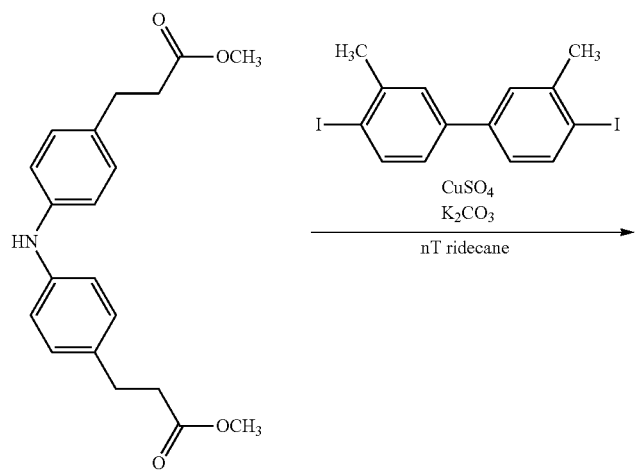
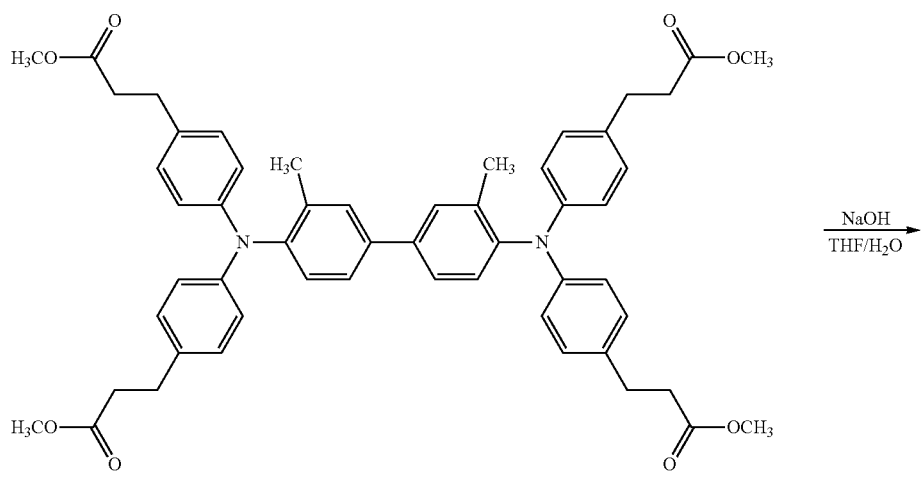
I-43a

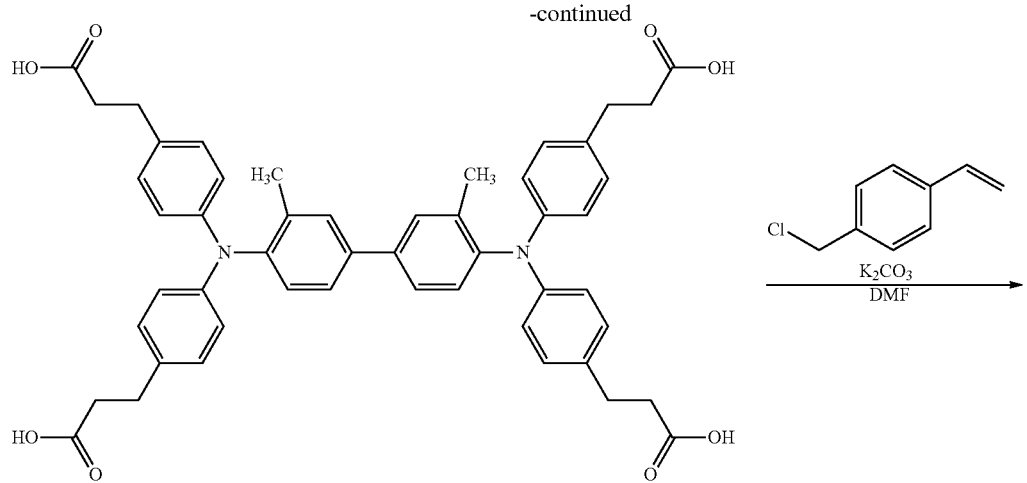

I-43b

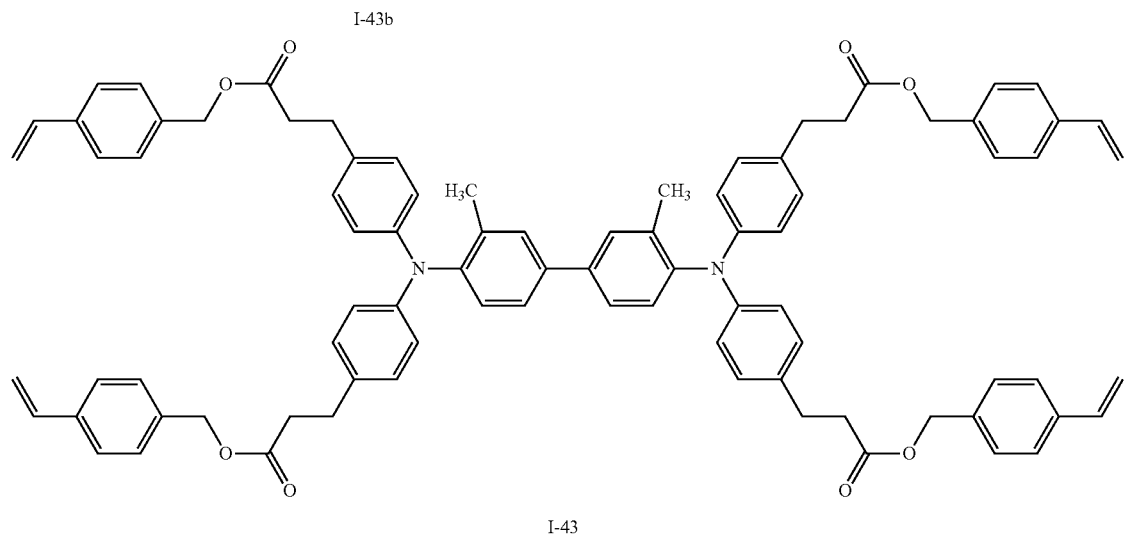

I-43

Next, specific examples of the novel reactive compound represented by General Formula (I') will be shown below, but the exemplary embodiment is not limited to the examples.

The "CTM skeleton structure" in the following tables corresponds to the charge transporting skeleton F in General Formula (I')

TABLE 3

| Compound | CTM skeleton structure | General Formula (III') structure |
|---|---|---|
| (I')-1 | (1)-1 | (III')-1 |
| (I')-2 | (1)-1 | (III')-2 |
| (I')-3 | (1)-1 | (III')-4 |
| (I')-4 | (1)-2 | (III')-5 |
| (I')-5 | (1)-2 | (III')-7 |
| (I')-6 | (1)-4 | (III')-3 |
| (I')-7 | (1)-4 | (III')-7 |
| (I')-8 | (1)-7 | (III')-6 |
| (I')-9 | (1)-11 | (III')-4 |
| (I')-10 | (1)-15 | (III')-5 |
| (I')-11 | (1)-25 | (III')-1 |
| (I')-12 | (1)-22 | (III')-1 |
| (I')-13 | (2)-2 | (III')-1 |
| (I')-14 | (2)-2 | (III')-3 |
| (I')-15 | (2)-2 | (III')-7 |
| (I')-16 | (2)-3 | (III')-4 |
| (I')-17 | (2)-3 | (III')-7 |

TABLE 3-continued

| Compound | CTM skeleton structure | General Formula (III') structure |
|---|---|---|
| (I')-18 | (2)-5 | (III')-6 |
| (I')-19 | (2)-10 | (III')-4 |
| (I')-20 | (2)-10 | (III')-5 |
| (I')-21 | (2)-13 | (III')-1 |
| (I')-22 | (2)-13 | (III')-3 |
| (I')-23 | (2)-13 | (III')-7 |
| (I')-24 | (2)-16 | (III')-5 |
| (I')-25 | (2)-23 | (III')-7 |
| (I')-26 | (2)-23 | (III')-4 |
| (I')-27 | (2)-25 | (III')-7 |
| (I')-28 | (2)-25 | (III')-4 |
| (I')-29 | (2)-26 | (III')-5 |
| (I')-30 | (2)-26 | (III')-7 |

TABLE 4

| Compound | CTM skeleton structure | General Formula (III') structure |
|---|---|---|
| (I')-31 | (3)-1 | (III')-2 |
| (I')-32 | (3)-1 | (III')-7 |
| (I')-33 | (3)-5 | (III')-2 |
| (I')-34 | (3)-7 | (III')-4 |

TABLE 4-continued

| Compound | CTM skeleton structure | General Formula (III') structure |
|---|---|---|
| (I')-35 | (3)-7 | (III')-2 |
| (I')-36 | (3)-19 | (III')-4 |
| (I')-37 | (3)-26 | (III')-1 |
| (I')-38 | (3)-26 | (III')-3 |
| (I')-39 | (4)-3 | (III')-3 |
| (I')-40 | (4)-3 | (III')-4 |
| (I')-41 | (4)-8 | (III')-5 |
| (I')-42 | (4)-8 | (III')-6 |
| (I')-43 | (4)-12 | (III')-7 |
| (I')-44 | (4)-12 | (III')-4 |
| (I')-45 | (4)-12 | (III')-2 |
| (I')-46 | (4)-12 | (III')-11 |
| (I')-47 | (4)-16 | (III')-3 |
| (I')-48 | (4)-16 | (III')-4 |
| (I')-49 | (4)-20 | (III')-1 |
| (I')-50 | (4)-20 | (III')-4 |
| (I')-51 | (4)-20 | (III')-7 |
| (I')-52 | (4)-24 | (III')-4 |
| (I')-53 | (4)-24 | (III')-7 |
| (I')-54 | (4)-24 | (III')-3 |
| (I')-55 | (4)-24 | (III')-4 |
| (I')-56 | (4)-25 | (III')-1 |
| (I')-57 | (4)-26 | (III')-3 |
| (I')-58 | (4)-28 | (III')-4 |
| (I')-59 | (4)-28 | (III')-5 |
| (I')-60 | (4)-28 | (III')-6 |

TABLE 5

| Compound | CTM skeleton structure | General Formula (III') structure |
|---|---|---|
| (I')-61 | (1)-1 | (III')-15 |
| (I')-62 | (1)-1 | (III')-27 |
| (I')-63 | (1)-1 | (III')-37 |
| (I')-64 | (1)-2 | (III')-52 |
| (I')-65 | (1)-2 | (III')-18 |
| (I')-66 | (1)-4 | (III')-31 |
| (I')-67 | (1)-4 | (III')-44 |
| (I')-68 | (1)-7 | (III')-45 |
| (I')-69 | (1)-11 | (III')-45 |
| (I')-70 | (1)-15 | (III')-45 |
| (I')-71 | (1)-25 | (III')-15 |
| (I')-72 | (1)-22 | (III')-15 |
| (I')-73 | (2)-2 | (III')-15 |
| (I')-74 | (2)-2 | (III')-27 |
| (I')-75 | (2)-2 | (III')-37 |
| (I')-76 | (2)-3 | (III')-52 |
| (I')-77 | (2)-3 | (III')-18 |
| (I')-78 | (2)-5 | (III')-31 |
| (I')-79 | (2)-10 | (III')-44 |
| (I')-80 | (2)-10 | (III')-45 |
| (I')-81 | (2)-13 | (III')-45 |
| (I')-82 | (2)-13 | (III')-45 |
| (I')-83 | (2)-13 | (III')-15 |
| (I')-84 | (2)-16 | (III')-15 |

TABLE 5-continued

| Compound | CTM skeleton structure | General Formula (III') structure |
|---|---|---|
| (I')-85 | (2)-23 | (III')-27 |
| (I')-86 | (2)-23 | (III')-37 |
| (I')-87 | (2)-25 | (III')-52 |
| (I')-88 | (2)-25 | (III')-18 |
| (I')-89 | (2)-26 | (III')-31 |
| (I')-90 | (2)-26 | (III')-44 |

TABLE 6

| Compound | CTM skeleton structure | General Formula (III') structure |
|---|---|---|
| (I')-91 | (3)-1 | (III')-15 |
| (I')-92 | (3)-1 | (III')-27 |
| (I')-93 | (3)-5 | (III')-37 |
| (I')-94 | (3)-7 | (III')-52 |
| (I')-95 | (3)-7 | (III')-18 |
| (I')-96 | (3)-19 | (III')-31 |
| (I')-97 | (3)-26 | (III')-44 |
| (I')-98 | (3)-26 | (III')-45 |
| (I')-99 | (4)-3 | (III')-45 |
| (I')-100 | (4)-3 | (III')-45 |
| (I')-101 | (4)-8 | (III')-15 |
| (I')-102 | (4)-8 | (III')-15 |
| (I')-103 | (4)-12 | (III')-15 |
| (I')-104 | (4)-12 | (III')-27 |
| (I')-105 | (4)-12 | (III')-37 |
| (I')-106 | (4)-12 | (III')-52 |
| (I')-107 | (4)-16 | (III')-18 |
| (I')-108 | (4)-16 | (III')-31 |
| (I')-109 | (4)-20 | (III')-44 |
| (I')-110 | (4)-20 | (III')-45 |
| (I')-111 | (4)-20 | (III')-45 |
| (I')-112 | (4)-24 | (III')-45 |
| (I')-113 | (4)-24 | (III')-15 |
| (I')-114 | (4)-24 | (III')-15 |
| (I')-115 | (4)-24 | (III')-27 |
| (I')-116 | (4)-25 | (III')-37 |
| (I')-117 | (4)-26 | (III')-52 |
| (I')-118 | (4)-28 | (III')-18 |
| (I')-119 | (4)-28 | (III')-31 |
| (I')-120 | (4)-28 | (III')-44 |
| (I')-121 | (4)-12 | (III')-8 |
| (I')-122 | (4)-12 | (III')-64 |
| (I')-123 | (4)-12 | (III')-1 |
| (I')-124 | (4)-24 | (III')-18 |
| (I')-125 | (4)-24 | (III')-29 |
| (I')-126 | (4)-24 | (III')-40 |
| (I')-127 | (4)-24 | (III')-51 |

An example of a synthesis pathway of the charge transport material (A2) used in the exemplary embodiment will be shown below.

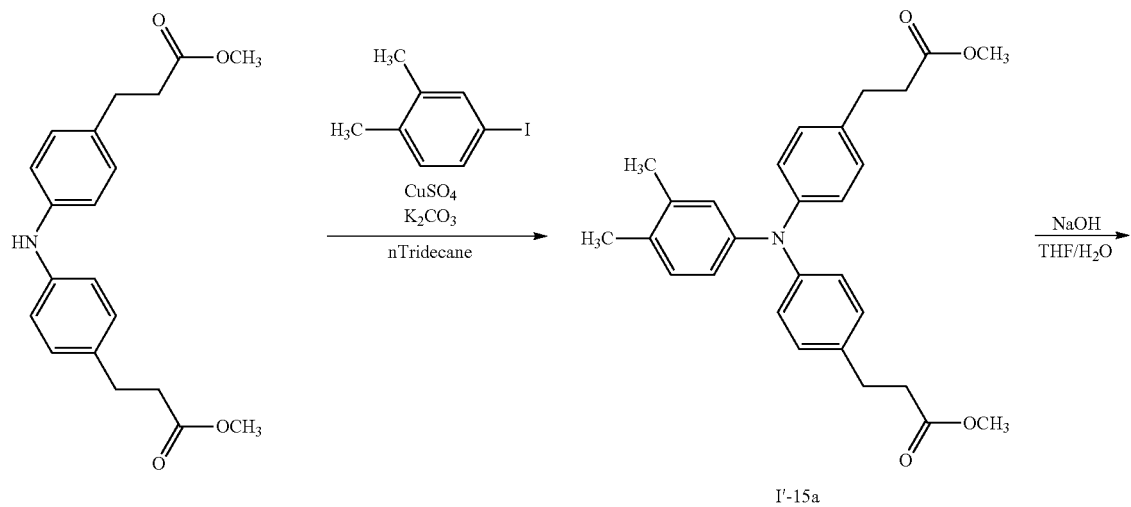
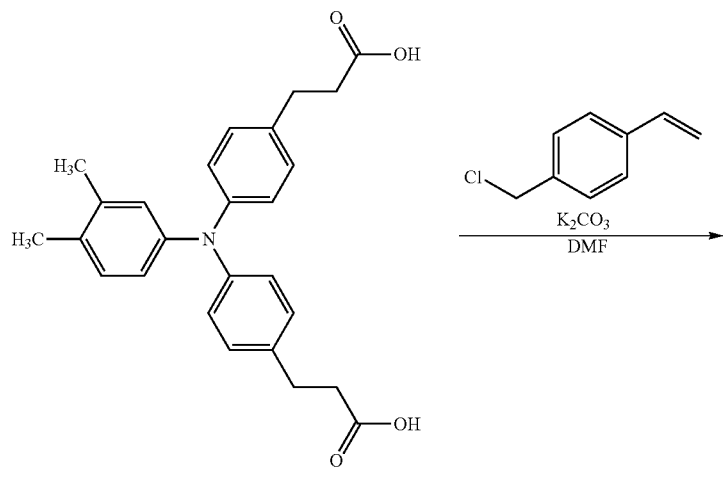
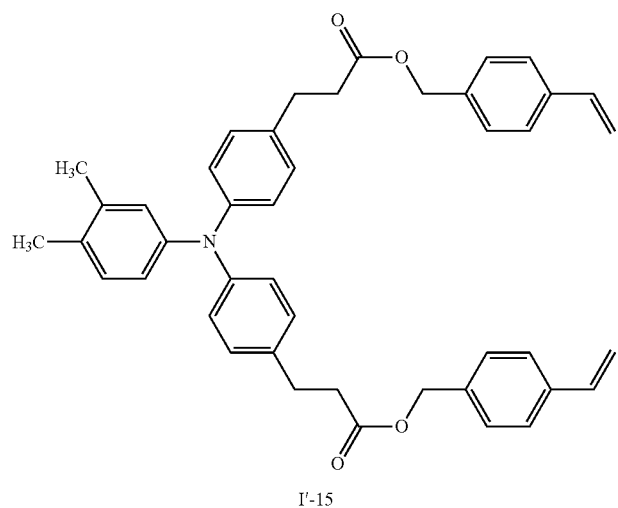

-continued
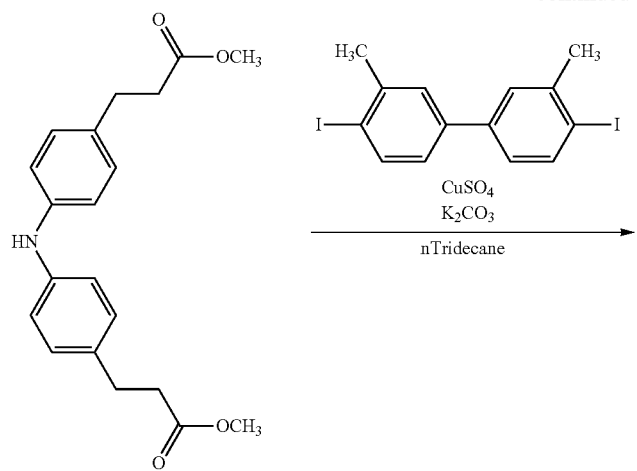
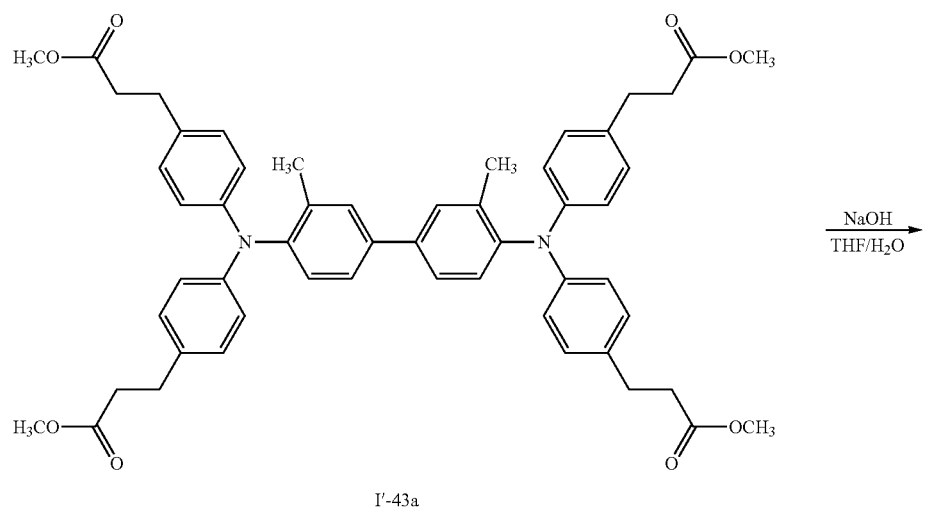
I'-43a
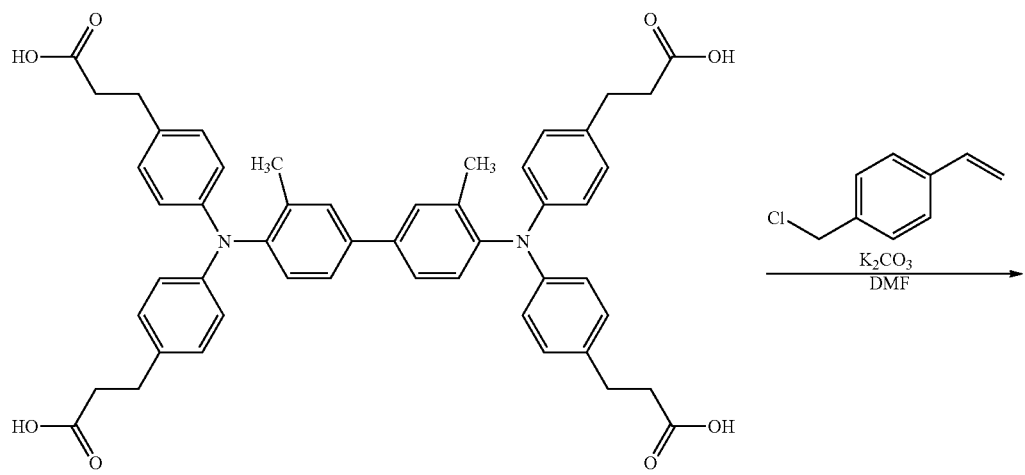
I'-43b

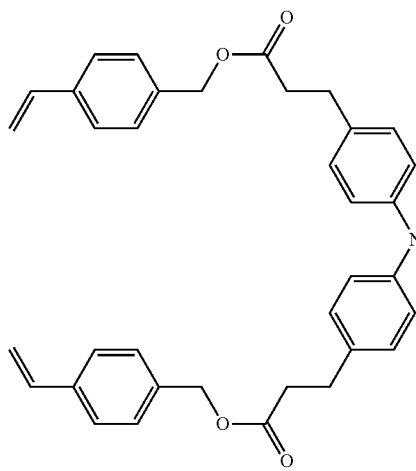 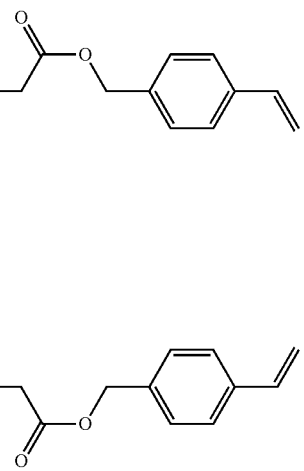

I'-43

For the composition for forming the charge transporting layer 2B-2, two or more kinds of the charge transport material (A1) or (A2) of the exemplary embodiment may be used. For example, among the charge transport material (A1) or (A2), a compound having 4 or more styrene skeletons in total in a molecule and a compound having from 1 to 3 styrene skeletons in total in a molecule are concurrently used, the strength of a polymerized or cured film may be adjusted without deteriorating charge transport performance. In this case, among the charge transport material (A1) or (A2) of the exemplary embodiment, the compound having 4 or more styrene skeletons in total in a molecule is contained desirably at 5% by weight or more, and more desirably at 20% or more, based on the total content of the charge transport material (A1) or (A2) of the exemplary embodiment.

The content of the charge transport material (A1) or (A2) of the exemplary embodiment is desirably 40% by weight or more, more desirably 50% by weight or more, and even more desirably 60% by weight or more, based on the total solid content amount of the composition for forming the charge transporting layer 2B-2.

Next, among components that constitute the composition for forming the charge transporting layer 2B-2, components other than the charge transport material (A1) or (A2) of the exemplary embodiment will be described.

The composition for forming the charge transporting layer 2B-2 may contain a charge transport agent (B) having a chain-polymerizable functional group, other than the charge transport material (A1) or (A2) of the exemplary embodiment. Examples of the charge transport agent (B) include compounds disclosed Paragraphs [0060] to [0099] in JP-A-2000-206715, compounds disclosed in Paragraphs [0066] to [0080] in JP-A-2011-70023, and the like. The content of the charge transport agent (B) is generally from 0% by weight to 40% by weight, desirably from 0% by weight to 30% by weight, and more desirably from 0% by weight to 20% by weight, based on the total solid content amount of the composition for forming the charge transporting layer 2B-2.

The composition for forming the charge transporting layer 2B-2 may contain the charge transport material and binder resin that were exemplified in the description for the charge transporting layer 2B-1. The content of the charge transport material and binder resin is generally from 0% by weight to 40% by weight, desirably from 0% by weight to 30% by weight, and more desirably from 0% by weight to 20% by weight, based on the total solid content amount of the composition for forming the charge transporting layer 2B-2.

The composition for forming the charge transporting layer 2B-2 may contain the following surfactant, in view of securing film formability.

The surfactant includes one or more structures among (A) a structure formed by polymerizing acrylic monomers having a fluorine atom, (B) a structure having a carbon-carbon double bond and a fluorine atom, (C) an alkylene oxide structure, and (D) a structure having a carbon-carbon triple bond and a hydroxyl group, in a molecule.

This surfactant may contain one or two or more structures among structures (A) to (D), in a molecule.

Hereinafter, the structures (A) to (D) and the surfactants having these structures will be described.

(A) Structure Formed by Polymerizing Acrylic Monomers Having a Fluorine Atom

Though not particularly limited, the (A) structure formed by polymerizing acrylic monomers having a fluorine atom is desirably a structure formed by polymerizing acrylic monomers having a fluoroalkyl group, and more desirably a structure formed by polymerizing acrylic monomers having a perfluoroalkyl group.

Specific examples of the surfactant having the (A) structure include Polyflow KL-600 (manufactured by Kyoeisha Chemical Co., Ltd), Eftop EF-351, Eftop EF-352, Eftop EF-801, Eftop EF-802, and Eftop EF-601 (manufactured by JEMCO, Inc.), and the like.

(B) Structure Having Carbon-Carbon Double Bond and Fluorine Atom

Though not particularly limited, the (B) structure having a carbon-carbon double bond and a fluorine atom is desirably a group represented by at least any one of the following Structural Formulae (B1) and (B2).

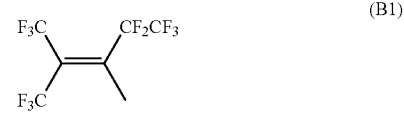

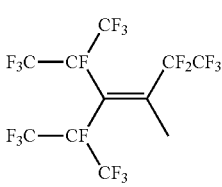
(B2)

The surfactant having the (B) structure is desirably a compound having a group represented by at least any one of the Structural Formulae (B1) and (B2) in a. side chain of an acrylic polymer, or a compound represented by any one of the following Structural Formulae (B3) to (B5).

When the surfactant having the (B) structure is a compound having at least any one of the Structural Formulae (B1) and (B2) in a side chain of an acrylic polymer, the acrylic structure is easily mixed with other components in the composition, and accordingly, an almost uniform uppermost surface layer may be formed.

When the surfactant having the (B) structure is a compound represented by any one of Structural Formulae (B3) to (B5), cissing caused during coating tends to be prevented, and accordingly, defects in a coating film may be inhibited.

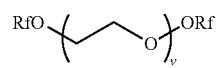
(B3)

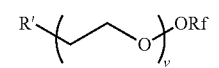
(B4)

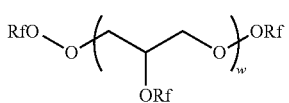
(B5)

In the Structural Formulae (B3) to (B5), each of v and w independently represents an integer of 1 or greater, R' represents a hydrogen atom or a monovalent organic group, and each Rf independently represents a group represented by Structural Formula (B1) or (B2).

In Structural Formulae (B3) to (B5), examples of the monovalent organic group represented by R' include an alkyl group having from 1 to 30 carbon atoms and a hydroxyalkyl group having from 1 to 30 carbon atoms.

Examples of commercially available products of the surfactant having the (B) structure include the following ones.

Examples of the compound represented by any one of the Structural Formulae (B3) to (B5) includes Ftergent 100, Ftergent 100C, Ftergent 110, Ftergent 140A, Ftergent 150, Ftergent 150CH, Ftergent A-K, Ftergent 501, Ftergent 250, Ftergent 251, Ftergent 222F, Ftergent FTX-218, Ftergent 300, Ftergent 310, Ftergent 400SW, Ftergent 212M, Ftergent 245M, Ftergent 290M, Ftergent FTX-207S, Ftergent FTX-211S, Ftergent FTX-220S, Ftergent FTX-230S, Ftergent FTX-209F, Ftergent FTX-213F, Ftergent FTX-222F, Ftergent FTX-233F, Ftergent FTX-245F, Ftergent FTX-208G, Ftergent FTX-218G, Ftergent FTX-230G, Ftergent FTX-240G, Ftergent FTX-204D, Ftergent FTX-280D, Ftergent FTX-212D, Ftergent FTX-216D, Ftergent FTX-218D, Ftergent FTX-220D, Ftergent FTX-222D (manufactured by Neos Company Limited), and the like.

Examples of the compound having at least any one of Structural Formulae (B1) and (B2) in a side chain of the acrylic polymer include KB-L82, KB-L85, KB-L97, KB-L109, KB-L110, KB-F2L, KB-F2M, KB-F2S, KB-F3M, KB-FaM (manufactured by Neos Company Limited), and the like.

(C) Alkylene Oxide Structure (C) alkylene oxide structure includes alkylene oxide and polyalkylene oxide. Specifically, alkylene oxide includes ethylene oxide, propylene oxide, and the like. The alkylene oxide structure may be polyalkylene oxide in which the repeating number of the alkylene oxide is from 2 to 10000.

Examples of the surfactant having the (C) alkylene oxide structure include polyethylene glycol, a polyether antifoam agent, polyether-modified silicone oil, and the like.

The average molecular weight of the polyethylene glycol is desirably 2000 or less, and examples of the polyethylene glycol having an average molecular weight of 2000 or less include polyethylene glycol 2000 (average molecular weight of 2000), polyethylene glycol 600 (average molecular weight of 600), polyethylene glycol 400 (average molecular weight of 400), polyethylene glycol 200 (average molecular weight of 200), and the like.

In addition, polyether antifoam agent such as PE-M and PE-L (all manufactured by Wako Pure Chemical Industries, Ltd.) and an antifoam agents No. 1 and No. 5 (all manufactured by Kao Corporation) are also exemplified as suitable examples.

Examples of the surfactant having a fluorine atom in a molecule in addition to the (C) alkylene oxide structure include a surfactant having alkylene oxide or polyalkylene oxide in a side chain of a polymer that has a fluorine atom, a surfactant in which the terminal of alkylene oxide or polyalkylene oxide is substituted with a substituent that has a fluorine atom, and the like.

Specific examples of the surfactant having a fluorine atom in a molecule in addition to the (C) alkylene oxide structure include Megafac F-443, F-444, F-445, and F-446 (all manufactured by DIC Corporation), Ftergent 250, Ftergent 251, and Ftergent 222F (all manufactured by Neos Company Limited), POLY FOX PF636, PF6320, PF6520, and PF656 (all manufactured by Kitamura Chemicals Co., Ltd.), and the like.

Specific examples of the surfactant having a silicone structure in a molecule in addition to the (C) alkylene oxide structure include KF351 (A), KF352 (A), KF353 (A), KF354 (A), KF355 (A), KF615 (A), KF618, KF945 (A), and KF6004 (all manufactured by Shin-Etsu Chemical Co., Ltd.), TSF4440, TSF4445, TSF4450, TSF4446, TSF4452, TSF4453, and TSF4460 (all manufactured by GE Toshiba Silicones, Co., Ltd.), BYK-300, 302, 306, 307, 310, 315, 320, 322, 323, 325, 330, 331, 333, 337, 341, 344, 345, 346, 347, 348, 370, 375, 377, 378, UV3500, UV3510, and UV3570 (all manufactured by BYK-Chemie Japan KK), and the like.

(D) Structure Having Carbon-Carbon Triple Bond and Hydroxyl Group (D) structure having a carbon-carbon triple bond and a hydroxyl group is not particularly limited, and examples of the surfactant having this structure include the following compounds.

Examples of the surfactant having the (D) structure including a carbon-carbon triple bond and a hydroxyl group include a compound having a triple bond and a hydroxyl group in a molecule, and specific examples thereof include 2-propyn-1-ol, 1-butyn-3-ol, 2-butyn-1-ol, 3-butyn-1-ol, 1-pentyn-3-ol, 2-pentyn-1-ol, 3-pentyn-1-ol, 4-pentyn-1-ol, 4-pentyn-2-ol, 1-hexyn-3-ol, 2-hexyn-1-ol, 3-hexyn-1-ol, 5-hexyn-1-ol, 5-hexyn-3-ol, 1-heptyn-3-ol, 2-heptyn-1-ol, 3-heptyn-1-ol, 4-heptyn-2-ol, 5-heptyn-3-ol, 1-octyn-3-ol, 3-octyn-1-ol, 3-nonyn-1-ol, 2-decyn-1-ol, 3-decyn-1-ol, 10-undecyn-1-ol, 3-methyl-1-butyn-3-ol, 3-methyl-1-penten-4-yn-3-ol, 3-methyl-1-pentyn-3-ol, 5-methyl-1-hexyn-3-ol, 3-ethyl-1-pentyn-3-ol, 3-ethyl-1-heptyn-3-ol, 4-ethyl-1-octyn-3-ol, 3,4-dimethyl-1-pentyn-3-ol, 3,5-dimethyl-1-hexyn-3-ol, 3,6-dimethyl-1-heptyn-3-ol, 2,2,8,8-tetramethyl-3,6-nonadiyn-5-ol, 4,6-nonadecadiyn-1-ol, 10,12-pentacosadiyn-1-ol, 2-butyne-1,4-diol, 3-hexyne-2,5-diol, 2,4-hexadiyne-1,6-diol, 2,5-dimethyl-3-hexyne-2,5-diol, 3,6-dimethyl-4-octyne-3,6-diol, 2,4,7,9-tetramethyl-5-decyne-4,7-diol, (+)-1,6-bis(2-chlorophenyl)-1,6-diphenyl-2,4-hexadiyne-1,6-diol, (−)-1,6-bis(2-chlorophenyl)-1,6-diphenyl-2,4-hexadiyne-1,6-diol, 2-butyne-1,4-diol bis(2-hydroxyethyl), 1,4-diacetoxy-2-butyne, 4-diethylamino-2-butyn-1-ol, 1,1-diphenyl-2-propyn-1-ol, 1-ethynyl-1-cyclohexanol, 9-ethynyl-9-fluorenol, 2,4-hexadiynediol-1,6-bis(4-phenylazobenzenesulfonate), 2-hydroxy-3-butynic acid, 2-hydroxy-3-butynic acid ethyl ester, 2-methyl-4-phenyl-3-butyn-2-ol, methyl propargyl ether, 5-phenyl-4-pentyn-1-ol, 1-phenyl-1-propyn-3-ol, 1-phenyl-2-propyn-1-ol, 4-trimethylsilyl-3-butyn-2-ol, 3-trimethylsilyl-2-propyn-1-ol, and the like.

The examples also include a compound (for example a Surfynol 400 series (manufactured by Shin-Etsu Chemical Co., Ltd.)) obtained by adding alkylene oxide such as ethylene oxide to a portion or all of hydroxyl groups in the above compound, and the like.

As the surfactant having the (D) structure including a carbon-carbon triple bond and a hydroxyl group, compounds represented by any one of the following General Formulae (D1) and (D2) are desirable.

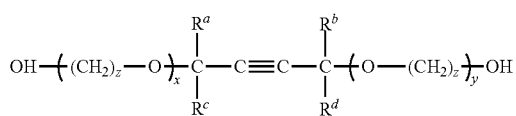

(D1)

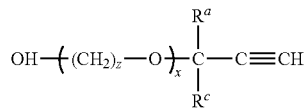

(D2)

In General Formulae (D1) and (D2), each of $R^a$, $R^b$, $R^c$, and $R^d$ independently represents a monovalent organic group, and each of x, y, and z independently represents an integer of 1 or greater.

Among the compounds represented by General Formula (D1) or (D2), compounds in which $R^a$, $R^b$, $R^c$, and $R^d$ are alkyl groups are desirable, and compounds in which at least one of $R^a$ and $R^b$ and at least one of $R^c$ and $R^d$ is a branched alkyl group are more desirable. z is desirably from 1 to 10, and each of x and y is desirably from 1 to 500.

Examples of commercially available products of the compound represented by General Formula (D1) or (D2) include a Surfynol 400 series (manufactured by Shin-Etsu Chemical Co., Ltd.).

The surfactant having the structure of (A) to (D) described above may be used alone or used as a mixture of plural kinds thereof. When the surfactant is used as a mixture of plural kinds thereof, a surfactant having a structure differing from that of the surfactant having the structure of (A) to (D) may be concurrently used, within a range that does not impair the effect of the exemplary embodiment.

Examples of the surfactant that may be concurrently used include the following surfactants having a fluorine atom and surfactants having a silicone structure.

That is, suitable examples of the surfactant that has a fluorine atom and may be concurrently used with the surfactant having the structure of (A) to (D) include perfluoroalkyl sulfonic acids (for example, perfluorobutane sulfonic acid, perfluorooctane sulfonic acid, and the like), perfluoroalkyl carboxylic acids (for example, perfluorobutane carboxylic acid, perfluorooctane carboxylic acid, and the like), and perfluoroalkyl group-containing phosphoric acid ester. The perfluoroalkyl sulfonic acids and perfluoroalkyl carboxylic acids may be a salt thereof and an amide-modified product thereof.

Examples of commercially available products of the perfluoroalkyl sulfonic acids include Megafac F-114 (manufactured by DIC Corporation), Eftop EF-101, Eftop EF-102, Eftop EF-103, Eftop EF-104, Eftop EF-105, Eftop EF-112, Eftop EF-121, Eftop EF-122A, Eftop EF-122B, Eftop EF-122C, and Eftop EF-123A (manufactured by JEMCO, Inc.), Ftergent 100, Ftergent 100C, Ftergent 110, Ftergent 140A, Ftergent 150, Ftergent 150CH, Ftergent A-K, and Ftergent 501 (manufactured by Neos Company Limited), and the like.

Examples of commercially available products of the perfluoroalkyl carboxylic acids include Megafac F-410 (manufactured by DIC Corporation), Eftop EF-201 and Eftop EF-204 (manufactured by JEMCO, Inc.), and the like.

Examples of commercially available products of the perfluoroalkyl group-containing phosphoric acid ester include Megafac F-493 and Megafac F-494 (manufactured by DIC Corporation), Eftop EF-123A, Eftop EF-123B, Eftop EF-125M, and Eftop EF-132 (manufactured by JEMCO, Inc.), and the like.

The surfactant that has a fluorine atom and may be concurrently used with the surfactant having the structure of (A) to (D) is not limited to the above-described surfactants. For example, a fluorine atom-containing compound having a betaine structure (for example, Ftergent 400SW manufactured by Neos Company Limited) and a surfactant having an amphoteric ion group (for example, Ftergent SW manufactured by Neos Company Limited) are also suitably used as the surfactant.

Examples of the surfactant that has a silicone structure and may be concurrently used with the surfactant having the structure of (A) to (D) include general silicone oil such as dimethyl silicone, methyl phenyl silicone, diphenyl silicone, or a derivative thereof.

The content of the surfactant is desirably from 0.01% by weight to 1% by weight, and more desirably from 0.02% by weight to 0.5% by weight, based on the total solid content amount of the composition for forming the charge transporting layer 2B-2. If the content of the surfactant is less than 0.01% by weight, the effect of preventing defects in coating film tends to be insufficient. If the content of the surfactant exceeds 1% by weight, the surfactant and curing components (compound represented by General Formula (I) and other monomer, oligomer, and the like) are separated from each other, and consequently, the strength of the obtained polymerized or cured film tends to be reduced.

In addition, among all surfactants, the surfactant having the structure of (A) to (D) is contained in the composition desirably at 1% by weight or more, and more desirably at 10% by weight or more.

For the purpose of controlling the viscosity of the composition and the strength, flexibility, smoothness, a cleaning property, and the like of the film, a radical-polymerizable monomer, oligomer, or the like that does not have a charge transport function may be added to the composition used for forming the charge transporting layer 2B-2.

Examples of a monofunctional radical-polymerizable monomer include isobutyl acrylate, t-butyl acrylate, isooctyl acrylate, lauryl acrylate, stearyl acrylate, isobornyl acrylate, cyclohexyl acrylate, 2-methoxyethyl acrylate, methoxy triethylene glycol acrylate, 2-ethoxyethyl acrylate, tetrahydrofurfuryl acrylate, benzyl acrylate, ethyl carbitol acrylate, phenoxyethyl acrylate, 2-hydroxy acrylate, 2-hydroxypropyl acrylate, 4-hydroxybutyl acrylate, methoxy polyethylene glycol acrylate, methoxy polyethylene glycol methacrylate, phenoxy polyethylene glycol acrylate, phenoxy polyethylene glycol methacrylate, hydroxyethyl o-phenylphenol acrylate, o-phenylphenol glycidyl ether acrylate, and the like.

Examples of a bifunctional radical-polymerizable monomer include 1,4-butanediol diacrylate, 1,6-hexanediol diacrylate, 1,9-nonanediol diacrylate, 2-n-butyl-2-ethyl-1,3-propanediol diacrylate, tripropylene glycol diacrylate, tetraethylene glycol diacrylate, dioxane glycol diacrylate, polytetramethylene glycol diacrylate, ethoxylated bisphenol A diacrylate, ethoxylated bisphenol A dimethacrylate, tricyclodecane methanol diacrylate, tricyclodecane methanol dimethacrylate, divinyl benzene, diallyl propyl isocyanurate, and the like.

Examples of a tri- or higher functional radical-polymerizable monomer include trimethylolpropane triacrylate, trimethylolpropane trimethacrylate, pentaerythritol acrylate, trimethylolpropane EO-added triacrylate, glycerin PO-added triacrylate, trisacryloyloxy ethyl phosphate, pentaerythritol tetraacrylate, ethoxylated isocyanur triacrylate, triallyl isocyanurate, trivinyl cyclohexane, trivinyl benzene, and the like.

Examples of a radical-polymerizable oligomer include oligomers based on epoxy acrylate, urethane acrylate, and polyester acrylate.

The radical-polymerizable monomer or oligomer that does not have a charge transport function is desirably contained in the composition at from 0% by weight to 50% by weight, more desirably from 0% by weight to 40% by weight, and even more desirably from 0% by weight to 30% by weight, based on the total solid content of the composition.

The cured film (crosslinked film) configuring the charge transporting layer 2B-2 is obtained by curing the composition containing the respective components through various methods such as heat, light, and electron beams. If necessary, a thermal polymerization initiator or a photopolymerization initiator may be added to the composition.

In order to keep balance between characteristics such as mechanical strength, thermal curing is desirable. Usually, when a general acrylic coating material or the like is cured, electron beams that cure the material without using a catalyst or photopolymerization that cures the material in a short time is suitably used. However, in an electrophotographic photoreceptor, since a photosensitive layer, which is the surface to be formed, of an uppermost surface layer contains photosensitive materials, it is desirable to perform thermal curing in which the reaction proceeds slowly, in order that the photosensitive materials are not easily damaged and that the surface properties of the obtained cured film are improved. Thermal curing may be performed without a catalyst, but it is desirable to use a thermal radical initiator as a catalyst.

The thermal radical initiator is not particularly limited. However, in order to inhibit the photosensitive materials in the photosensitive layer from being damaged during the formation of the charge transporting layer 2B-2, a thermal radical initiator having a 10-hour half life temperature of from 40° C. to 110° C. is desirable.

Examples of commercially available products of the thermal radical initiator include azo-based initiators such as V-30, (10-hour half life temperature: 104° C.), V-40 (10-hour half life temperature: 88° C.), V-59 (10-hour half life temperature: 67° C.), V-601 (10-hour half life temperature: 66° C.), V-65 (10-hour half life temperature: 51° C.), V-70 (10-hour half life temperature: 30° C.), VF-096 (10-hour half life temperature: 96° C.), Vam-110 (10-hour half life temperature: 111° C.), Vam-111 (10-hour half life temperature: 111° C.), VE-073 (10-hour half life temperature: 73° C.)(all manufactured by Wako Pure Chemical Industries, Ltd.), OTAZO-15 (10-hour half life temperature: 61° C.), OTAZO-30 (10-hour half life temperature: 57° C.), AIBN (10-hour half life temperature: 65° C.), AMBN (10-hour half life temperature: 67° C.), ADVN (10-hour half life temperature: 52° C.), and ACVA (10-hour half life temperature: 68° C.) (all manufactured by Otsuka Chemical Co., Ltd.); Pertetra A, Perhexa HC, Perhexa C, Perhexa V, Perhexa 22, Perhexa MC, Perbutyl H, Percumyl H, Percumyl P, Permenta H, Perocta H, Perbutyl C, Perbutyl D, Perhexyl D, Peroyl IB, Peroyl 355, Peroyl L, Peroyl SA, Nyper BW, Nyper BMT-K40/M, Peroyl IPP, Peroyl NPP, Peroyl TCP, Peroyl OPP, Peroyl SBP, Percumyl ND, Perocta ND, Perhexyl ND, Perbutyl ND, Perbutyl NHP, Perhexyl PV, Perbutyl PV, Perhexa 250, Perocta O, Perhexyl O, Perbutyl O, Perbutyl L, Perbutyl 355, Perhexyl I, Perbutyl I, Perbutyl E, Perhexa 25Z, Perbutyl A, Perhexyl Z, Perbutyl ZT, and Perbutyl Z (all manufactured by Nof Corporation); Kayaketal AM-055, Trigonox 36-C75, Laurox, Perkadox L-W75, Perkadox CH-50L, Trigonox TMBH, Kayacumene H, Kayabutyl H-70, Perkadox BC-FF, Kayahexa AD, Perkadox 14, Kayabutyl C, Kayabutyl D, Kayahexa YD-E85, Perkadox 12-XL25, Perkadox 12-EB20, Trigonox 22-N70, Trigonox 22-70E, Trigonox D-T50, Trigonox 423-C70, Kayaester CND-C70, Kayaester CND-W50, Trigonox 23-C70, Trigonox 23-W50N, Trigonox 257-C70, Kayaester P-70, Kayaester TMPO-70, Trigonox 121, Kayaester O, Kayaester HTP-65W, Kayaester AN, Trigonox 42, Trigonox F-050, Kayabutyl B, Kayacarbon EH-C70, Kayacarbon EH-W60, Kayacarbon 1-20, Kayacarbon BIC-75, Trigonox 117, and Kayalene 6-70 (manufactured by Kayaku Akzo Co., Ltd.); Luperox LP (10-hour half life temperature: 64° C.), Luperox 610 (10-hour half life temperature: 37° C.), Luperox 188 (10-hour half life temperature: 38° C.), Luperox 844 (10-hour half life temperature: 44° C.), Luperox 259 (10-hour half life temperature: 46° C.), Luperox 10 (10-hour half life temperature: 48° C.), Luperox 701 (10-hour half life temperature: 53° C.), Luperox 11 (10-hour half life temperature: 58° C.), Luperox 26 (10-hour half life temperature: 77° C.), Luperox 80 (10-hour half life temperature: 82° C.), Luperox 7 (10-hour half life temperature: 102° C.), Luperox 270 (10-hour half life temperature: 102° C.), Luperox P (10-hour half life temperature: 104° C.), Luperox 546 (10-hour half life temperature: 46° C.), Luperox 554 (10-hour half life temperature: 55° C.), Luperox 575 (10-hour half life temperature: 75° C.), Luperox TANPO (10-hour half life temperature: 96° C.), Luperox 555 (10-hour half life temperature: 100° C.), Luperox 570 (10-hour half life temperature: 96° C.), Luperox TAP (10-hour half life temperature: 100° C.), Luperox TBIC (10-hour half life temperature: 99° C.), Luperox TBEC (10-hour half life temperature: 100° C.), Luperox JW (10-hour half life temperature: 100° C.), Luperox TAIC (10-hour half life temperature: 96° C.), Luperox TAEC (10-hour half life temperature: 99° C.), Luperox DC (10-hour half life temperature: 117° C.), Luperox 101 (10-hour half life temperature: 120° C.), Luperox F (10-hour half life temperature: 116° C.), Luperox D1 (10-hour half life temperature: 129° C.), Luperox 130 (10-hour half life temperature: 131° C.), Luperox 220 (10-hour half life temperature: 107° C.), Luperox 230 (10-hour half life temperature: 109° C.), Luperox 233 (10-hour half life temperature: 114° C.), and Luperox 531 (10-hour half life temperature: 93° C.) (all manufactured by ARKEMA YOSHITOMI, LTD.); and the like.

The thermal radical initiator may be contained in the composition at from 0.001% by weight to 10% by weight, more desirably from 0.01% by weight to 5% by weight, and even more desirably from 0.1% by weight to 3% by weight, based on the reactive compound in the composition.

When the charge transporting layer 2B-2 is formed by photocuring, known photopolymerization initiators are used. Examples of the photo-radical initiator include an intramolecular cleavage type catalyst, a hydrogen abstraction type catalyst, and the like.

Examples of the intramolecular cleavage type catalyst include catalysts based on benzylketal, alkylphenone, aminoalkylphenone, phosphine oxide, titanocene, and oxime.

Specific examples of the benzylketal-based catalyst include 2,2-dimethoxy-1,2-diphenylethan-1-one. Examples of the alkylphenone-based catalyst include 1-hydroxy-cyclohexyl-phenyl-ketone, 2-hydroxy-2-methyl-1-phenyl-propan-1-one, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, acetophenone, and 2-phenyl-2-(p-toluenesulfonyloxy)acetophenone. Examples of the aminoalkylphenone-based catalyst include p-dimethylaminoacetophenone, p-dimethylaminopropiophenone, 2-methyl-1-(4-methylthiophenyl)-2-morpholinopropan-1-one, 2-benzyl-2-dimethylamino-1-(4-morpholinophenyl)-butanone-1,2-(dimethylamino)-2-[(4-methylphenyl)methyl]-1-[4-(4-morpholinyl)phenyl]-1-butanone, and the like. Examples of the phosphine oxide-based catalyst include 2,4,6-trimethylbenzoyl-diphenyl-phosphine oxide, bis(2,4,6-trimethylbenzoyl)-phenylphosphine oxide, and the like. Examples of the titanocene-based catalyst include bis(η5-2,4-cyclopentadiene-1-yl)-bis(2,6-difluoro-3-(1H-pyrrol-1-yl)-phenyl)titanium and the like. Examples of the oxime-based catalyst include 1,2-octanedione, 1-[4-(phenylthio)-, 2-(O-benzoyloxime)], ethanone, 1-[9-ethyl-6-(2-methylbenzoyl)-9H-carbazole-3-yl, 1-(O-acetyloxime) and the like.

Examples of the hydrogen abstraction type catalyst include catalysts based on benzophenone, thioxanthone, benzyl, Michler ketone, and the like.

Specific examples of the benzophenone-based catalyst include 2-benzoyl benzoate, 2-chlorobenzophenone, 4,4'-dichlorobenzophenone, 4-benzoyl 4'-methyldiphenyl sulfide, p,p'-bisdiethylaminobenzophenone, and the like. Examples of the thioxanthone-based catalyst include 2,4-diethylthioxanthen-9-one, 2-chlorothioxanthone, 2-isopropylthioxanthone, and the like. Examples of the benzyl-based type catalyst include benzyl, (±)-camphorquinone, p-anisil, and the like.

The photo-radical initiator is contained in the composition desirably at from 0.001% by weight to 10% by weight, more desirably from 0.01% by weight to 5% by weight, and even more desirably from 0.1% by weight to 3% by weight, based on the reactive compound in the composition.

To the composition used for forming the charge transporting layer 2B-2, other thermosetting resins such as a phenol resin, a melamine resin, and a benzoguanamine resin may be added, in order that oxidation caused by gas generated by discharge is effectively inhibited by these resins which are added to keep the composition from adsorbing too much gas generated by discharge.

In addition, for the purpose of adjusting film formability, flexibility, smoothness, and adhesiveness of the film, a coupling agent, a hard coating agent, and a fluorine-containing compound may be further added to the composition used for forming the charge transporting layer 2B-2. Specifically, as these additives, various silane coupling agents and commercially available silicone-based hard coating agents are used.

As the silane coupling agents, vinyl trichlorosilane, vinyl trimethoxysilane, vinyl triethoxysilane, glycidoxypropyl methyl diethoxysilane, γ-glycidoxypropyl trimethoxysilane, γ-aminopropyl triethoxysilane, γ-aminopropyl trimethoxysilane, γ-aminopropyl methyl dimethoxysilane, N-β(aminoethyl) γ-aminopropyl triethoxysilane, tetramethoxysilane, methyl trimethoxysilane, dimethyl dimethoxysilane, and the like are used.

As the commercially available hard coating agents, KP-85, X-40-9740, and X-8239 (all manufactured by ShinEtsu Silicones); AY42-440, AY42-441, and AY49-208 (all manufactured by Dow Corning Toray); and the like are used.

In addition, in order to impart water repellency or the like, fluorine-containing compounds such as (tridecafluoro-1,1,2,2-tetrahydrooctyl)triethoxysilane, (3,3,3-trifluoropropyl)trimethoxysilane, 3-(heptafluoroisopropoxy)propyl triethoxysilane, 1H,1H,2H,2H-perfluoroalkyl triethoxysilane, 1H,1H,2H,2H-perfluorodecyl triethoxysilane, and 1H,1H,2H,2H-perfluorooctyl triethoxysilane may also be added.

The silane coupling agent is used in an arbitrary amount, but the amount of the fluorine-containing compound is desirably 0.25 time or less of the compound not containing fluorine in terms of a weight ratio, in view of the formability of the crosslinked film.

For the purposes of adjusting the discharge gas resistance, mechanical strength, and damage resistance of the charge transporting layer 2B-2, reducing torque, controlling abrasion loss, and extending pot life, or for the purposes of controlling particle dispersibility and viscosity, a thermoplastic resin may be added to the composition used for forming the charge transporting layer 2B-2.

Examples of the thermoplastic resin include a polyvinyl butyral resin, a polyvinyl formal resin, a polyvinyl acetal resin (for example S-LEC B, K, and the like manufactured by Sekisui Chemical Co., Ltd.) such as a partially acetalized polyvinyl acetal resin obtained when a portion of butyral is modified with formal, acetoacetal, or the like, a polyamide resin, a cellulose resin, a polyvinyl phenol resin, and the like. Particularly, in view of electrical characteristics, a polyvinyl acetal resin and a polyvinyl phenol resin are desirable. The weight average molecular weight of the resin is desirably from 2,000 to 100,000, and more desirably from 5,000 to 50,000. If the molecular weight of the resin is less than 2,000, the effect produced by the addition of the resin tends to be insufficient. If the molecular weight exceeds 100,000, solubility decreases, the amount of the resin added is restricted, and a defective film tends to be formed when the composition is coated. The amount of the resin added is desirably from 1% by weight to 40% by weight, more desirably from 1% by weight to 30% by weight, and even more desirably from 5% by weight to 20% by weight. If the amount of the resin added is less than 1% by weight, the effect produced by the addition of the resin tends to be insufficient, and if it exceeds 40% by weight, image blurring easily occurs at a high temperature and high humidity (for example, 28° C. and 85% RH).

For the purpose of preventing the deterioration of the charge transporting layer 2B-2 caused by oxidizing gas such as ozone which is generated by a charging device, it is desirable to add an antioxidant to the composition used for forming the charge transporting layer 2B-2. If the mechanical strength of the photoreceptor surface increases, and the life of the photoreceptor is extended, the photoreceptor contacts the oxidizing gas for a long time. Accordingly, oxidation resistance stronger than that in the related art is required.

As the antioxidant, antioxidants based on hindered phenol or hindered amine are desirable, and known antioxidants such as an organic sulfur-based antioxidant, a phosphite-based antioxidant, a dithiocarbamic acid salt-based antioxidant, a thiourea-based antioxidant, and a benzimidazole-based antioxidant may also be used. The amount of the antioxidant added is desirably 20% by weight or less, and more desirably 10% by weight or less.

Examples of the hindered phenol-based antioxidant include 2,6-di-t-butyl-4-methylphenol, 2,5-di-t-butylhydroquinone, N,N'-hexamethylenebis(3,5-di-t-butyl-4-hydroxyhydrocinnamide, 3,5-di-t-butyl-4-hydroxy-benzylphosphonate-diethyl ester, 2,4-bis[(octylthio)methyl]-o-cresol, 2,6-di-t-butyl-4-ethylphenol, 2,2'-methylenebis(4-methyl-6-t-butylphenol), 2,2'-methylenebis(4-ethyl-6-t-butylphenol), 4,4'-butylidenebis(3-methyl-6-t-butylphenol), 2,5-di-t-amyl-hydroquinone, 2-t-butyl-6-(3-butyl-2-hydroxy-5-methyl-benzyl)-4-methylphenyl acrylate, 4,4'-butylidenebis(3-methyl-6-t-butylphenol), and the like.

For the purpose of decreasing the residual potential of the charge transporting layer 2B-2 or improving the strength of the charge transporting layer 2B-2, various particles may be added to the composition used for forming the charge transporting layer 2B-2.

An example of the particles includes silicon-containing particles. The silicon-containing particles are particles containing silicon as a constituent element, and specific examples thereof include colloidal silica, silicone particles, and the like. The colloidal silica used as the silicon-containing particles is selected from those obtained by dispersing silica having an average particle size of from 1 nm to 100 nm and desirably from 10 nm to 30 nm in an organic solvent such as an acidic or alkaline aqueous dispersion, an alcohol, a ketone, or an ester, and commercially available general colloidal silica may also be used. The solid content of the colloidal silica contained in the charge transporting layer 2B-2 is not particularly limited. However, the colloidal silica is used in a range of from 0.1% by weight to 50% by weight, and desirably in a range of from 0.1% by weight to 30% by weight, based on the total solid content amount of the charge transporting layer 2B-2, in respect of film formability, electrical characteristics, and strength.

The silicone particles used as the silicon-containing particles are selected from silicone resin particles, silicone rubber particles, and silica particles that are surface-treated with silicone, and commercially available general silicone particles are used. These silicone particles are spherical, and the average particle size thereof is desirably from 1 nm to 500 nm, and more desirably from 10 nm to 100 nm. The silicone particles are small size particles that are chemically inactive and have excellent dispersibility with a resin. The amount of the silicone particles added that is required for obtaining more sufficient characteristics is small. Accordingly, the surface properties of the electrophotographic photoreceptor are improved without hindering a crosslinking reaction. That is, while these particles are incorporated in a strong crosslinked structure without variation, the lubricity and water repellency of the electrophotographic photoreceptor surface are improved, and excellent abrasion resistance and a contaminant-repelling property are maintained over a long time.

The content of the silicone particles in the charge transporting layer 2B-2 is desirably from 0.1% by weight to 30% by weight, and more desirably from 0.5% by weight to 10% by weight, based on the total solid content amount of the charge transporting layer 2B-2.

Examples of other particles include fluorine-based particles such as tetrafluoroethylene, trifluoroethylene, hexafluoropropylene, vinyl fluoride, vinylidene fluoride; particles including a resin that is obtained by copolymerizing a fluororesin with a monomer having a hydroxyl group, as disclosed in "Proceedings of the 8$^{th}$ Polymer Material Forum, 89"; and semiconductive metallic oxides such as ZnO—$Al_2O_3$, $SnO_2$—$Sb_2O_3$, $In_2O_3$—$SnO_2$, $ZnO_2$—$TiO_2$, ZnO—$TiO_2$, MgO—$Al_2O_3$, FeO—$TiO_2$, $TiO_2$, $SnO_2$, $In_2O_3$, ZnO, and MgO. For the same purpose as described above, oil such as silicone oil may be added. Examples of the silicone oil include silicone oil such as dimethyl polysiloxane, diphenyl polysiloxane, or phenyl methyl siloxane; reactive silicone oil such as amino-modified polysiloxane, epoxy-modified polysiloxane, carboxyl-modified polysiloxane, carbinol-modified polysiloxane, methacryl-modified polysiloxane, mercapto-modified polysiloxane, or phenol-modified polysiloxane; cyclic dimethyl cyclosiloxanes such as hexamethyl cyclotrisiloxane, octamethyl cyclotetrasiloxane, decamethyl cyclopentasiloxane, and dodecamethyl cyclohexasiloxane; cyclic methylphenyl cyclosiloxanes such as 1,3,5-trimethyl-1,3,5-triphenyl cyclotrisiloxane, 1,3,5,7-tetramethyl-1,3,5,7-tetraphenyl cyclotetrasiloxane, and 1,3,5,7,9-pentamethyl-1,3,5,7,9-pentaphenyl cyclopentasiloxane; cyclic phenyl cyclosiloxanes such as hexaphenyl cyclotrisiloxane; fluorine-containing cyclosiloxanes such as (3,3,3-trifluoropropyl)methyl cyclotrisiloxane; hydrosilyl group-containing cyclosiloxanes such as a methyl hydrosiloxane mixture, pentamethyl cyclopentasiloxane, and phenyl hydrocyclosiloxane; vinyl group-containing cyclosiloxanes such as pentavinyl pentamethyl cyclopentasiloxane; and the like.

A metal, metallic oxide, carbon black, and the like may also be added to the composition used for forming the charge transporting layer 2B-2. Examples of the metal include aluminum, zinc, copper, chromium, nickel, silver and stainless steel, or those obtained by vapor-depositing these metals onto the surface of plastic particles. Examples of the metallic oxide include zinc oxide, titanium oxide, tin oxide, antimony oxide, indium oxide, bismuth oxide, indium oxide doped with tin, tin oxide doped with antimony or tantalum, zirconium oxide doped with antimony, and the like. These metallic oxides may be used alone or in combination of two or more kinds thereof. When used in combination of two or more kinds thereof, the metallic oxide may be simply mixed, or may be used in the form of a solid solution or may be melted. The average particle size of the conductive particles is 0.3 µm or less, and particularly desirably 0.1 µm or less, in view of the transparency of the charge transporting layer 2B-2.

The composition used for forming the charge transporting layer 2B-2 is desirably prepared as a coating liquid for forming the charge transporting layer 2B-2. This coating liquid may be free of a solvent, or if necessary, this coating liquid may contain a solvent including aromatic hydrocarbons such as toluene, xylene, and chlorobenzene; alcohols such as methanol, ethanol, propanol, butanol, cyclopentanol, cyclohexanol; ketones such as acetone, methyl ethyl ketone, and methyl isobutyl ketone; ethers such as tetrahydrofuran, diethyl ether, diisopropyl ester, and dioxane; esters such as ethyl acetate, n-propyl acetate, n-butyl acetate, ethyl lactate; and the like.

These solvents may be used alone or used as a mixture of two or more kinds thereof, and a boiling point of the solvent is desirably 100° C. or lower.

In addition, for the purpose of improving storage stability of the coating liquid for forming the charge transporting layer 2B-2, a polymerization inhibitor may be contained in the coating liquid. As the polymerization inhibitor, known ones are used. The hindered phenol or hindered amine-based antioxidants exemplified above as specific examples of the antioxidants also function as the polymerization inhibitor, so these may be favorably used.

The coating liquid used for forming the charge transporting layer 2B-2 that contains the composition used for forming the charge transporting layer 2B-2 is coated onto a surface to be coated (the surface of charge transporting layer 2B-1 in the first embodiment shown in FIG. 1) on the charge transporting layer 2B-1 by general methods such as blade coating, wire bar coating, spray coating, dip coating, bead coating, air knife coating, and curtain coating, and cured (polymerized) if necessary by being heated at, for example, from 100° C. to 170° C., thereby obtaining a polymerized or cured film. In this manner, the charge transporting layer 2B-2 (corresponding to the layer (Oc1) of the exemplary embodiment in the first embodiment) including this polymerized or cured film is obtained.

The oxygen concentration in the coating liquid for forming the charge transporting layer 2B-2 during curing is desirably 1% or less, more desirably 1000 ppm or less, and even more desirably 500 ppm or less.

The coating liquid for forming the charge transporting layer 2B-2 is used not only for the photoreceptor, but also for an antistatic film of, for example, a fluorescence coating material, a glass surface, and a plastic surface. If this coating liquid is used, a coat having excellent adhesiveness with respect to the underlayer is formed, and performance deterioration caused by repeated use over a long time is inhibited.

—Charge Transporting Layer 2B (Corresponding to Layer (Oc2) of Exemplary Embodiment in the Second Embodiment)—

The charge transporting layer 2B may have the same configuration as that of the charge transporting layer 2B-2 in the first embodiment. The composition for forming the charge transporting layer 2B and the method of forming this layer are the same as those in the case of the charge transporting layer 2B-2.

—Single Layer Type Photosensitive Layer 6 (Corresponding to Layer (Oc3) of Exemplary Embodiment in the Third Embodiment)—

So far, as the electrophotographic photoreceptor, a functional separation type has been described for example. The content of the charge generating material in the single layer type photosensitive layer 6 (charge generating/charge transporting layer) shown in FIG. 3 is from 10% by weight to 85% by weight, and desirably from 20% by weight to 50% by weight. In addition, the content of the charge transport material is desirably from 5% by weight to 50% by weight.

The method of forming the single layer type photosensitive layer 6 (charge generating/charge transporting layer) is the same as that of the charge generating layer 2A and the charge transporting layer 2B-2. The film thickness of the single layer type photosensitive layer (charge generating/charge transporting layer) 6 is desirably from 5 μm to 50 μm, and more desirably from 10 μm to 40 μm.

In the above exemplary embodiment, an embodiment was described in which the uppermost surface layer (charge transporting film) including the polymerized or cured film of the composition containing the charge transport material (A1) or (A2) is a charge transporting layer or a photosensitive layer. However, when a protective layer is provided as the uppermost surface layer on the charge transporting layer or photosensitive layer, the protective layer may be configured with a polymerized or cured film of the composition containing the charge transport material (A1) or (A2).

In addition, in the exemplary embodiment described above, an embodiment was described in which a polymerized or cured film (charge transporting film) of the composition containing the charge transport material (A1) or (A2) of the exemplary embodiment is applied as the uppermost surface layer of the electrophotographic photoreceptor. However, the polymerized or cured film containing the charge transport material (A1) or (A2) of the exemplary embodiment is not limited to this embodiment. The cured film containing the charge transport material (A1) or (A2) of the exemplary embodiment is also applied to, for example, an electroluminescence (EL) element, a memory device, and a wavelength conversion element. Moreover, it is considered that the cured film according to the exemplary embodiment is formed without impairing the charge transport property. Accordingly, this film does not exhibit morphological change which is caused by Joule heat and is observed in the charge transporting film in the related art, and has excellent film formability at the time of lamination. Consequently, this cured film is useful for the above-described purposes.

[Photoelectric Conversion Device]

The photoelectric conversion device according to the exemplary embodiment is characterized by including the charge transporting film according to the exemplary embodiment described above.

As described above, the charge transporting film according to the exemplary embodiment is excellent in both the mechanical strength and charge transport performance. Therefore, this film may be suitably applied to a layer which needs to have mechanical strength in a photoelectric conversion device.

Examples of the photoelectric device according to the exemplary embodiment include an electrophotographic photoreceptor, an organic EL device, an organic transistor, an organic solar cell, and the like.

Specifically, for example, the organic EL device is configured with a pair of electrodes in which at least one of the electrodes is transparent or semitransparent, and one or plural organic compound layers interposed between these electrodes. The charge transporting film according to the exemplary embodiment of the invention may be used for at least one of the organic compound layers, and the layer configuration thereof is not particularly limited. Specifically, the charge transporting film according to the exemplary embodiment is applied as a luminous layer, a hole transporting layer, and a hole injecting layer.

In addition, for example, an organic thin film transistor includes an organic semiconductor layer that contacts both a source electrode and a drain electrode facing to each other, a gate electrode that is separated from both the source electrode and drain electrode, and an insulating layer disposed between the organic semiconductor layer and the gate electrode. The charge transporting film according to the exemplary embodiment of the invention may be used for at least one of the organic semiconductor layers, and the layer configuration thereof is not particularly limited.

EXAMPLES

Hereinafter, the invention will be described in more detail based on examples, but the invention is not limited thereto.

Synthesis Example 1-1

—Synthesis of Charge Transport Agent (I)-7 of Exemplary Embodiment of the Invention—

To a 500 ml three-neck flask, 32.6 g of 3,4-dimethylacetanilide, 56.0 g of 4-iodobiphenyl, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to 120° C., and then 50 ml of ethylene glycol and an aqueous potassium hydroxide solution (potassium hydroxide 15.7 g/water 20 ml) are added thereto, followed by stirring for another 6 hours. Subsequently, the temperature is reduced to room temperature, and 200 ml of toluene and 150 ml of water are added thereto, thereby performing liquid separation. A toluene layer is collected, 20 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 42.1 g of I-7a (yield 77%).

To a 500 ml three-neck flask, 41.0 g of I-7a, 43.5 g of methyl 3-(4-iodophenyl)propionate, 22.8 g of potassium carbonate, 1.1 g of copper sulfate pentahydrate, and 40 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 20 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 47.0 g of I-7b (yield 72%).

To a 3 L three-neck flask, 43.6 g of I-7b and 450 ml of tetrahydrofuran are added, and an aqueous solution obtained by dissolving 4.4 g of sodium hydroxide in 450 ml of water is added thereto, followed by stirring at 60° C. for 3 hours. Thereafter, the reaction solution is added dropwise to an aqueous solution of water 1 L/concentrated hydrochloric acid 20 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 31.2 g of I-7c (yield 74%).

To a 500 ml three-neck flask, 29.5 g of I-7c, 11.8 g of 4-chloromethylstyrene, 10.6 g of potassium carbonate, 0.17 g of nitrobenzene, and 175 ml of DMF (N,N-dimethylformamide) are added, and this mixture is stirred for 3 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 29.7 g of a charge transport agent (I)-7 of the exemplary embodiment of the invention (yield 79%).

Figure 4:
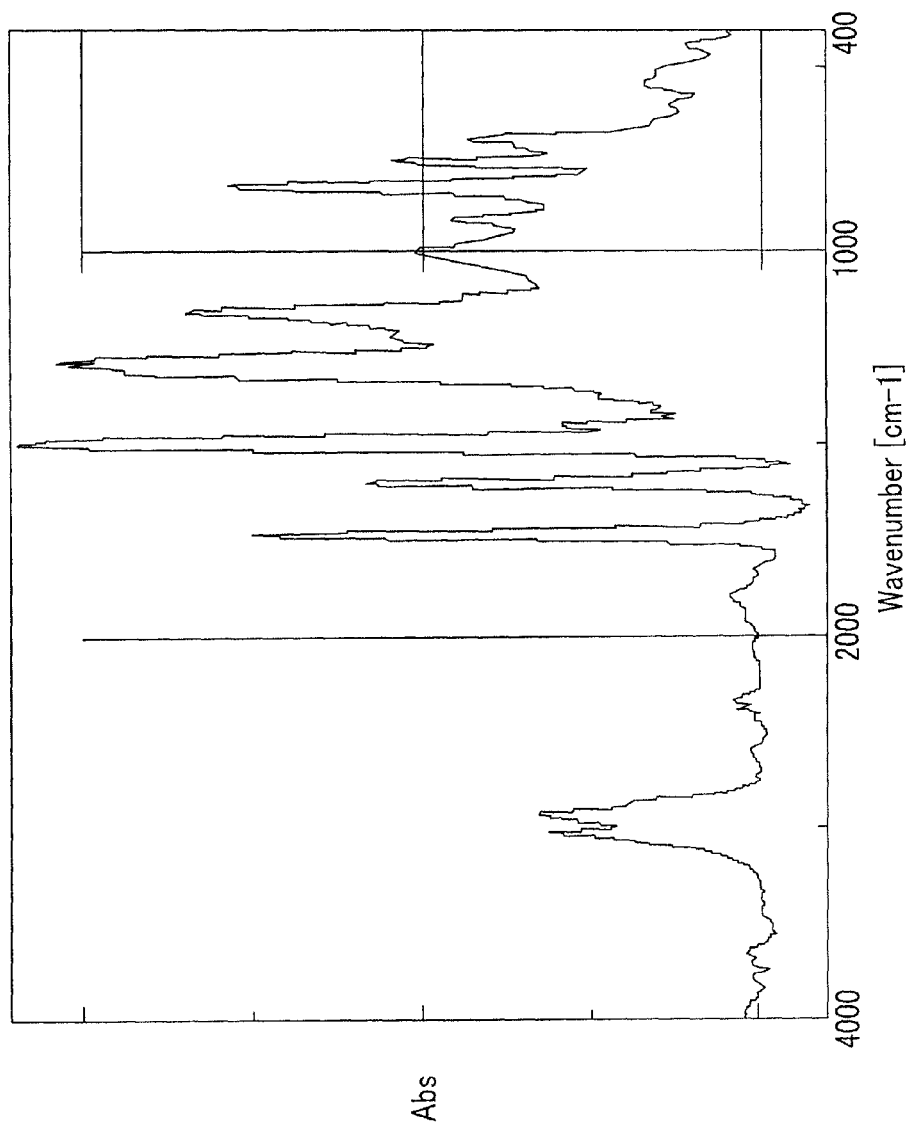
FIG. 4 is an IR spectrum of a compound (I)-7.

The IR spectrum of the obtained compound (I)-7 is shown in FIG. 4.

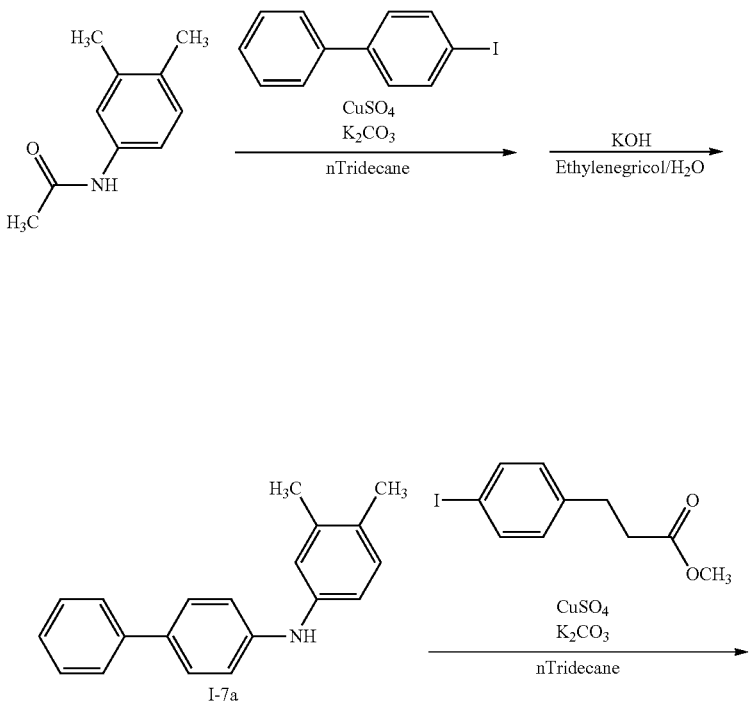

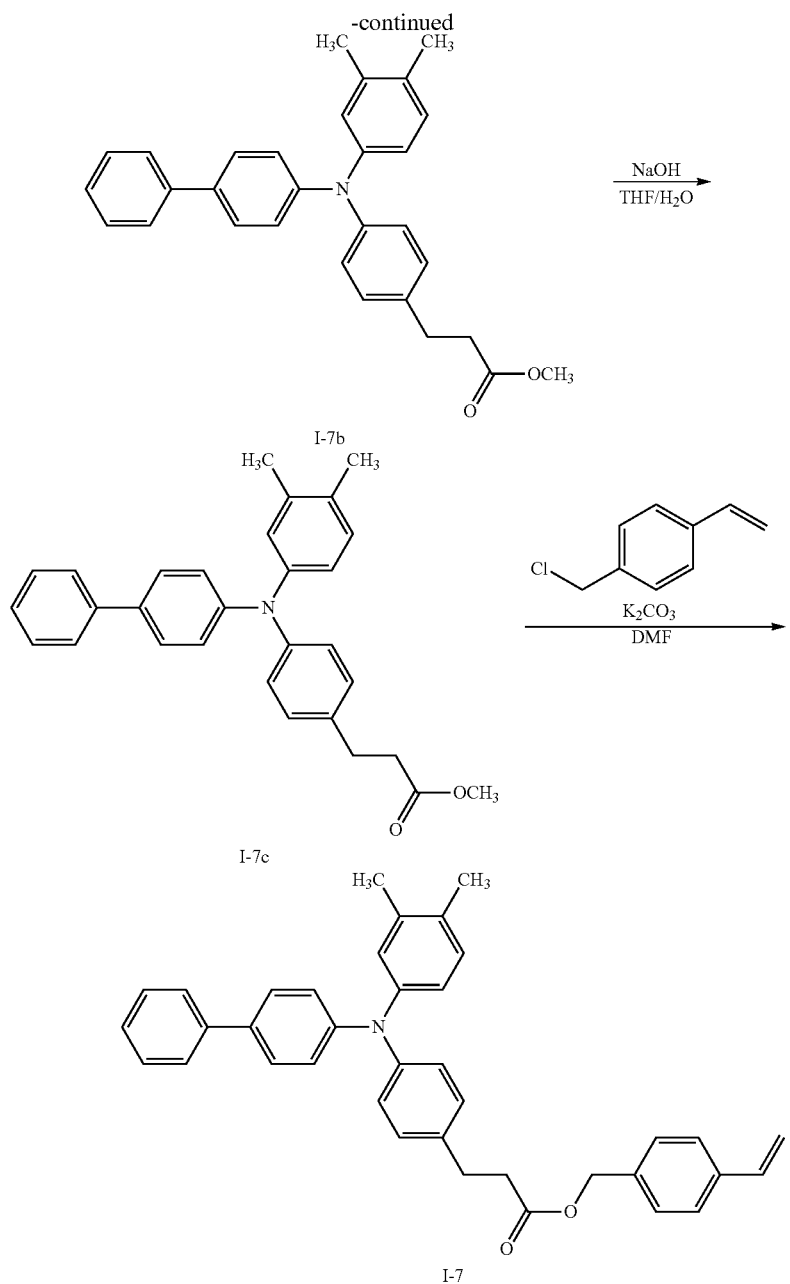

Synthesis Example 1-2

—Synthesis of Charge Transport Agent (I)-15 of Exemplary Embodiment of the Invention—

To a 500 ml three-neck flask, 68.3 g of 4,4'-bis(2-methoxycarbonylethyl)diphenylamine, 46.4 g of 4-iodoxylene, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 20 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 65.1 g of I-15a (yield 73%).

To a 3 L three-neck flask, 59.4 g of I-15a and 450 ml of tetrahydrofuran are added, and an aqueous solution obtained by dissolving 11.7 g of sodium hydroxide in 450 ml of water is added thereto, followed by stirring at 60° C. for 3 hours. Thereafter, the reaction solution is added dropwise to an aqueous solution of water 1 L/concentrated hydrochloric acid 60 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 46.2 g of I-15b (yield 83%).

To a 500 ml three-neck flask, 29.2 g of I-15b, 23.5 g of 4-chloromethylstyrene, 21.3 g of potassium carbonate, 0.17 g of nitrobenzene, and 175 ml of DMF (N,N-dimethylformamide) are added, and this mixture is stirred for 3 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 36.4 g of a charge transport agent (I)-15 of the exemplary embodiment of the invention (yield 80%).

Figure 5:
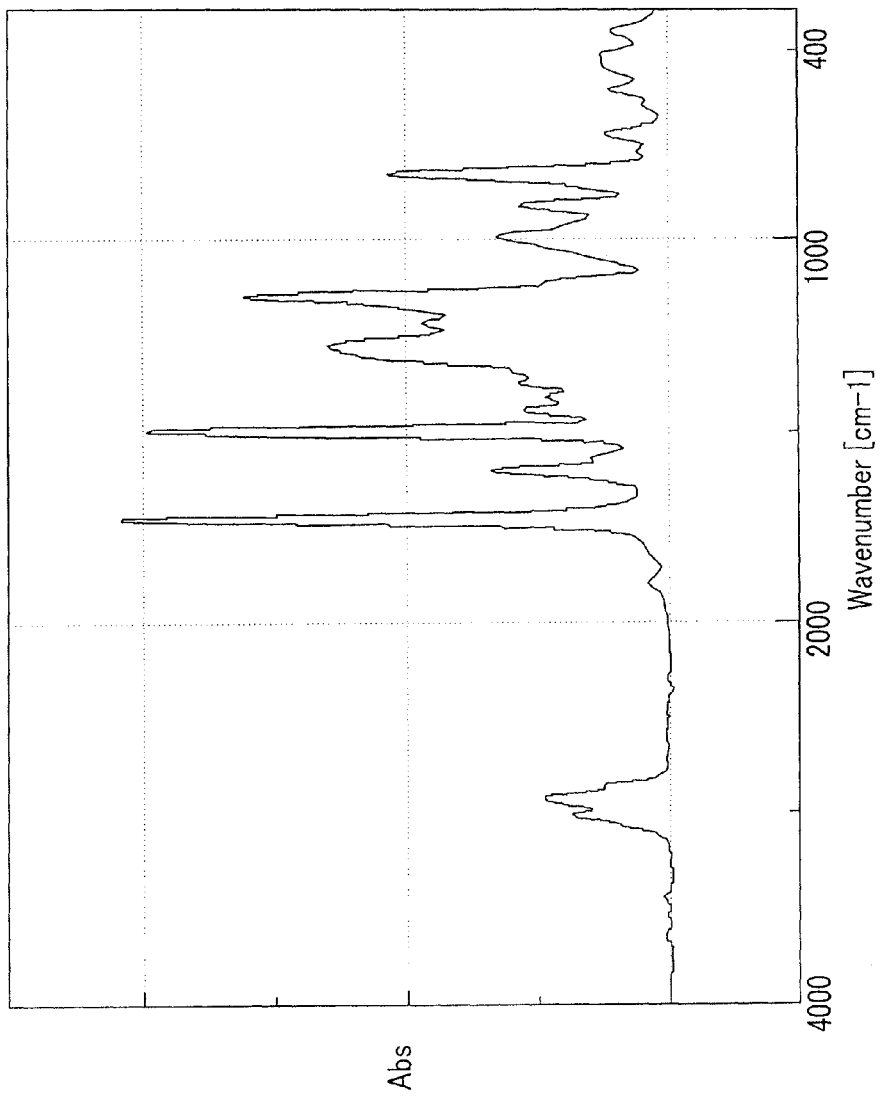
FIG. 5 is an IR spectrum of a compound (I)-15.

The IR spectrum of the obtained compound (I)-15 is shown in FIG. 5.

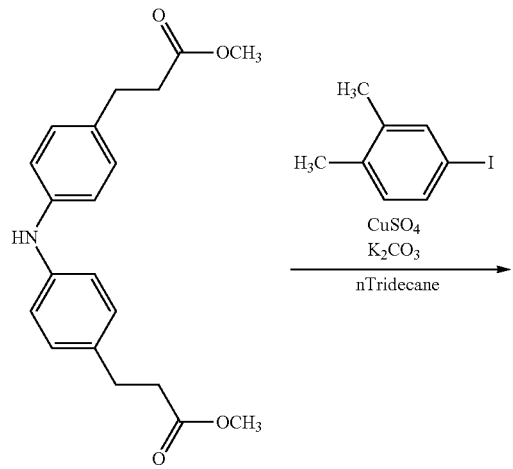

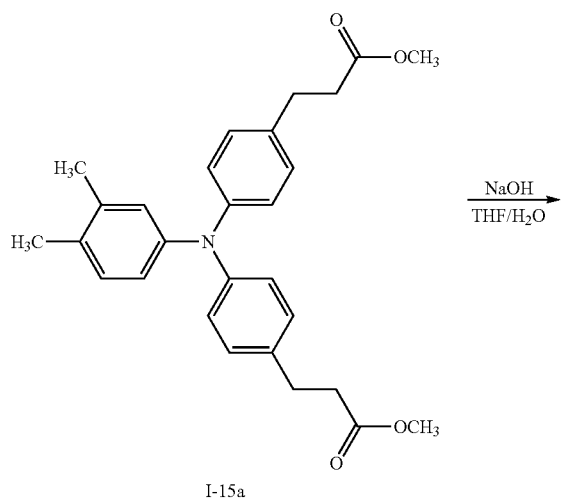

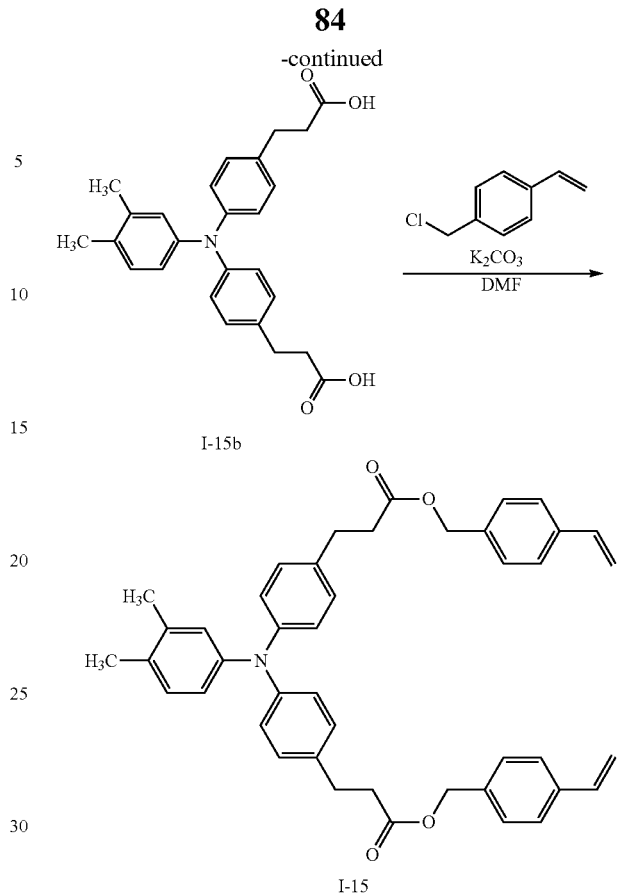

Synthesis Example 1-3

—Synthesis of Charge Transport Agent (I)-17 of Exemplary Embodiment of the Invention—

To a 500 ml three-neck flask, 68.3 g of 4,4'-bis(2-methoxycarbonylethyl)diphenylamine, 56.0 g of 4-iodobiphenyl, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 20 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 74.0 g of I-17a (yield 75%).

To a 3 L three-neck flask, 65.8 g of I-17a and 450 ml of tetrahydrofuran are added, and an aqueous solution obtained by dissolving 11.7 g of sodium hydroxide in 450 ml of water is added thereto, followed by stirring at 60° C. for 3 hours. Thereafter, the reaction solution is added dropwise to an aqueous solution of water 1 L/concentrated hydrochloric acid 60 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 53.4 g of I-17b (yield 86%).

To a 500 ml three-neck flask, 32.6 g of I-17b, 23.5 g of 4-chloromethylstyrene, 21.3 g of potassium carbonate, 0.17 g of nitrobenzene, and 175 ml of DMF (N,N-dimethylformamide) are added, and this mixture is stirred for 3 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered.

A crude product obtained after distilling away the ethyl acetate under reduced pressure is purified through silica gel column chromatography by using toluene/ethyl acetate as an eluent, thereby obtaining 36.8 g of a charge transport agent (I)-17 of the exemplary embodiment of the invention (yield 81%).

Figure 6:
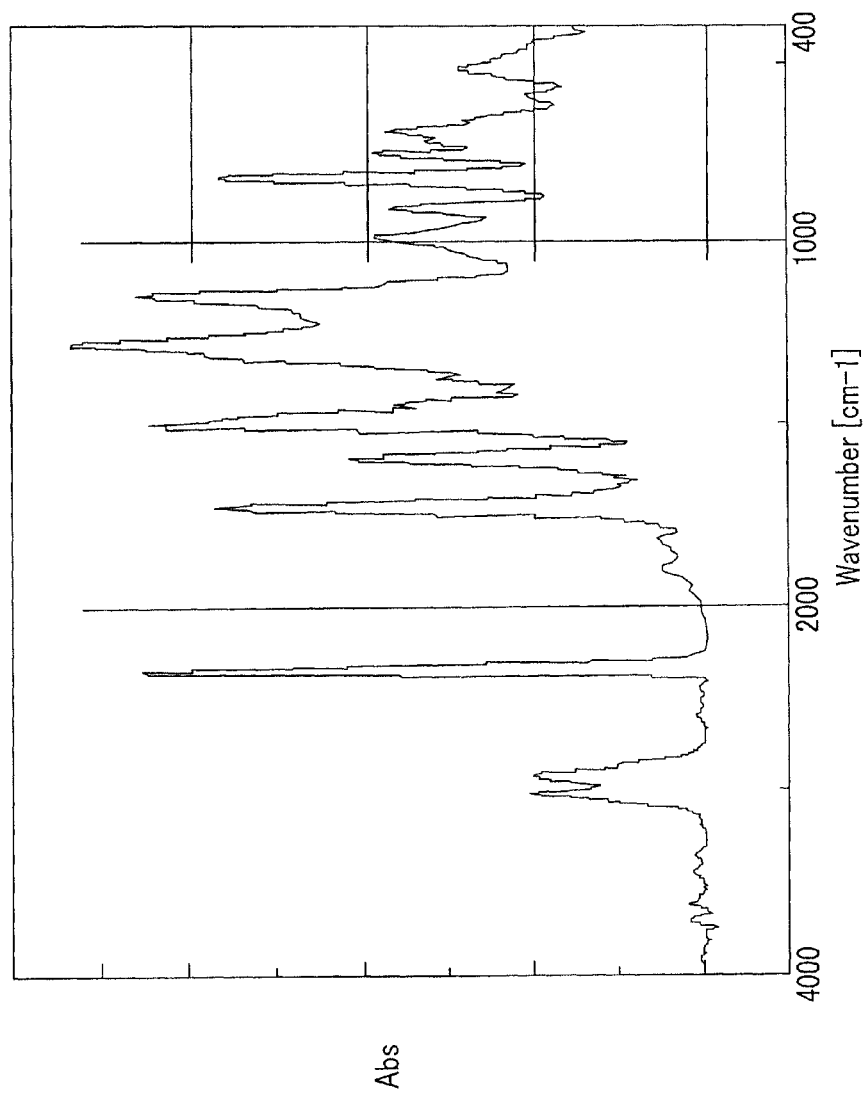
FIG. 6 is an IR spectrum of a compound (I)-17.

The IR spectrum of the obtained compound (I)-17 is shown in FIG. 6.

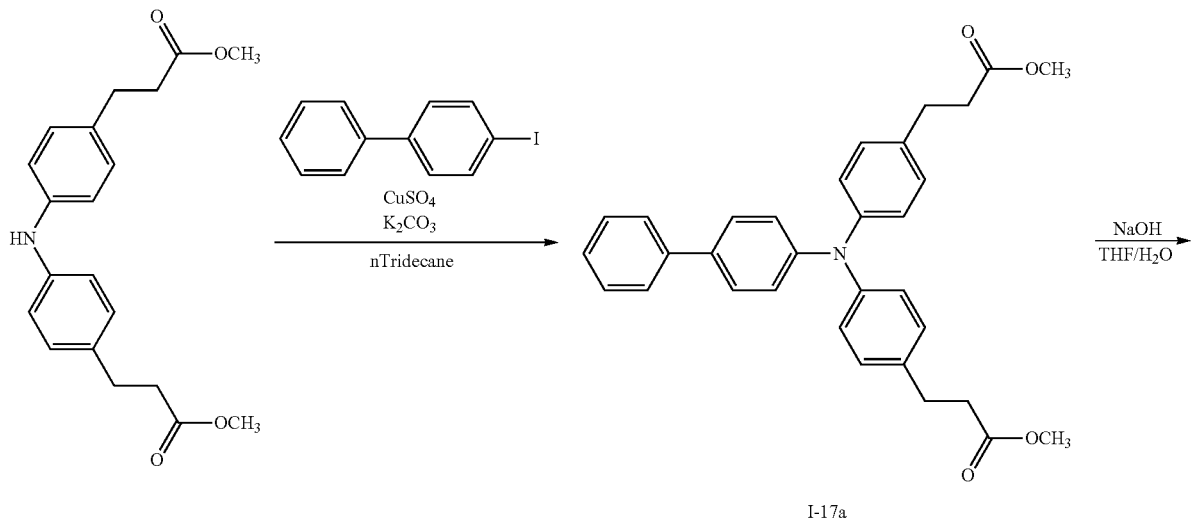

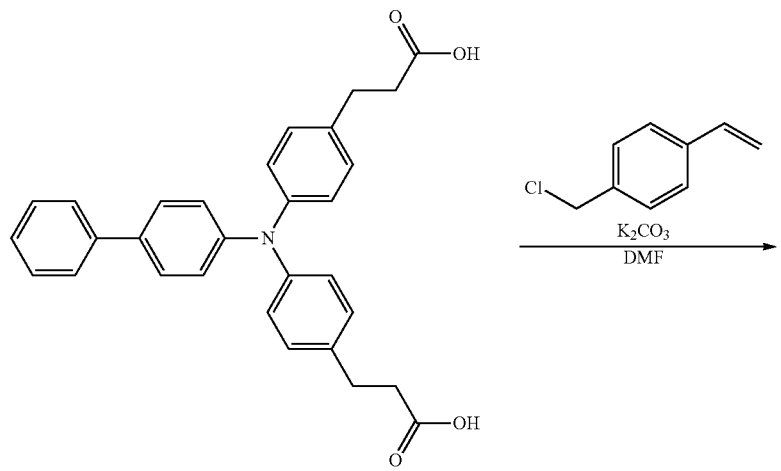

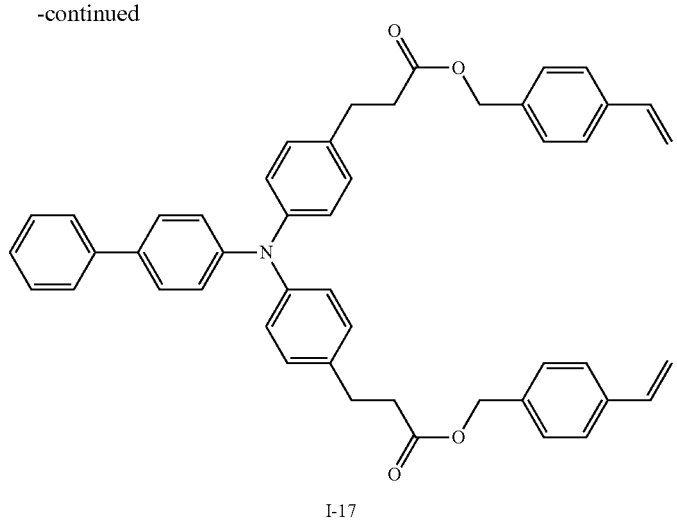

I-17

Synthesis Example 1-4

—Synthesis of Charge Transport Agent (I)-23 of Exemplary Embodiment of the Invention—

To a 500 ml three-neck flask, 56.7 g of methyl 3-[4-(3,4-dimethylphenylamino)phenyl)]propionate, 43.4 g of 4,4'-diiodo-3,3'-dimethyl-1,1'-biphenyl, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 10 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 48.4 g of I-23a (yield 65%).

To a 3 L three-neck flask, 37.3 g of I-23a and 350 ml of tetrahydrofuran are added, and an aqueous solution obtained by dissolving 4.4 g of sodium hydroxide in 350 ml of water is added thereto, and then this mixture is stirred for 5 hours while being heated at 60° C. Thereafter, the reaction solution is added dropwise to an aqueous solution of water 1 L/concentrated hydrochloric acid 20 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 32.6 g of I-23b (yield 91%).

To a 500 ml three-neck flask, 25.1 g of I-23b, 11.8 g of 4-chloromethylstyrene, 10.6 g of potassium carbonate, 0.09 g of nitrobenzene, and 175 ml of DMF (N,N-dimethylformamide) are added, and this mixture is stirred for 5 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 28.2 g of a charge transport agent (I)-23 of the exemplary embodiment of the invention (yield 85%).

Figure 7:
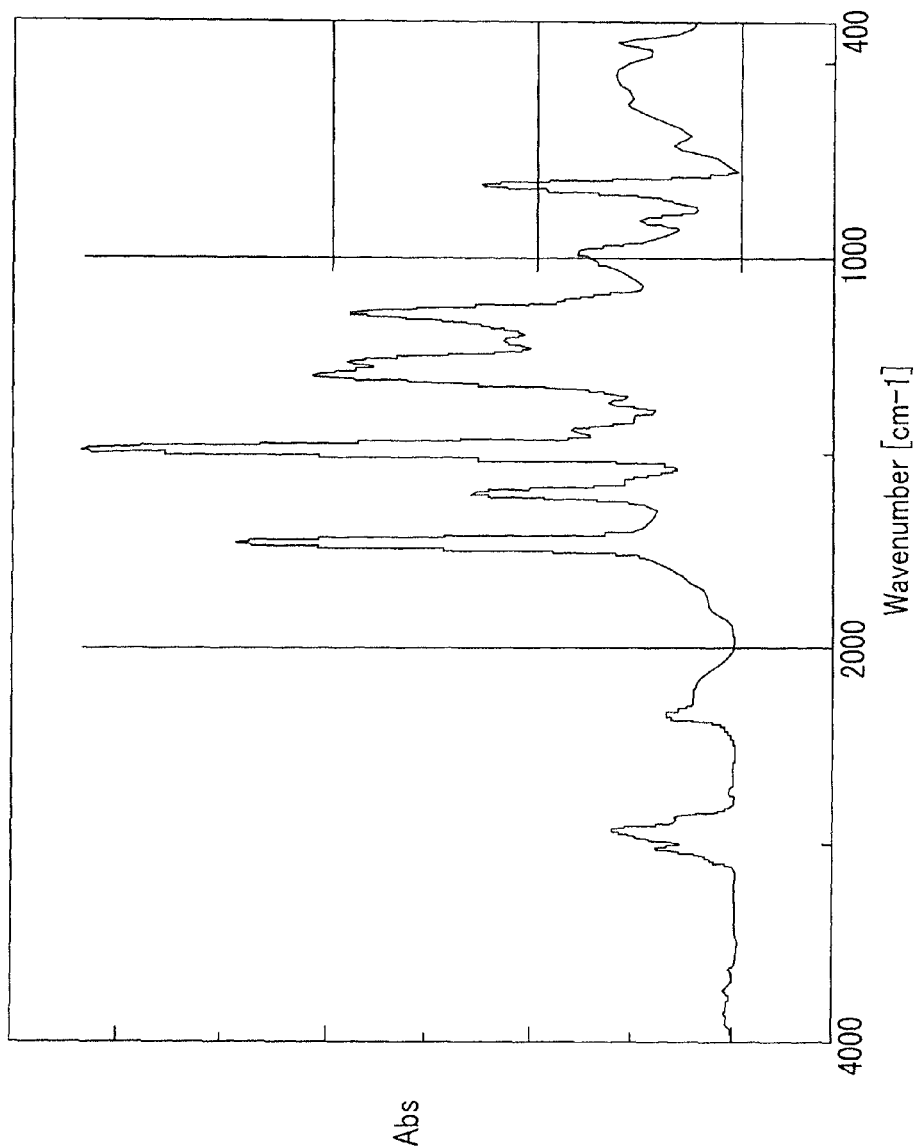
FIG. 7 is an IR spectrum of a compound (I)-23.

The IR spectrum of the obtained compound (I)-23 is shown in FIG. 7.

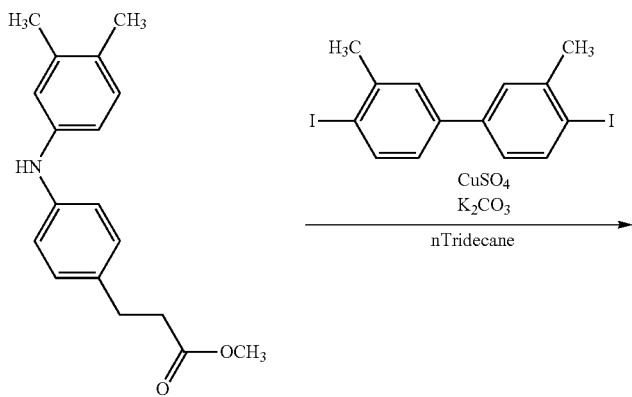

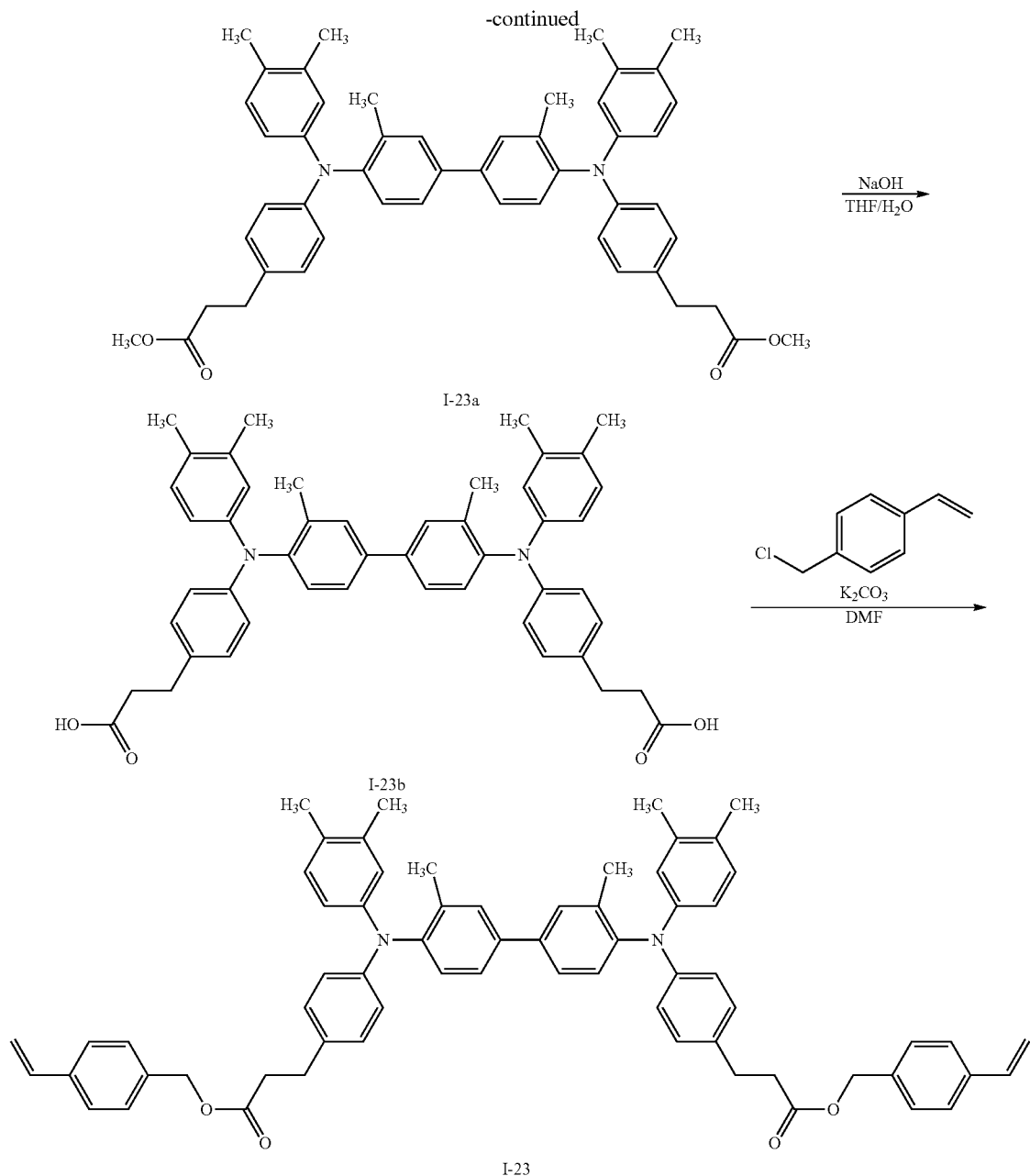

Synthesis Example 1-5

—Synthesis of Charge Transport Agent (I)-25 Exemplary Embodiment of the Invention—

To a 500 ml three-neck flask, 51.1 g of methyl 3-[4-(phenylamino)phenyl]propionate, 43.4 g of 1,2-bis(4-iodophenyl)ethane, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 10 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 51.7 g of I-25a (yield 75%).

To a 3 L three-neck flask, 34.4 g of I-25a and 350 ml of tetrahydrofuran are added, and an aqueous solution obtained by dissolving 4.4 g of sodium hydroxide in 350 ml of water is added thereto, and then this mixture is stirred for 5 hours while being heated at 60° C. Thereafter, the reaction solution is added dropwise to an aqueous solution of water 1 L/concentrated hydrochloric acid 20 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 28.4 g of I-25b (yield 86%).

To a 500 ml three-neck flask, 23.1 g of I-25b, 11.8 g of 4-chloromethylstyrene, 10.6 g of potassium carbonate, 0.09 g of nitrobenzene, and 175 ml of DMF (N,N-dimethylformamide) are added, and this mixture is stirred for 5 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered.

A crude product obtained after distilling away the ethyl acetate under reduced pressure is purified through silica gel column chromatography by using toluene/ethyl acetate as an eluent, thereby obtaining 25.6 g of a charge transport agent (I)-25 of the exemplary embodiment of the invention (yield 82%).

Figure 8:
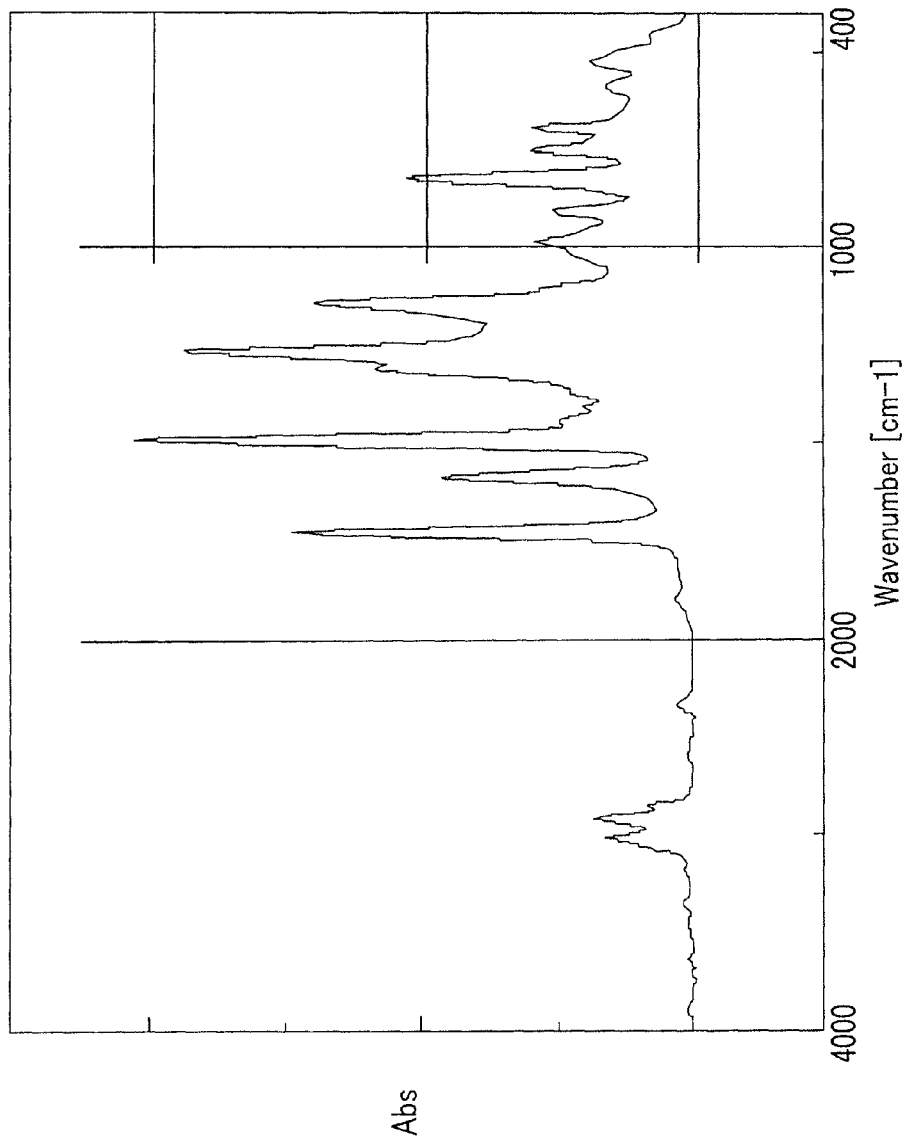
FIG. 8 is an IR spectrum of a compound (I)-25.

The IR spectrum of the obtained compound (I)-25 is shown in FIG. 8.

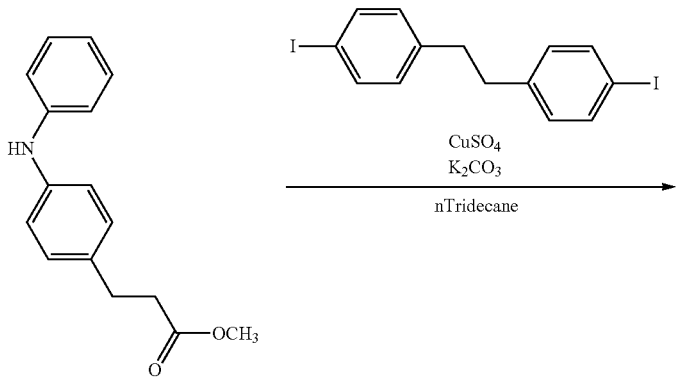

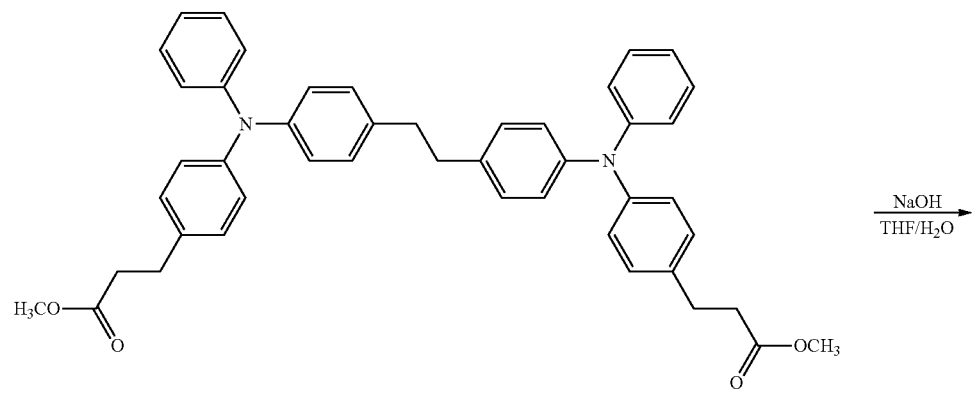

I-25a

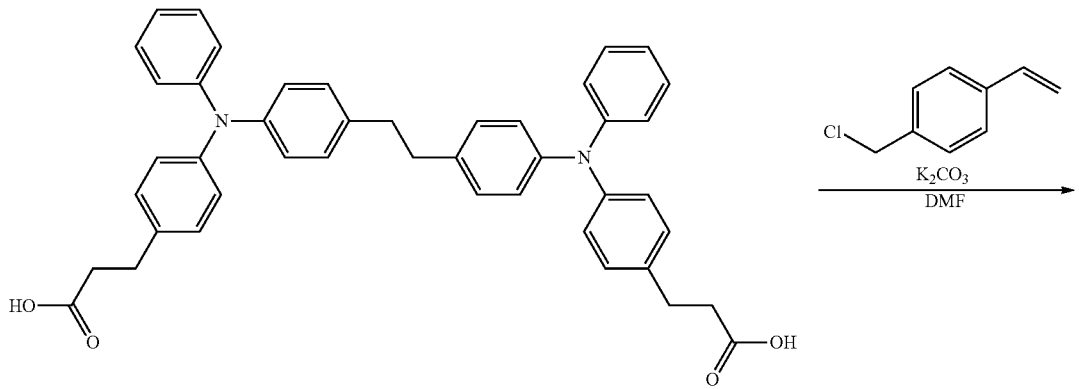

I-25b

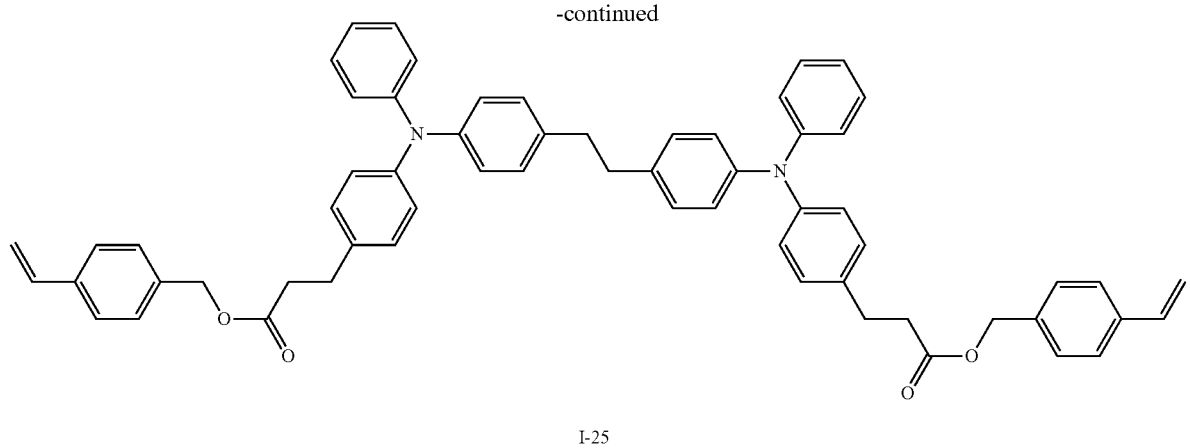

I-25

Synthesis Example 1-6

—Synthesis of Charge Transport Agent (I)-27 of Exemplary Embodiment of the Invention—

To a 500 ml three-neck flask, 56.7 g of methyl 3-[4-(3,4-dimethylphenylamino)phenyl]propionate, 43.4 g of 1,2-bis(4-iodophenyl)ethane, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 10 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 54.4 g of I-27a (yield 73%).

To a 3 L three-neck flask, 37.3 g of I-27a and 350 ml of tetrahydrofuran are added, and an aqueous solution obtained by dissolving 4.4 g of sodium hydroxide in 350 ml of water is added thereto, and then this mixture is stirred for 5 hours while being heated at 60° C. Thereafter, the reaction solution is added dropwise to an aqueous solution of water 1 L/concentrated hydrochloric acid 20 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 29.4 g of I-27b (yield 82%).

To a 500 ml three-neck flask, 25.1 g of I-27b, 11.8 g of 4-chloromethylstyrene, 10.6 g of potassium carbonate, 0.09 g of nitrobenzene, and 175 ml of DMF (N,N-dimethylformamide) are added, and this mixture is stirred for 5 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 26.2 g of a charge transport agent (I)-27 of the exemplary embodiment of the invention (yield 79%).

Figure 9:
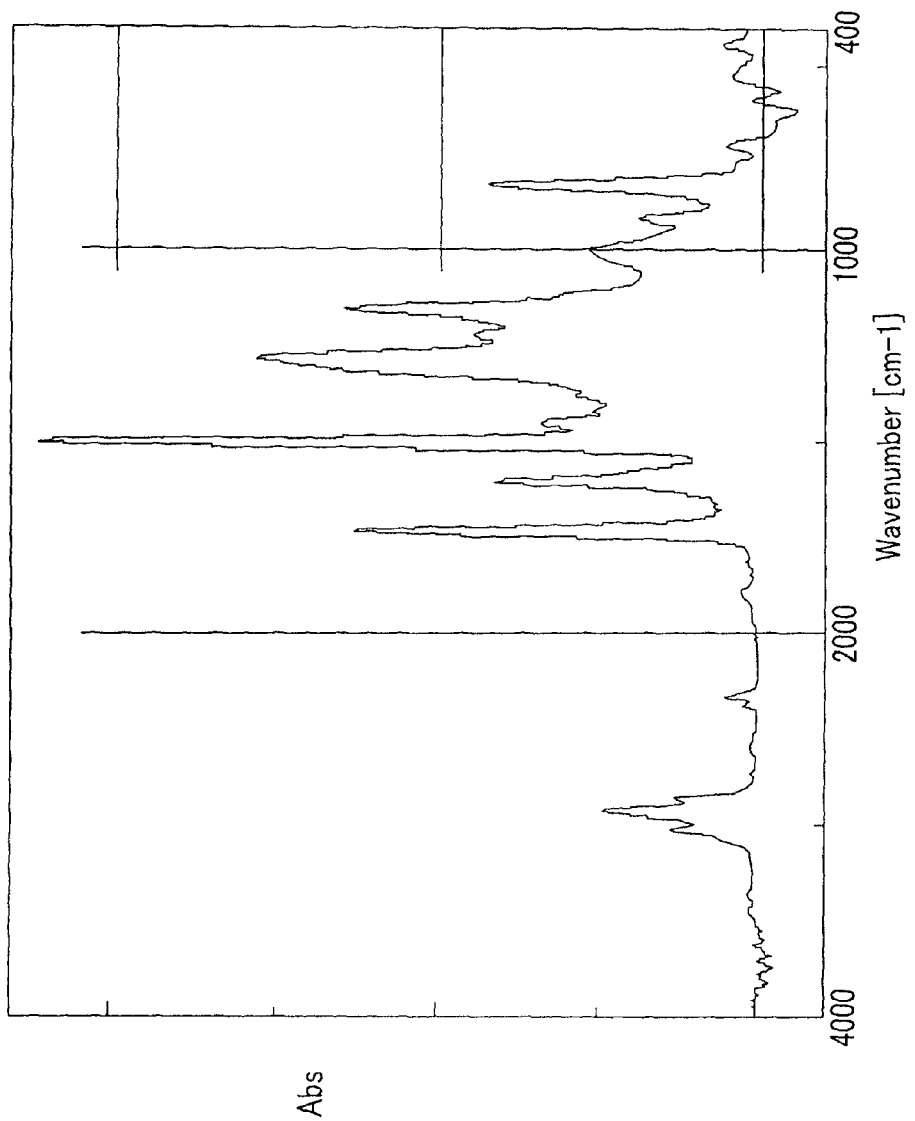
FIG. 9 is an IR spectrum of a compound (I)-27.

The IR spectrum of the obtained compound (I)-27 is shown in FIG. 9.

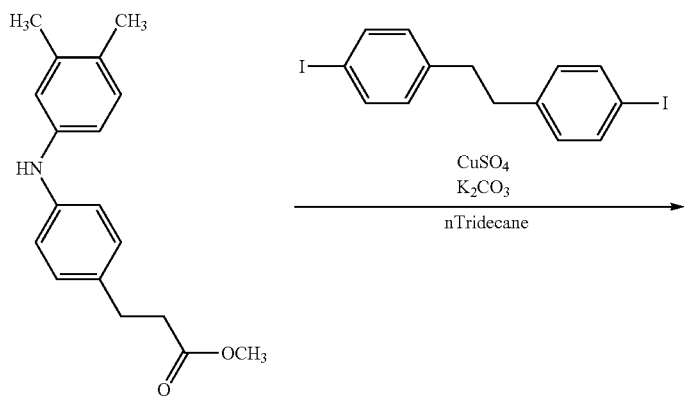

-continued

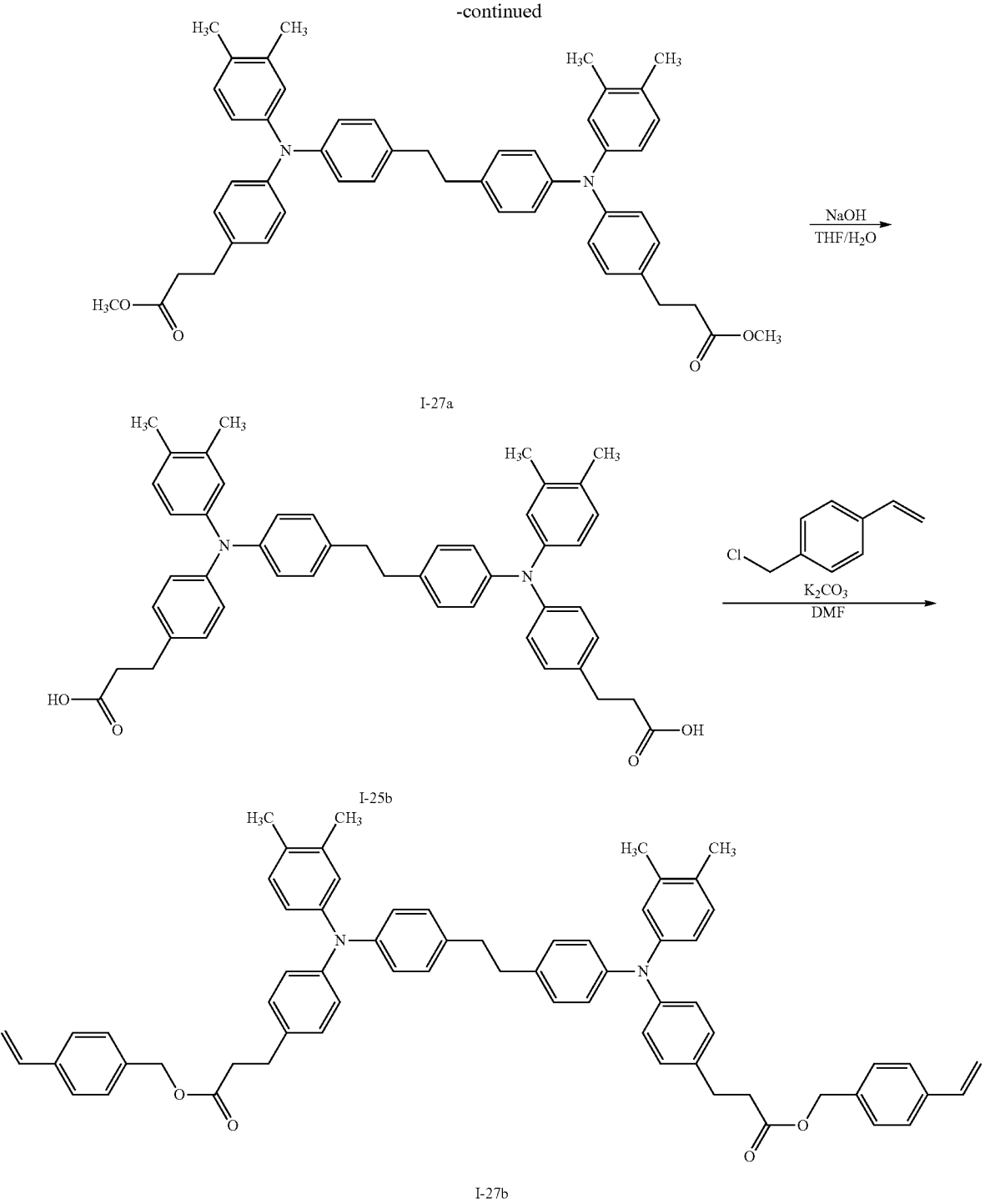

Synthesis Example 1-7

—Synthesis of Charge Transport Agent (I)-30 of Exemplary Embodiment of the Invention—

To a 500 ml three-neck flask, 66.3 g of methyl 3-[4-(4-phenyl)phenylaminophenyl]propionate, 43.4 g of 1,2-bis(4-iodophenyl)ethane, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 10 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 62.2 g of I-30a (yield 74%).

To a 3 L three-neck flask, 42.1 g of I-30a and 350 ml of tetrahydrofuran are added, and an aqueous solution obtained by dissolving 4.4 g of sodium hydroxide in 350 ml of water is added thereto, and this mixture is stirred for hours while being heated at 60° C. Thereafter, the reaction solution is added dropwise to an aqueous solution of water 1 L/concentrated hydrochloric acid 20 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 34.1 g of I-30b (yield 84%).

To a 500 ml three-neck flask, 28.5 g of I-30b, 11.8 g of 4-chloromethylstyrene, 10.6 g of potassium carbonate, 0.09 g of nitrobenzene, and 175 ml of DMF (N,N-dimethylformamide) are added, and this mixture is stirred for 5 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 26.7 g of a charge transport agent (I)-30 of the exemplary embodiment of the invention (yield 73%).

Figure 10:
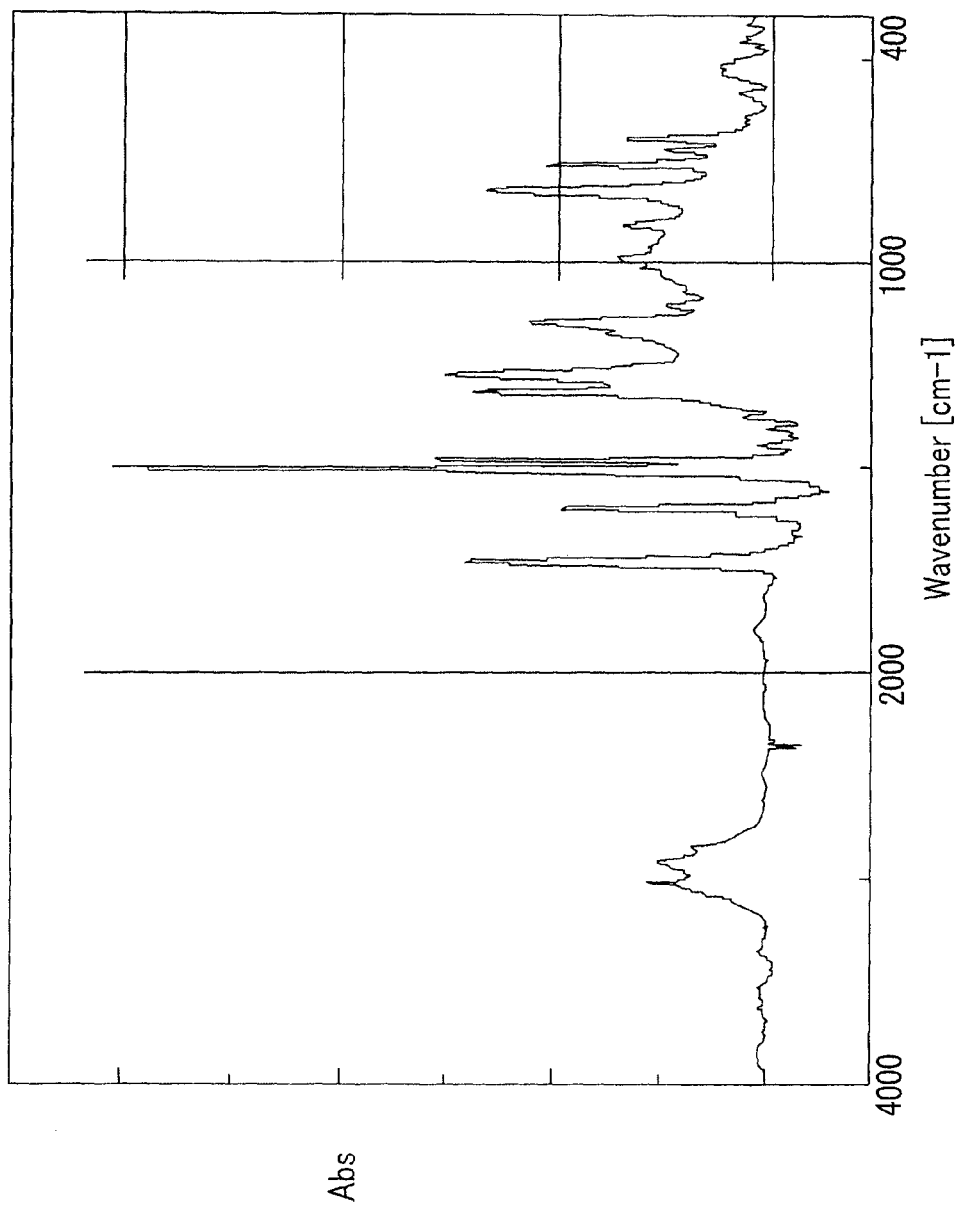
FIG. 10 is an IR spectrum of a compound (I)-30.

The IR spectrum of the obtained compound (I)-30 is shown in FIG. 10.

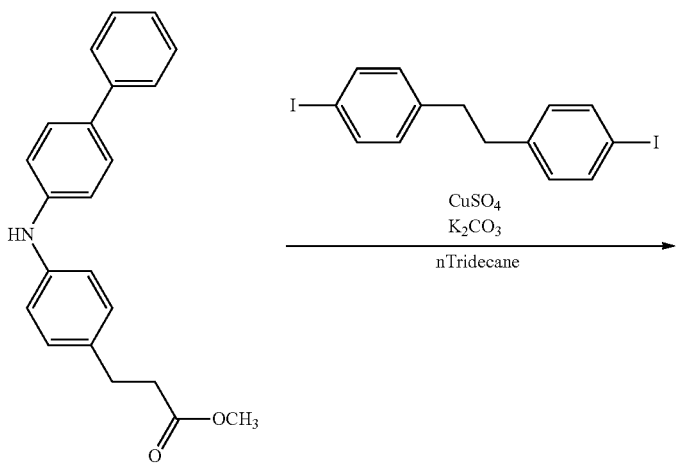

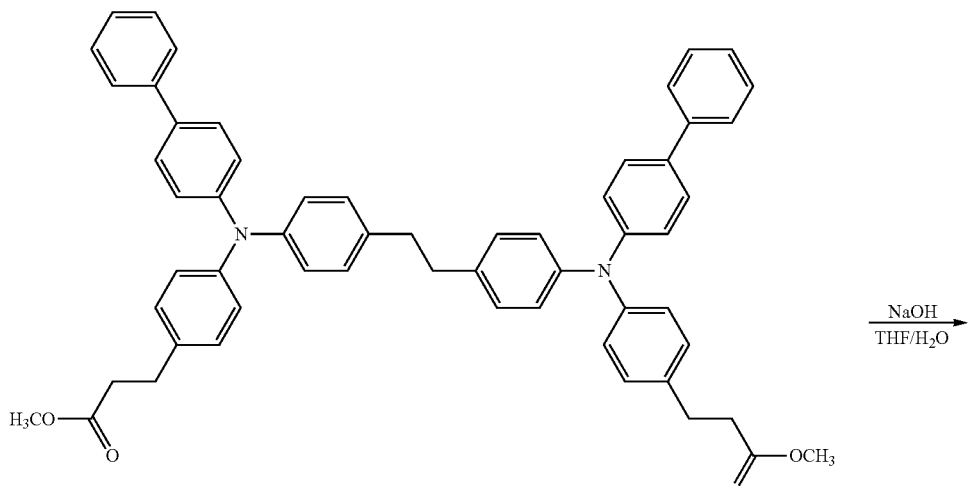

I-30a

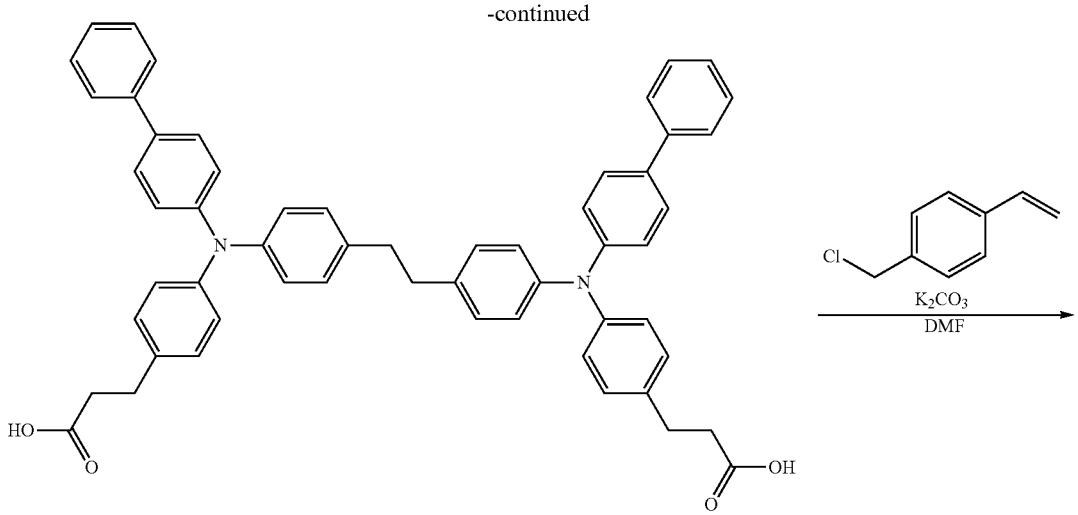

I-30b

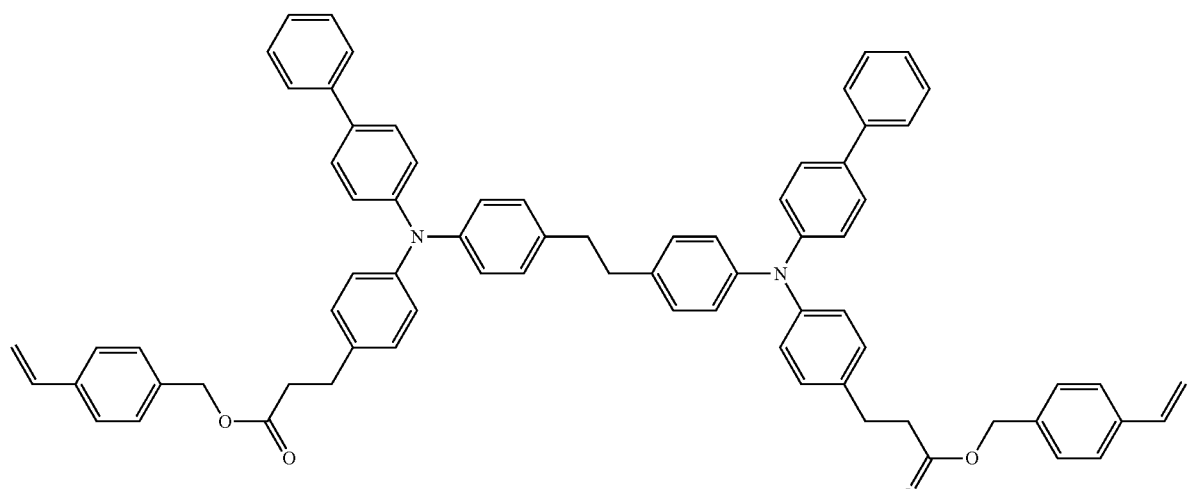

I-30

Synthesis Example 1-8

—Synthesis of Charge Transport Agent (I)-43 of Exemplary Embodiment of the Invention—

To a 500 ml three-neck flask, 68.3 g of 4,4'-bis(2-methoxycarbonylethyl)diphenylamine, 43.4 g of 4,4'-diiodo-3,3'-dimethyl-1,1'-biphenyl, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 10 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 56.0 g of I-43a (yield 65%).

To a 3 L three-neck flask, 43.1 g of I-43a and 350 ml of tetrahydrofuran are added, and an aqueous solution obtained by dissolving 8.8 g of sodium hydroxide in 350 ml of water is added thereto, and this mixture is stirred for hours while being heated at 60° C. Thereafter, the reaction solution is added dropwise to an aqueous solution of water 1 L/concentrated hydrochloric acid 40 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 36.6 g of I-43b (yield 91%).

To a 500 ml three-neck flask, 28.2 g of I-43b, 23.5 g of 4-chloromethylstyrene, 21.3 g of potassium carbonate, 0.09 g of nitrobenzene, and 175 ml of DMF (N,N-dimethylformamide) are added, and this mixture is stirred for 5 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 37.8 g of a charge transport agent (I)-43 of the exemplary embodiment of the invention (yield 85%).

Figure 11:
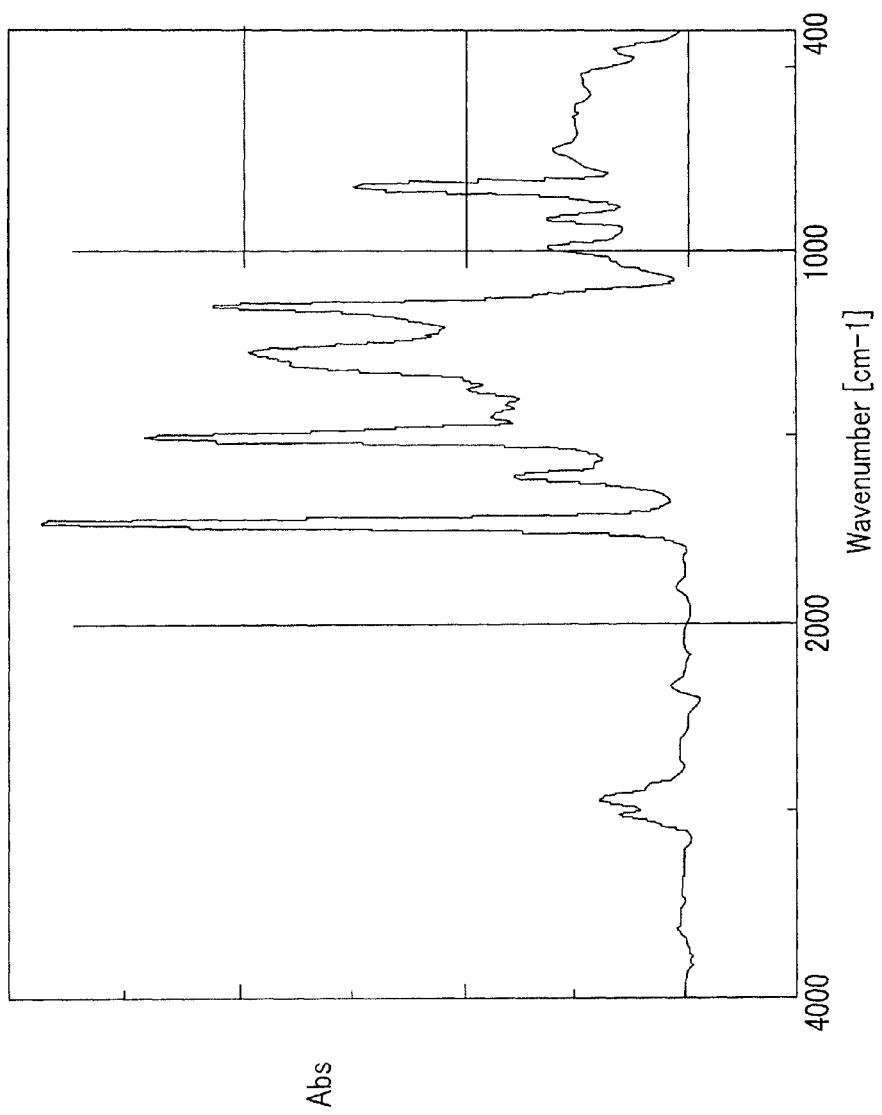
FIG. 11 is an IR spectrum of a compound (I)-43.

The IR spectrum of the obtained compound (I)-43 is shown in FIG. 11.
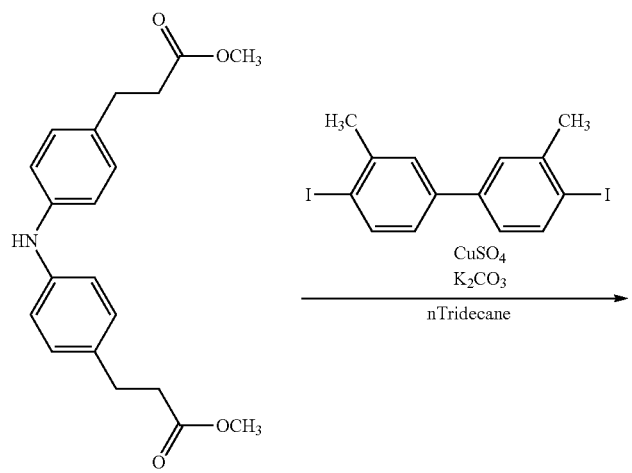
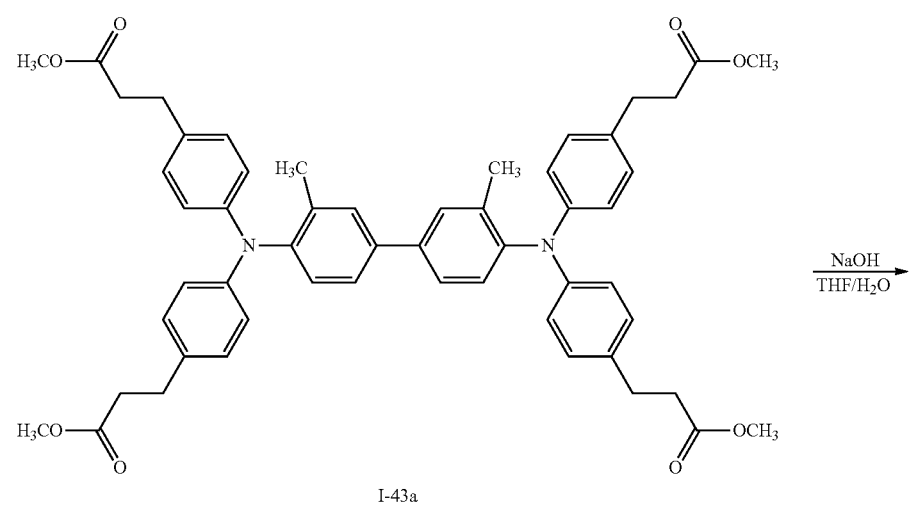
I-43a
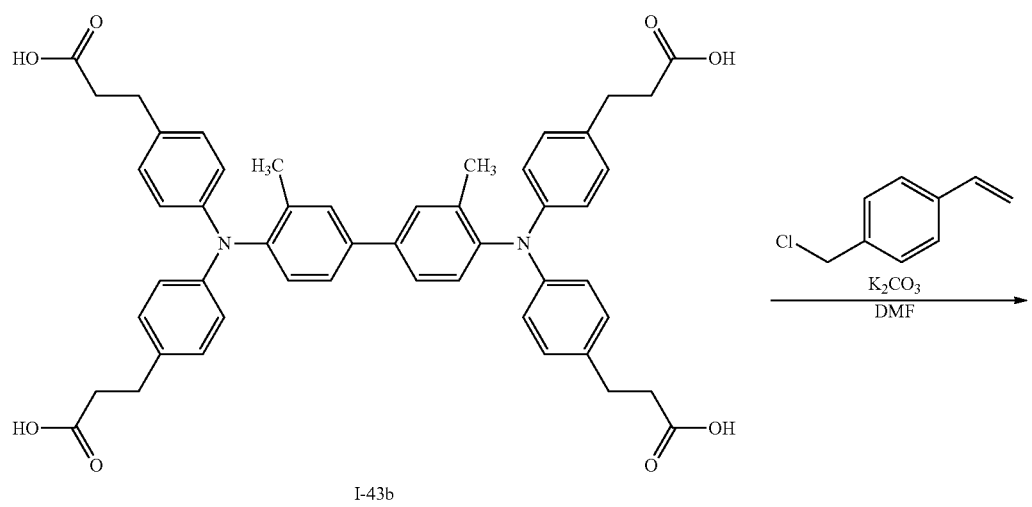
I-43b -continued

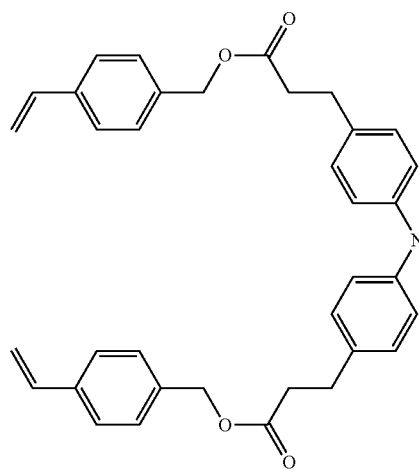
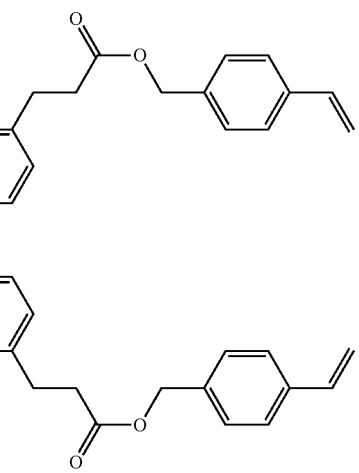

I-43

Synthesis Example 1-9

—Synthesis of Charge Transport Agent (I)-46 of Exemplary Embodiment of the Invention—

To a 3 L three-neck flask, 43.1 g of I-43a and 300 ml of tetrahydrofuran are added, followed by stirring. The reaction system is substituted with nitrogen, and then 16.3 g of sodium borohydride is added thereto. Thereafter, 50 ml of methanol is added dropwise thereto over 2 hours under heating and refluxing. After the mixture is heated and refluxed for another 2 hours, the temperature is temporarily cooled to 0° C., 300 ml of 2N hydrochloric acid is added dropwise thereto over an hour, and the temperature is slowly increased to room temperature again. Subsequently, liquid separation is performed by adding 400 ml of ethyl acetate, and an ethyl acetate layer is collected. 10 g of sodium sulfate is added thereto, followed by stirring for 10 minutes, and then the sodium sulfate is filtered. A crude product obtained after distilling away ethyl acetate under reduced pressure is purified through silica gel column chromatography by using toluene/ethyl acetate as an eluent, thereby obtaining 28.5 g of I-46a (yield 76%).

To a 500 ml three-neck flask, 26.2 g of I-46a, 14.9 g of succinic anhydride, and 70 ml of tetrahydrofuran are added. While this mixture is stirred under nitrogen flow, 14.9 g of triethylamine and 0.2 g of N,N-dimethylaminopyridine are added thereto, followed by stirring for another 2 hours. Thereafter, 200 ml of 1N hydrochloric acid and 300 ml of ethyl acetate are added thereto, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 35.0 g of I-46b (yield 87%).

To a 500 ml three-neck flask, 23.0 g of I-46b, 13.4 g of 4-chloromethylstyrene, 12.2 g of potassium carbonate, 0.05 g of nitrobenzene, and 100 ml of DMF (N,N-dimethylformamide) are added, and this mixture is stirred for 5 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 26.1 g of a charge transport agent (I)-46 of the exemplary embodiment of the invention (yield 81%).

Figure 12:
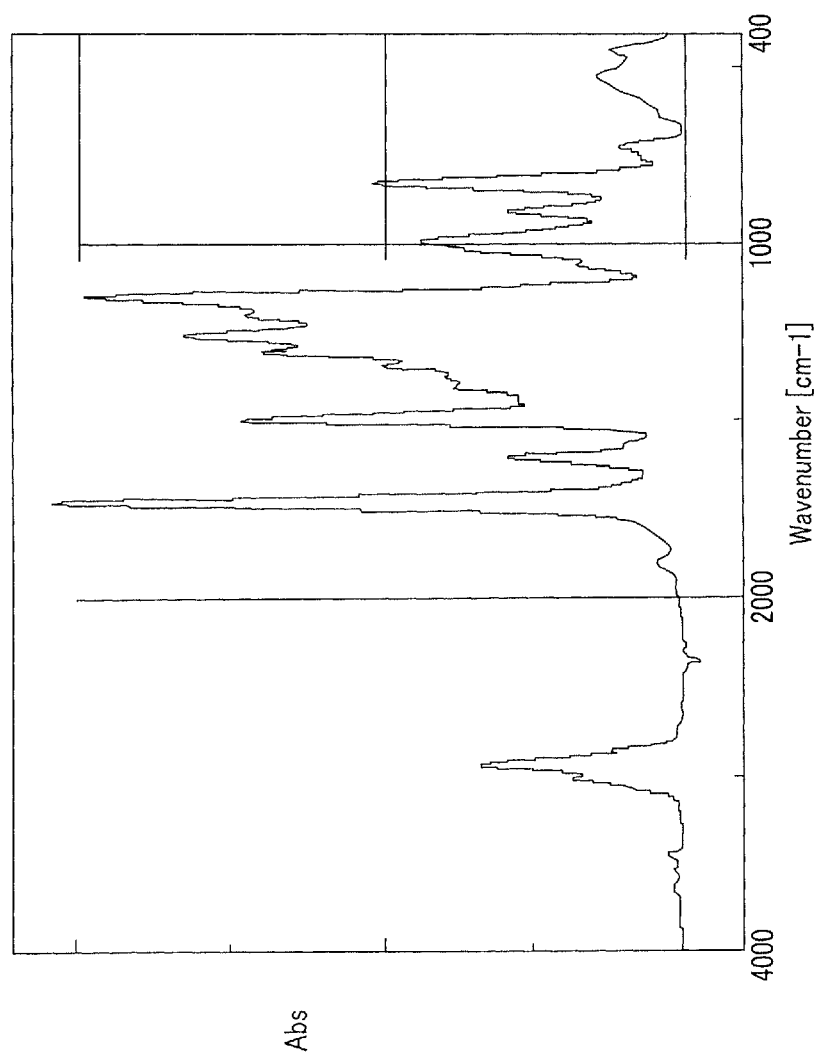
FIG. 12 is an IR spectrum of a compound (I)-46.

The IR spectrum of the obtained compound (I)-46 is shown in FIG. 12.

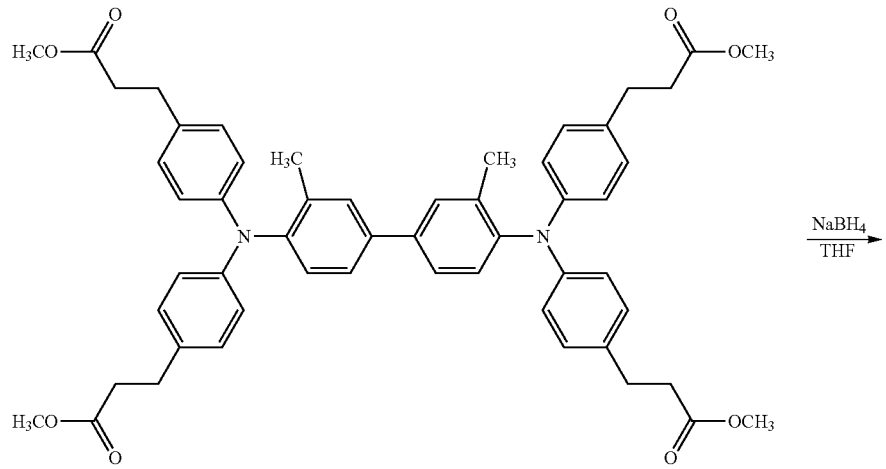

I-43a

-continued
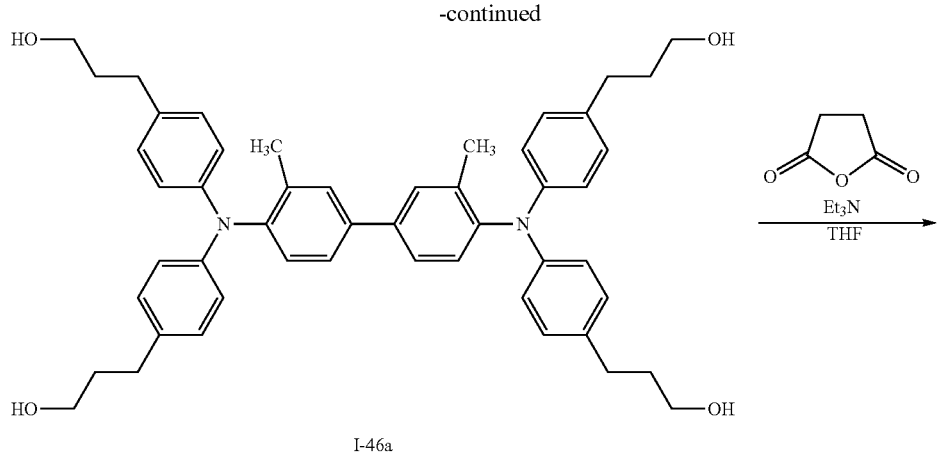
I-46a
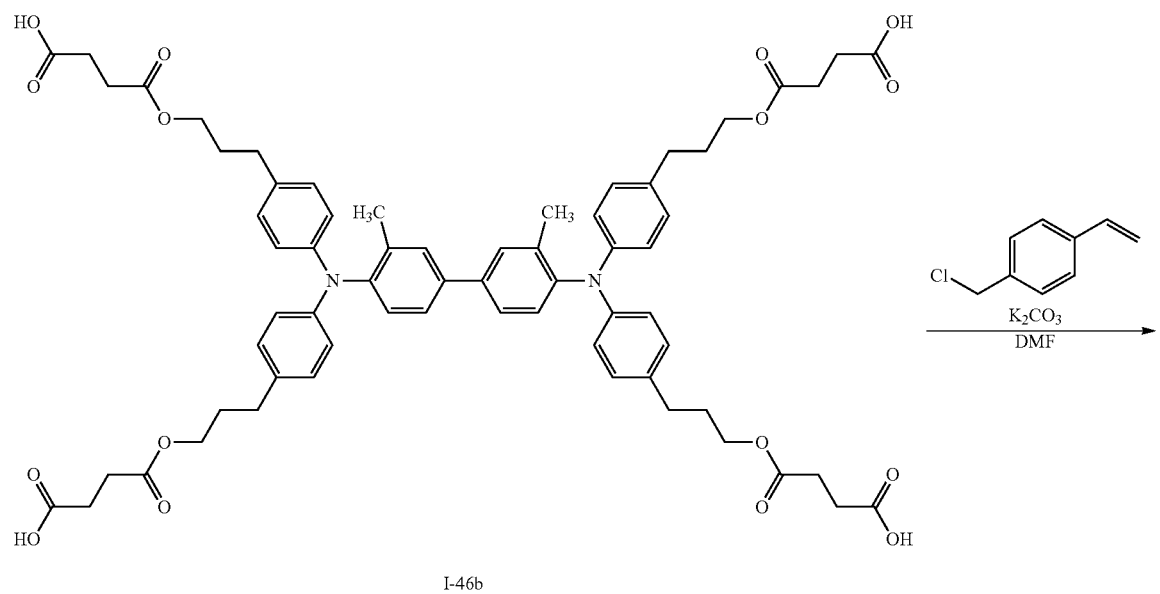
I-46b
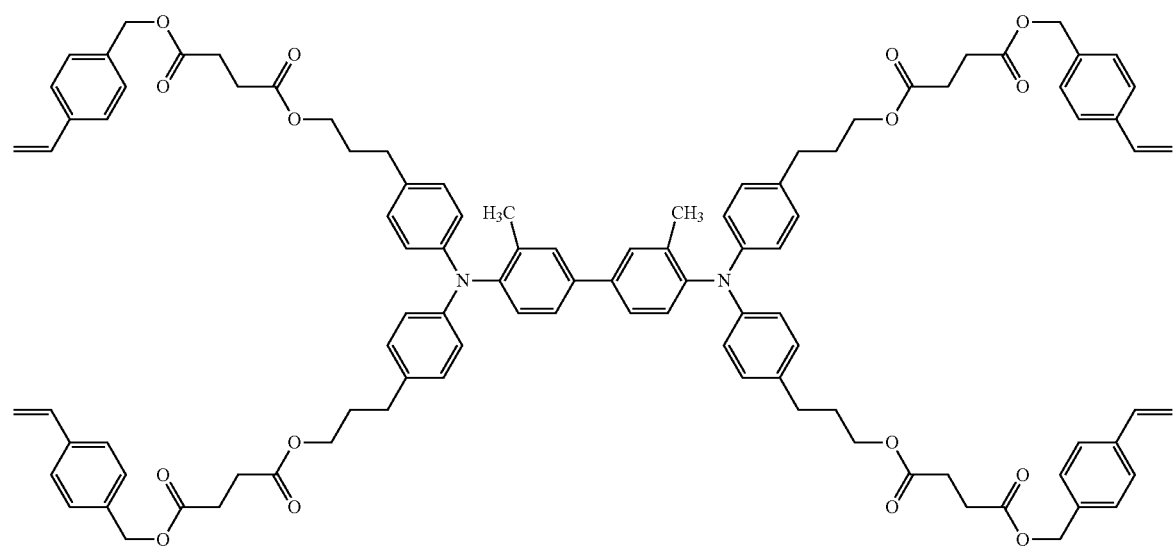
I-46

Synthesis Example 1-10

—Synthesis of Charge Transport Agent (I)-53 of Exemplary Embodiment of the Invention—

To a 500 ml three-neck flask, 68.3 g of 4,4'-bis(2-methoxycarbonylethyl)diphenylamine, 43.4 g of 1,2-bis(4-iodophenyl)ethane, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 10 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 59.4 g of I-53a (yield 69%).

To a 3 L three-neck flask, 43.1 g of I-53a and 350 ml of tetrahydrofuran are added, and an aqueous solution obtained by dissolving 8.8 g of sodium hydroxide in 350 ml of water is added thereto, and this mixture is stirred for hours while being heated at 60° C. Thereafter, the reaction solution is added dropwise to an aqueous solution of water 1 L/concentrated hydrochloric acid 40 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 34.2 g of I-53b (yield 85%).

To a 500 ml three-neck flask, 28.2 g of I-53b, 23.5 g of 4-chloromethylstyrene, 21.3 g of potassium carbonate, 0.09 g of nitrobenzene, and 175 ml of DMF (N,N-dimethylformamide) are added, and this mixture is stirred for 5 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 35.1 g of a charge transport agent (I)-53 of the exemplary embodiment of the invention (yield 79%).

Figure 13:
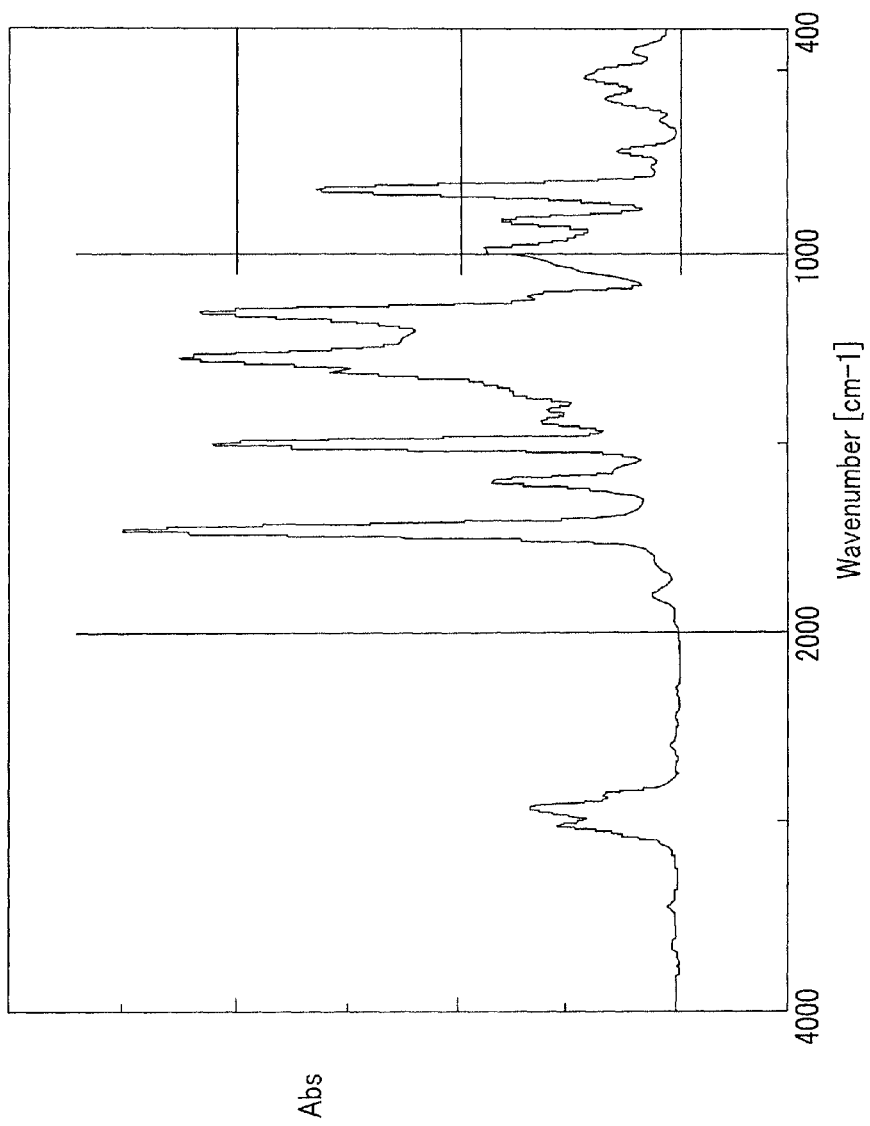
FIG. 13 is an IR spectrum of a compound (I)-53.
Figure 14:
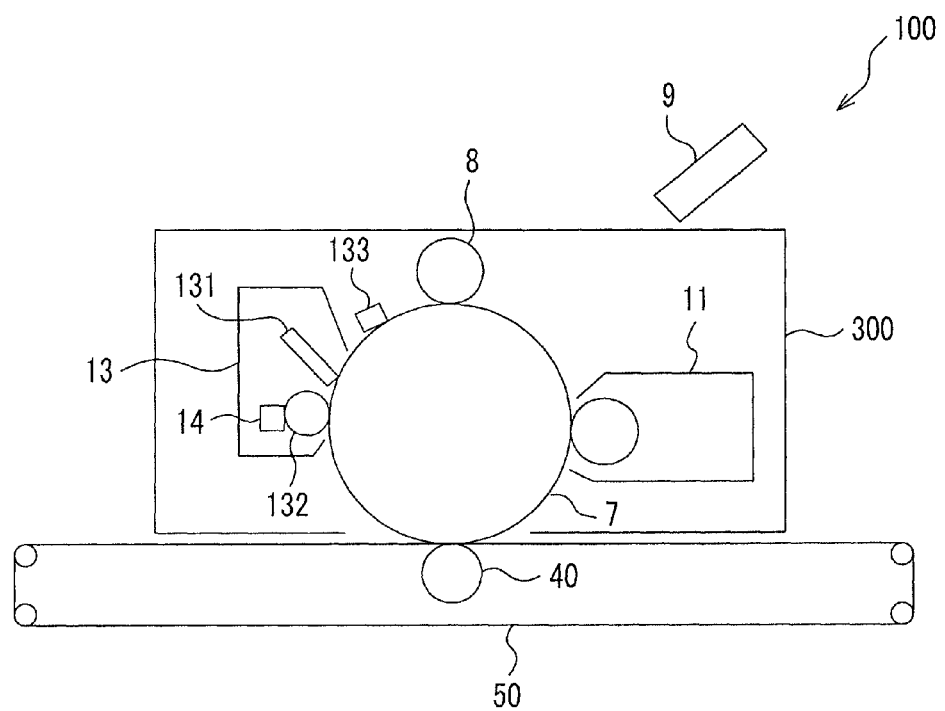
FIG. 14 is a schematic configuration view showing an image forming apparatus according to the exemplary embodiment.
Figure 15:
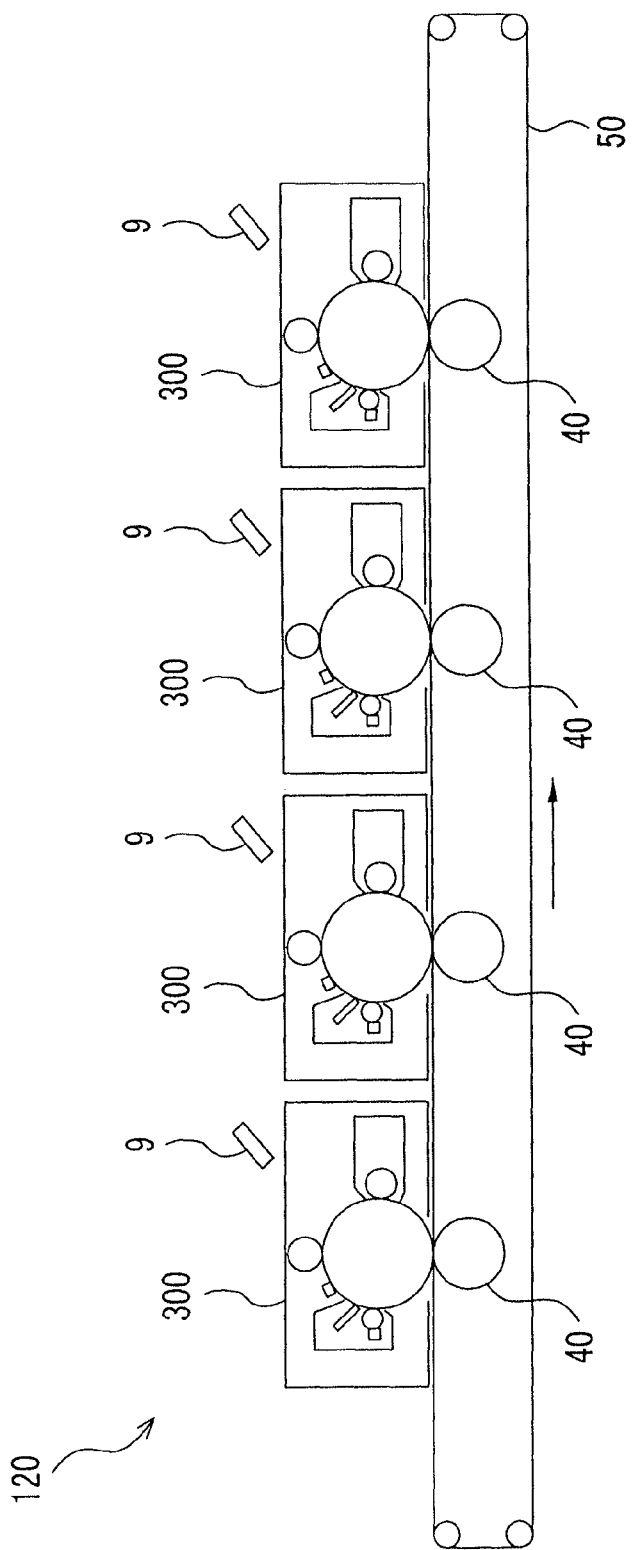
FIG. 15 is a schematic configuration view showing an image forming apparatus according to another exemplary embodiment.

The IR spectrum of the obtained compound (I)-53 is shown in FIG. 13.

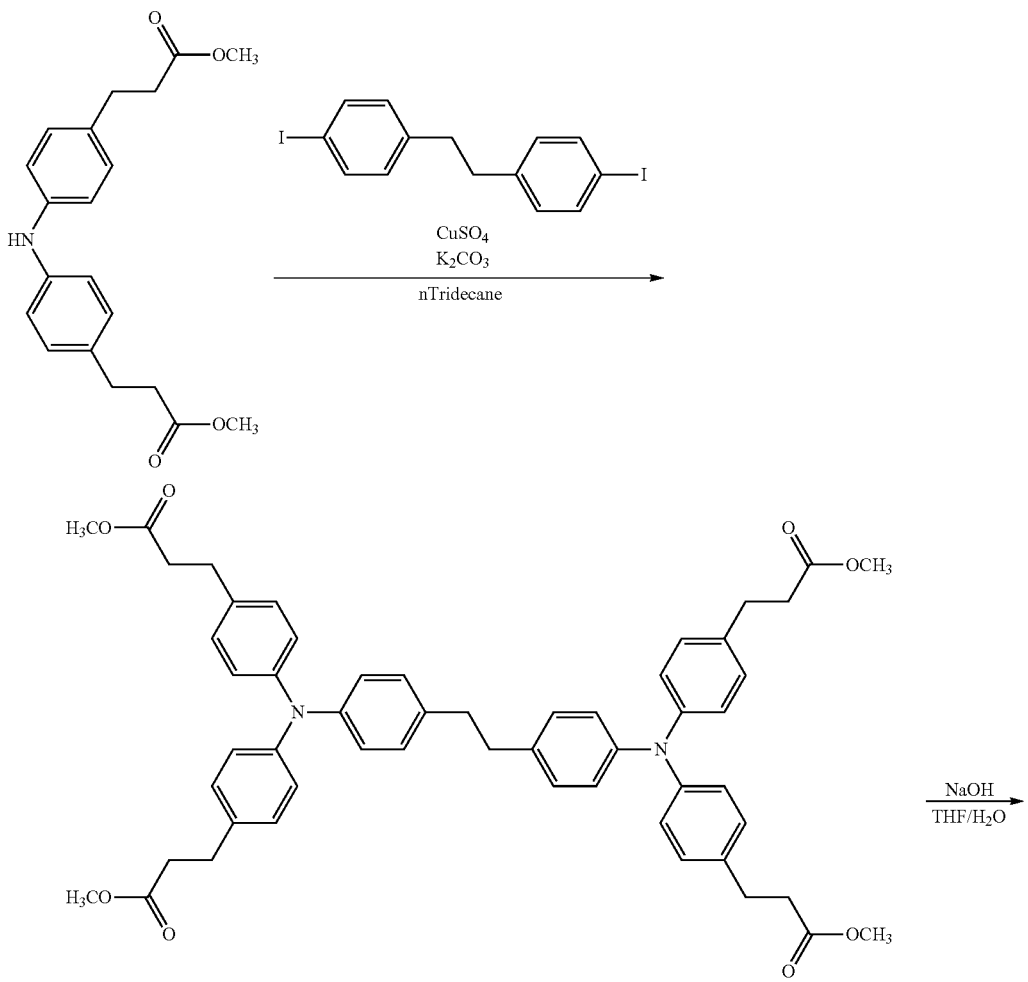

I-53a

-continued
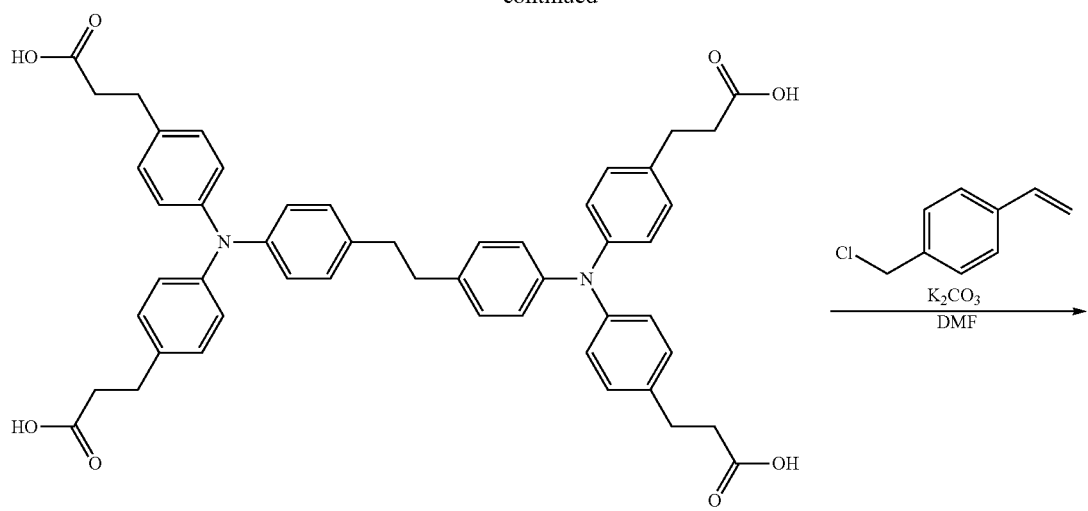
I-53b
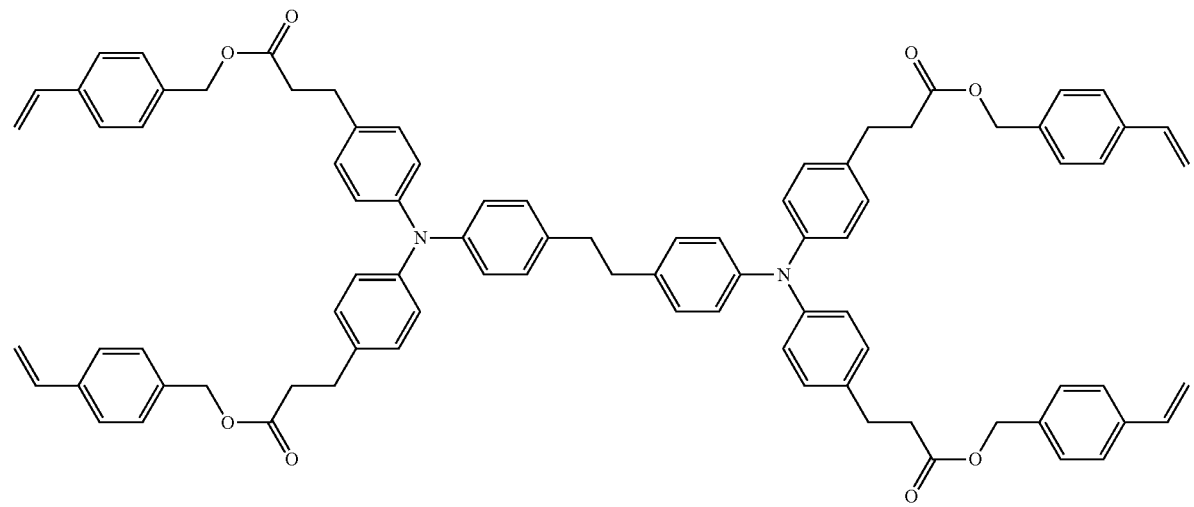
I-53

Example 1-1

—Preparation of Charge Transporting Film—

A coating liquid for forming a charge transporting film having the following composition is prepared.

(Charge Transport Agent)

The charge transport material ((I)-15) synthesized in the Synthesize Example 1-1: 100 parts by weight (Initiator)

V-601 (manufactured by Wako Pure Chemical Industries, Ltd.): 2 parts by weight (Solvent)

Mixed solvent of tetrahydrofuran (THF)/toluene (volume ratio of 40/60): 150 parts by weight

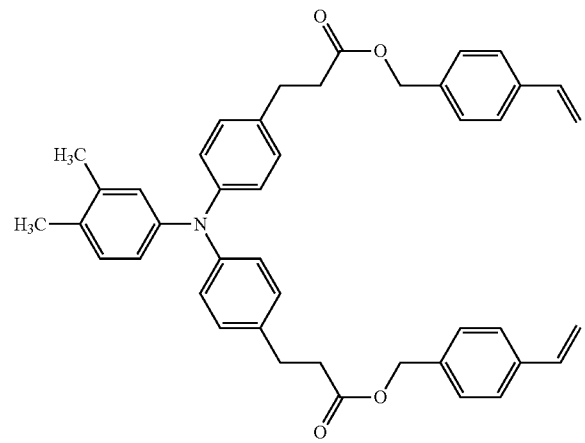

(I)-15

An ITO glass substrate that includes an ITO film on a glass substrate is prepared, and the ITO film is etched into an approximately strip shape having a width of 2 mm, thereby forming an ITO electrode (anode). This ITO glass substrate is subjected to ultrasonic cleaning by using isopropanol (used in the field of electronic industry, manufactured by Kanto Chemical Co., Inc.) and then dried using a spin coater.

In the ITO glass substrate, the coating liquid for forming a charge transporting film is coated onto the surface where the ITO electrode has been formed, and the resultant is heated at 150° C. for 40 minutes in an atmosphere in which an oxygen concentration of about 100 ppm, thereby forming a 5 μm charge transporting film 1-1.

(Measurement of Mobility Stability)

30 V/μm of an electric field is created for the charge transporting film by using TOF-401 (manufactured by Sumitomo Heavy Industries, Ltd.), and mobility is repeatedly measured 100 times, and the mobility stability is evaluated from the following formula.

"||" indicates an absolute value, and A++ indicates the best characteristic.

Mobility stability=|(mobility measured firstly)−(mobility measured by the 100$^{th}$ measurement)|/(mobility measured firstly)

A++: less than 0.05
A+: 0.05 or more and less than 0.08
A: 0.08 or more and less than 0.1
B: 0.1 or more and less than 0.2
C: 0.2 or more —Preparation of Organic Electroluminescence Element—

An ITO glass substrate that includes an ITO film on a glass substrate is prepared, and the ITO film is etched into an approximately strip shape having a width of 2 mm, thereby forming an ITO electrode (anode). This ITO glass substrate is subjected to ultrasonic cleaning by using isopropanol (used in the field of electronic industry, manufactured by Kanto Chemical Co., Inc.) and then dried using a spin coater.

Thereafter, in the ITO glass substrate, copper phthalocyanine prepared by sublimation is vacuum-deposited onto the surface where the ITO electrode is formed, thereby forming a thin film having a thickness of 0.015 μm.

The coating liquid for forming a charge transporting film is coated onto the copper phthalocyanine film, followed by heating at 145° C. for 40 minutes in an atmosphere in which an oxygen concentration of about 100 ppm, thereby forming a 0.05 μm thin film. In this manner, a hole transporting layer having a double-layer structure is formed on the ITO electrode.

Subsequently, on the hole transporting layer, tris(8-hydroxyquinoline)aluminum (Alq) is vapor-deposited as a luminous material, thereby forming a luminous layer having a thickness of 0.060 μm.

In addition, on the luminous layer, a Mg—Ag alloy is vapor-deposited by codeposition, thereby forming a Mg—Ag electrode (cathode) with an approximately strip shape having a width of 2 mm and a thickness of 0.13 μm. In this manner, an organic electroluminescence element 1-1 is obtained. The ITO electrode and Mg—Ag electrode are formed such that these electrodes extend at right angles to each other. An effective area of the obtained organic electroluminescence element 1-1 is 0.04 cm$^2$.

Comparative Example 1-1

A comparative charge transporting film 1-1 and a comparative organic electroluminescence element 1-1 are obtained in the same manner as that in Example 1-1, except that the charge transport material (I-15) is changed to a comparative compound (AC-1) having the following structure. The resultant is taken as the comparative electroluminescence element 1-1.

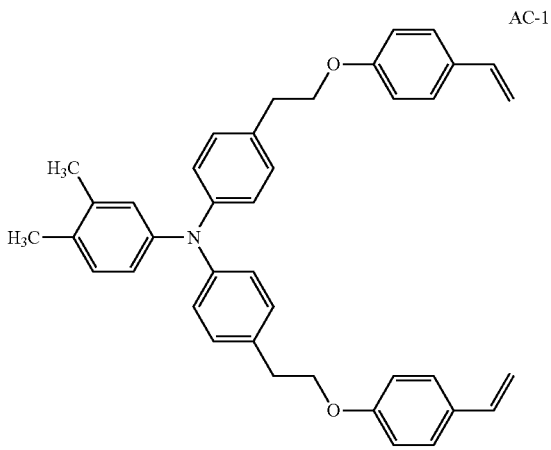 [SMILES: C=Cc1ccc(OCCc2ccc(N(c3ccc(CCOc4ccc(C=C)cc4)cc3)c3ccc(C)c(C)c3)cc2)cc1]

AC-1

Comparative Example 1-2

A comparative charge transporting film 1-2 and a comparative organic electroluminescence element 1-2 are obtained in the same manner as that in Example 1-1, except that the charge transport material (I-15) is changed to a comparative compound (AC-2) having the following structure. The resultant is taken as the comparative electroluminescence element 1-2.

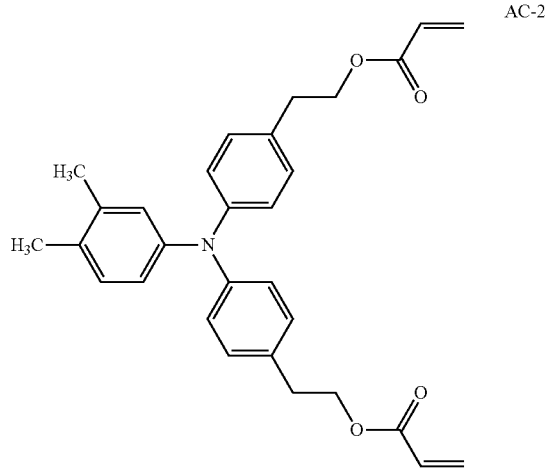 [SMILES: C=CC(=O)OCCc1ccc(N(c2ccc(CCOC(=O)C=C)cc2)c2ccc(C)c(C)c2)cc1]

AC-2

Examples 1-2 to 1-16

Charge transporting films 1-2 to 1-16 and organic electroluminescence elements 1-2 to 1-16 are obtained in the same manner as that in Example 1-1, except that the charge transport material, the initiator, and the solvent in Example 1-1 are changed to those described in Table 7.

(Element Characteristic Evaluation)

The characteristics of the organic electroluminescence elements obtained in examples and comparative examples are evaluated in the following manner.

<Maximum Luminance>

In vacuum (0.125 Pa), the ITO electrode is used as a positive electrode (anode), and the MG-Ag electrode is used as a negative electrode (cathode). DC voltage is applied to these electrodes so as to cause the electrodes to emit light, and the maximum luminance at this time is evaluated. The results are shown in Table 7.

The evaluation criteria of the maximum luminance are as follows (the unit of numerical values is $cd/m^2$), and A++ indicates the best characteristic.

A++: 800 or more
A+: 750 or more and less than 800
A: 700 or more and less than 750
B: 650 or more and less than 700
C: less than 650

<Element Lifetime>

The emission lifetime of the organic electroluminescence element in dry nitrogen is measured in the following manner.

The element life time is evaluated by using a relative time obtained when the initial luminance in a DC driving mode at room temperature is set to 500 $cd/m^2$, and a driving time at a point of time when the luminance (initial luminance L0: 500 $cd/m^2$) of the element of Comparative Example 1-1 becomes (luminance L/initial luminance L0)=0.5 is set to 1.0, and using voltage rise amount (=voltage/initial driving voltage) at a point of time when the luminance of the element becomes (luminance L/initial luminance L0)=0.5.

The evaluation criteria of the relative time (L/L0=0.5) and the voltage rise (at the time when L/L0=0.5) are as follows.

Relative Time (L/L0=0.5)
A++ indicates the best characteristic.
A++: 1.6 or more
A+: 1.4 or more and less than 1.6
A: 1.2 or more and less than 1.4
B: 1.0 or more and less than 1.2
C: less than 1.0

Voltage Rise (at the Time when L/L0=0.5)
A++ indicates the best characteristic.
A++: 1.0 or more and less than 1.1
A+: 1.1 or more and less than 1.2
A: 1.2 or more and less than 1.3
B: 1.3 or more and less than 1.4
C: 1.4 or more

TABLE 7

| | Novel reactive compound of the exemplary embodiment of the invention | Initiator | Solvent Numerical Weight ratio in ( ) | Characteristics of charge transporting film Mobility stability | Characteristics of organic electroluminescence element | | |
|---|---|---|---|---|---|---|---|
| | | | | | Maximum luminance | Voltage rise (@L/L0 = 0.5) | Relative time (L/L0 = 0.5) |
| Example 1 | I-15 | V-601 | THF/toluene (40/60) | A | A | A | A |
| Comparative Example 1 | AC-1 | V-601 | THF/toluene (40/60) | B | B | B | A |
| Comparative Example 2 | AC-2 | V-601 | THF/toluene (40/60) | C | C | B | C |
| Example 2 | I-17 | V-601 | THF/toluene (40/60) | A | A | A | A |
| Example 3 | I-23 | V-601 | THF/toluene (40/60) | A+ | A+ | A | A |
| Example 4 | I-25 | V-601 | THF/toluene (40/60) | A | A | A | A |
| Example 5 | I-27 | V-601 | THF/toluene (40/60) | A+ | A+ | A | A |
| Example 6 | I-30 | V-601 | THF/toluene (40/60) | A+ | A+ | A | A |
| Example 7 | I-43 | V-601 | THF/toluene (40/60) | A++ | A+ | A+ | A+ |
| Example 8 | I-46 | V-601 | THF/toluene (40/60) | A+ | A | A | A+ |
| Example 9 | I-53 | V-601 | THF/toluene (40/60) | A++ | A+ | A+ | A+ |
| Example 10 | I-43/I-61 (Weight ratio 95/5) | V-601 | THF/toluene (40/60) | A++ | A+ | A+ | A+ |
| Example 11 | I-15 | VE-073 | THF/toluene (50/50) | A | A | A | A |
| Example 12 | I-43 | OTazo | THF/toluene (40/60) | A++ | A+ | A+ | A+ |
| Example 13 | I-17 | V-601 | n-butyl acetate | A | A | A | A |
| Example 14 | I-53 | V-601 | Methyl i-butyl ketone | A++ | A+ | A+ | A+ |
| Example 15 | I-53/I-7 | V-601 | THF/toluene (20/80) | A++ | A+ | A+ | A+ |

TABLE 7-continued

| Novel reactive compound of the exemplary embodiment of the invention | Initiator | Solvent Numerical Weight ratio in ( ) | Characteristics of charge transporting film Mobility stability | Characteristics of organic electroluminescence element | | |
|---|---|---|---|---|---|---|
| | | | | Maximum luminance | Voltage rise (@L/L0 = 0.5) | Relative time (L/L0 = 0.5) |
| Example 16 | (Weight ratio 75/25) I-43/I-7 (Weight ratio 70/30) | V-601 | THF/toluene (30/70) | A++ | A+ | A+ | A+ |

VE-073: polymerization initiator (manufactured by Wako Pure Chemical Industries, Ltd.)

OTazo-15: polymerization initiator (manufactured by Otsuka Chemical Co., Ltd.)

Synthesis Example 2-1

—Synthesis of Charge Transport Agent (I')-15 of Exemplary Embodiment of the Invention—

To a 500 ml three-neck flask, 68.3 g of 4,4'-bis(2-methoxycarbonylethyl)diphenylamine, 46.4 g of 4-iodoxylene, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 20 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 65.1 g of I'-15a (yield 73%).

To a 3 L three-neck flask, 59.4 g of I'-15a and 450 ml of tetrahydrofuran are added, and an aqueous solution obtained by dissolving 11.7 g of sodium hydroxide in 450 ml of water is added thereto, followed by stirring at 60° C. for 3 hours. Thereafter, the reaction solution is added dropwise to an aqueous solution of water 1 L/concentrated hydrochloric acid 60 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 46.2 g of I'-15b (yield 83%).

To a 500 ml three-neck flask, 29.2 g of I'-15b, 23.5 g of 4-chloromethylstyrene, 21.3 g of potassium carbonate, 0.17 g of nitrobenzene, and 175 ml of DMF (N,N-dimethylformamide) are added, and this mixture is stirred for 3 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 36.4 g of a charge transport agent (I')-15 of the exemplary embodiment of the invention (yield 80%).

Figure 17:
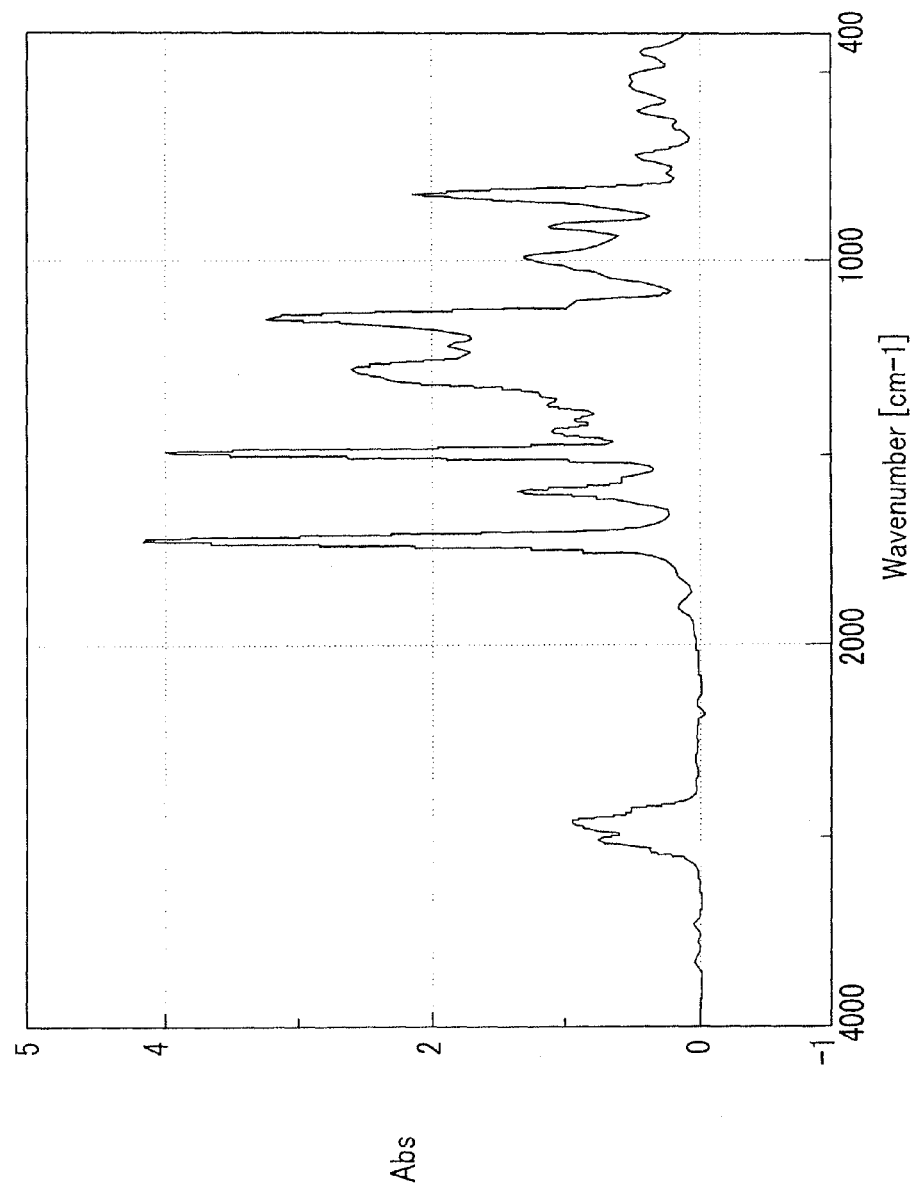
FIG. 17 is an IR spectrum of a compound (I')-15.

The IR spectrum of the obtained compound (I')-15 is shown in FIG. 17.

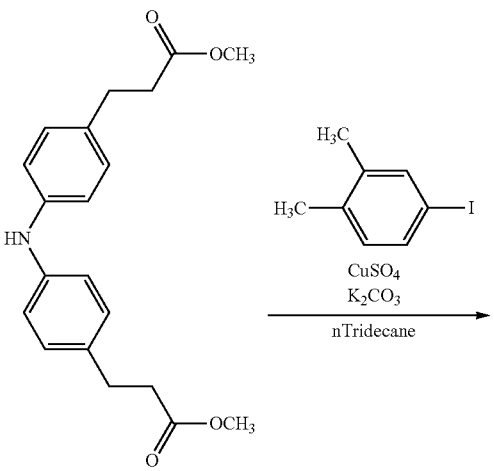

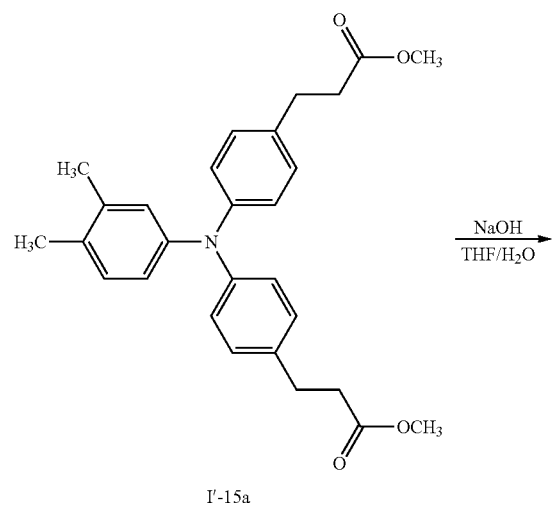

I'-15a

-continued

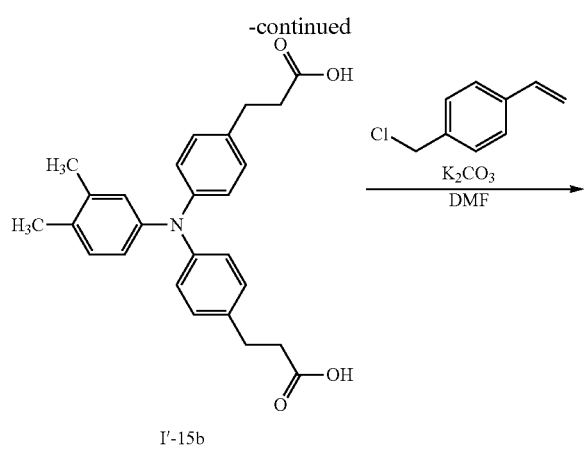

I'-15b

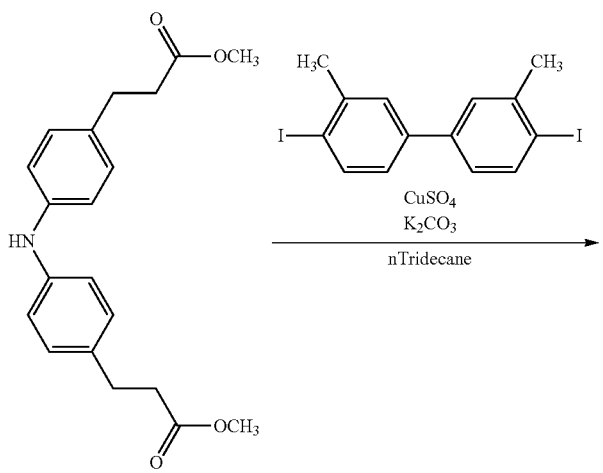

I'-15

Synthesis Example 2-2

—Synthesis of Charge Transport Agent (I')-43 of Exemplary Embodiment of the Invention—

To a 500 ml three-neck flask, 68.3 g of 4,4'-bis(2-methoxycarbonylethyl)diphenylamine, 43.4 g of 4,4'-diiodo-3,3'-dimethyl-1,1'-biphenyl, 30.4 g of potassium carbonate, 1.5 g of copper sulfate pentahydrate, and 50 ml of n-tridecane are added, and this mixture is stirred for 20 hours while being heated at 220° C. under nitrogen flow. Thereafter, the temperature is reduced to room temperature, and 200 ml of toluene and 150 ml of water are added thereto, thereby performing liquid separation. A toluene layer is collected, 10 g of sodium sulfate is added thereto, followed by stirring for 10 minutes, and then the sodium sulfate is filtered. A crude product obtained after distilling away toluene under reduced pressure is purified through silica gel column chromatography by using toluene/ethyl acetate as an eluent, thereby obtaining 56.0 g of I'-43a (yield 65%).

To a 3 L three-neck flask, 43.1 g of I'-43a and 350 ml of tetrahydrofuran are added, and an aqueous solution obtained by dissolving 8.8 g of sodium hydroxide in 350 ml of water is added thereto, and this mixture is stirred for hours while being heated at 60° C. Thereafter, the reaction solution is added dropwise to an aqueous solution of water 1 L/concentrated hydrochloric acid 40 ml, and the precipitated solid is collected by suction filtration. This solid is added to a 50 ml of mixed solvent of acetone/water (volume ratio of 40/60) and stirred while being suspended, and then collected by suction filtration, followed by vacuum drying for 10 hours, thereby obtaining 36.6 g of I'-43b (yield 91%).

To a 500 ml three-neck flask, 28.2 g of I'-43b, 23.5 g of 4-chloromethylstyrene, 21.3 g of potassium carbonate, 0.09 q of nitrobenzene, and 175 ml of DMF (N,N-dimethylformamide) are added, and this mixture is stirred for 5 hours while being heated at 75° C. under nitrogen flow. Thereafter, the temperature is reduced to room temperature, and ethyl acetate 200 ml/water 200 ml are added to the reaction solution, thereby performing liquid separation. An ethyl acetate layer is collected, 10 g of sodium sulfate is added thereto, followed by stirring for 10 minutes, and then the sodium sulfate is filtered. A crude product obtained after distilling away the ethyl acetate under reduced pressure is purified through silica gel column chromatography by using toluene/ethyl acetate as an eluent, thereby obtaining 37.8 g of a charge transport agent (I')-43 of the exemplary embodiment of the invention (yield 85%).

Figure 18:
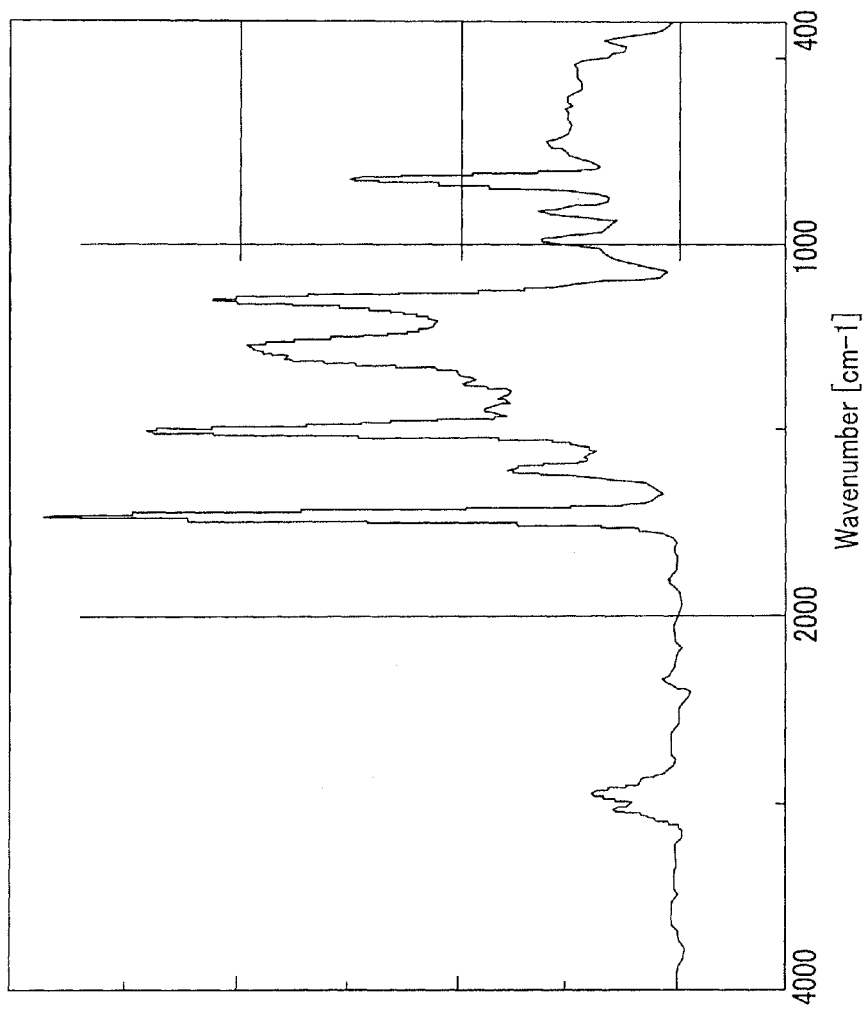
FIG. 18 is an IR spectrum of a compound (I')-43.

The IR spectrum of the obtained compound (I')-43 is shown in FIG. 18.

-continued

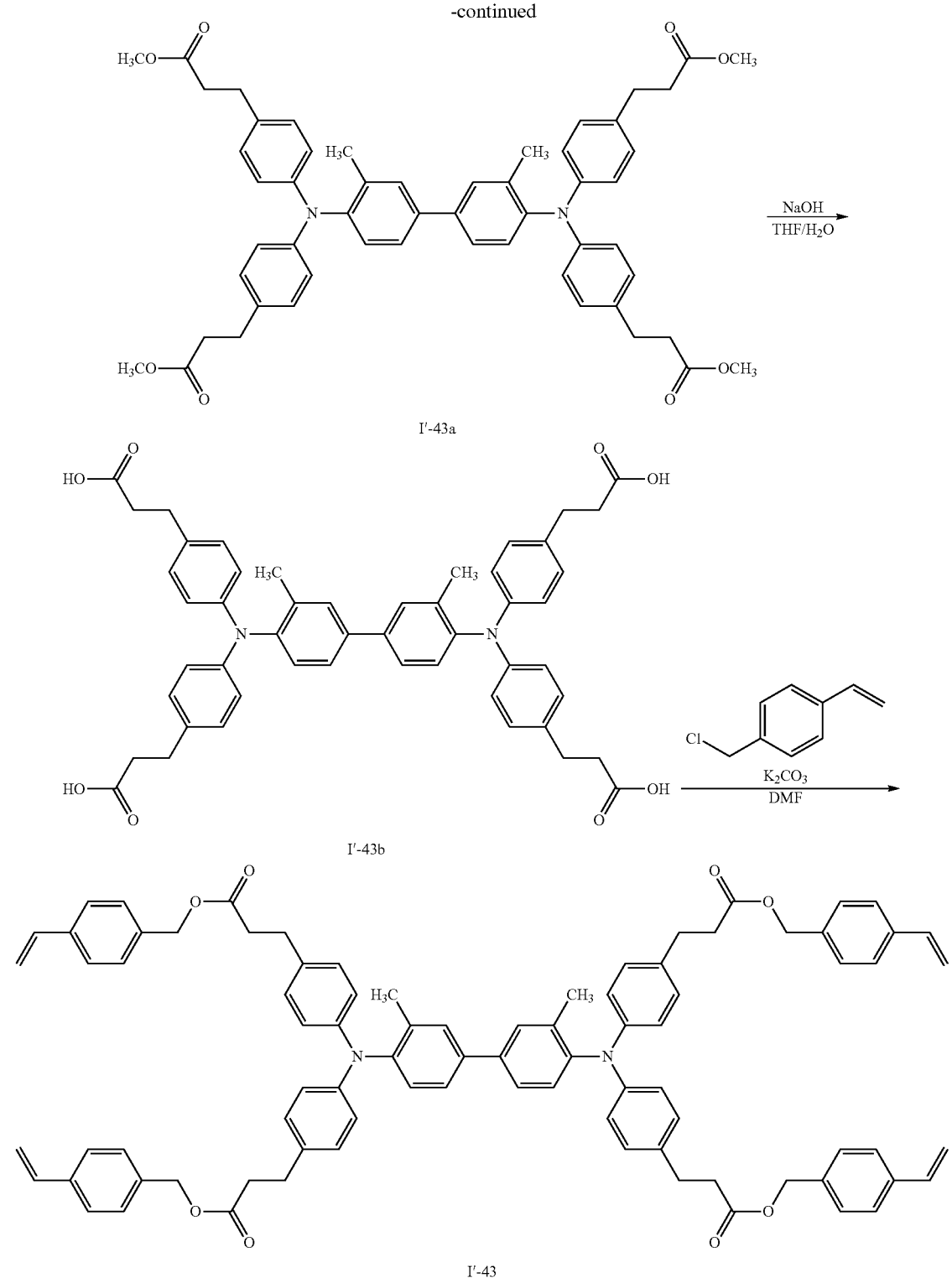

Example 2-1

(Preparation of Electrophotographic Photoreceptor)
—Preparation of Undercoat Layer 4—

100 parts by weight of zinc oxide (average particle size of 70 nm: manufactured by TAYCA: specific surface area of 15 m²/g) is mixed with 500 parts by weight of toluene under stirring, and 1.3 part by weight of a silane coupling agent (KEB503: manufactured by Shin-Etsu Chemical Co., Ltd.) is added thereto, followed by stirring for 2 hours. Thereafter, toluene is distilled away through distillation under reduced pressure, and the resultant is baked at 120° C. for 3 hours, thereby obtaining zinc oxide surface-treated with the silane coupling agent. 110 parts by weight of the surface-treated zinc oxide is mixed with 500 parts by weight of tetrahydrofuran under stirring, and a solution obtained by dissolving 0.6 parts by weight of alizarin in 50 parts by weight of tetrahydrofuran is added thereto, followed by stirring at 50° C. for 5 hours. Thereafter, the alizarin-imparted zinc oxide is filtered by filtration under reduced pressure, followed by drying at 60° C. under reduced pressure, thereby obtaining alizarin-imparted zinc oxide.

38 parts by weight of a solution obtained by mixing 60 parts by weight of the alizarin-imparted zinc oxide, 13.5 parts by weight of a curing agent (blocked isocyanate Sumidur BL 3175, manufactured by Sumika Bayer Urethane Co., Ltd.), and 15 parts by weight of a butyral resin (S-LEC BM-1, manufactured by Sekisui Chemical Co., Ltd.) with 85 parts by weight of methyl ethyl ketone is mixed with 25 parts by weight of methyl ethyl ketone, and the resultant is dispersed with a sand mill for 2 hours by using glass beads having a diameter of 1 mmφ, thereby obtaining a dispersion.

To the obtained dispersion, 0.005 parts by weight of dioctyltin dilaurate and 40 parts by weight of silicone resin particles (Tospearl 145, manufactured by GE Toshiba Silicones, Co., Ltd.) are added as a catalyst, thereby obtaining a coating liquid for forming an undercoat layer. This coating liquid is coated onto an aluminum substrate by dip coating, followed by drying and curing at 170° C. for 40 minutes, thereby obtaining an undercoat layer having a thickness of 20 μm.

—Preparation of Charge Generating Layer 2A—

A mixture including 15 parts by weight of hydroxy gallium phthalocyanine (CGM-1) as a charge generating material in which the Bragg angle (2θ±0.2°) of an X-ray diffraction spectrum using X-rays having Cukα characteristics has diffraction peaks at positions of at least 7.3°, 16.0°, 24.9°, and 28.0°, 10 parts by weight of a vinyl chloride-vinyl acetate copolymer resin (VMCH, manufactured by Nippon Unicar Co., Ltd.) as a binder resin, and 200 parts by weight of n-butyl acetate is dispersed with a sand mill for 4 hours by using glass beads having a diameter of 1 mmφ. To the obtained dispersion, 175 parts by weight of n-butyl acetate and 180 parts by weight of methyl ethyl ketone are added, followed by stirring, thereby obtaining a coating liquid for forming a charge generating layer. This coating liquid for forming a charge generating layer is coated onto the undercoat layer by dip-coating, followed by drying at room temperature (25° C.), thereby forming a charge generating layer having a film thickness of 0.2 μm.

—Preparation of Charge Transporting Layer 2B-1—

A coating liquid for forming the charge transporting layer 2B-1 having the following composition is prepared.

(Charge Transport Agent)

N,N'-diphenyl-N,N'-bis(3-methylphenyl)-[1,1']biphenyl-4,4'-diamine (CTM-1): 45 parts by weight (Resin)

Bisphenol Z polycarbonate resin (written as "PCZ 500" hereinafter, viscosity average molecular weight: 50000): 55 parts by weight (Solvent)

Chlorobenzene: 800 parts by weight

This coating liquid is coated onto the charge generating layer, followed by drying at 130° C. for 45 minutes, thereby obtaining the charge transporting layer 2B-1 having a film thickness of 20 μm.

—Preparation of Charge Transporting Layer 2B-2—

A coating liquid for forming the charge transporting layer 2B-2 having the following composition is prepared.

(Charge Transport Agent)

Charge transport material ((I')-15) synthesized in the Synthesis Example 2-1: 100 parts by weight (Initiator)

V-601 (manufactured by Wako Pure Chemical Industries, Ltd.): 2 parts by weight (Solvent)

Mixed solvent of tetrahydrofuran (THF)/toluene (weight ratio of 60/40): 150 parts by weight This coating liquid is coated onto the charge transporting layer 2B-1, followed by heating at 150° C. for minutes in an atmosphere in which an oxygen concentration is about 100 ppm, thereby forming a 7 μm protective layer.

In the manner described above, an electrophotographic photoreceptor is obtained, and this photoreceptor is taken as a photoreceptor 2-1.

Examples 2-2 to 2-22 and Comparative Examples 2-1 and 2-2

(Preparation of Electrophotographic Photoreceptor)

Electrophotographic photoreceptors are obtained in the same manner as that in Example 2-1, except that the charge transport material in the coating liquid for forming the charge transporting layer 2B-2 in Example 2-1 is changed as shown in Table 8. These photoreceptors are taken as photoreceptors 2-2 to 2-22 and comparative photoreceptors 2-1 and 2-2.

[Photoreceptor Running Evaluation 1]

Figure 16:
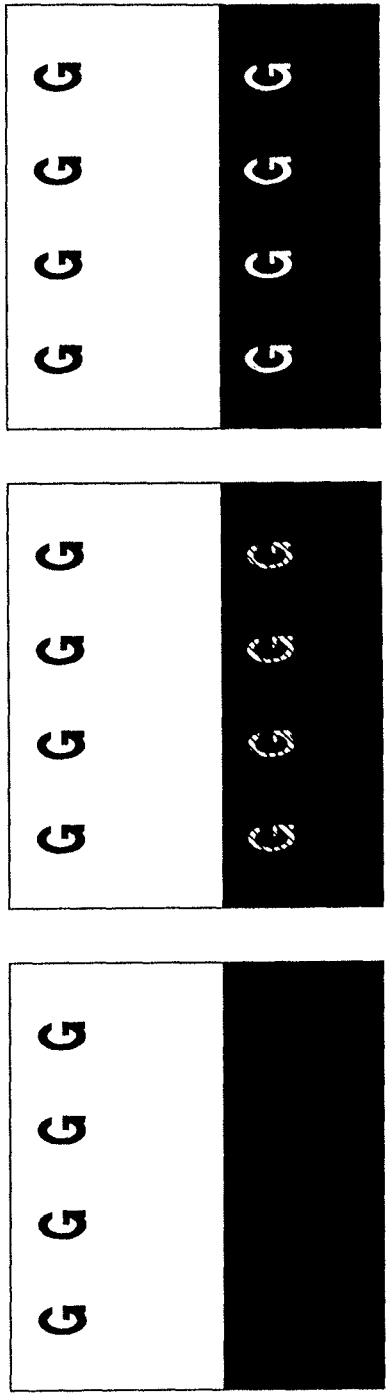
FIGS. 16A to 16C are views showing image patterns used respectively for an image evaluation.

The electrophotographic photoreceptors prepared in the Examples 2-1 to 2-22 and Comparative Examples 2-1 and 2-2 are mounted on a DocuCentre Color 400CP (manufactured by Fuji Xerox Co., Ltd.), and the pattern for image evaluation shown in FIG. 16A is output in normal environment (20° C., 50% RH). Thereafter, 30000 sheets of black solid pattern are consecutively output, and then the pattern for image evaluation is output again. In addition, the amount of light is adjusted according to the sensitivity of the charge generating material by using a filter.

<Image Stability>

The patterns for image evaluation output before and after the running evaluation 1 are compared with each other. The degree of image deterioration is visually observed and evaluated in the following manner. A++ indicates the best characteristic.

A++: best (deterioration is almost not observed in entire output image pattern)

A+: in a portion of plural output image patterns, enlarged images show change.

A: fair (change is not visually confirmed, but enlarged images show change)

B: though image quality deterioration is confirmed, this is an allowable level.

C: image quality deterioration is confirmed, and this is a problematic level.

<Electrical Characteristic Stability>

Before and after the photoreceptor running evaluation 1, the respective photoreceptors are charged negatively by a scorotron charging device having a grid applied voltage −700 V in normal environment (20° C., 50% RH). Thereafter, the charged photoreceptors are subjected to flash exposure by using a 780 nm semiconductor laser with a light amount of 10 mJ/m². After the exposure, a potential (V) of the photoreceptor surface after 10 seconds is measured, and the value is taken as the value of a residual potential. All of the photoreceptors show negative residual potential value. Regarding the respective photoreceptors, a value of (residual potential before running evaluation 1)−(residual potential after running evaluation 1) is calculated, thereby evaluating the electrical characteristic stability. A++ indicates the best characteristic.

A++: less than 10 V

A+: 10 V or more and less than 20 V

A: 20 V or more and less than 30 V

B: 30 V or more and less than 50 V

C: 50 V or more

<Mechanical Strength>

The degree of scratches caused on the photoreceptor surface after the photoreceptor evaluation 1 is judged by visual observation. A+ indicates the best characteristic.

A+: scratches are not confirmed even in microscopic observation.

A: though not confirmed visually, small scratches are confirmed in microscopic observation.

B: scratches are partially caused.

C: scratches are caused in the entire photoreceptor surface.

[Photoreceptor Running Evaluation 2]

The electrophotographic photoreceptors prepared in the Examples 2-1 to 2-22 and Comparative Examples 2-1 and 2-2 are mounted on a DocuCentre Color 400CP (manufactured by Fuji Xerox Co., Ltd.). First, the pattern for image evaluation shown in FIG. 16A is output at a low temperature and low humidity (20° C., 30% RH) and taken as an [evaluation image 1]. Subsequently, 10000 sheets of black solid patterns are consecutively output, and then the pattern for image evaluation is output and taken as an [evaluation image 2]. The photoreceptor is left as it is for 24 hours in a low temperature and low humidity (20° C., 30% RH) environment, and then the pattern for image evaluation is output and taken as an [evaluation image 3]. Thereafter, 5000 sheets of black solid patterns are output in a high temperature and high humidity (28° C., 60% RH) environment, and then the pattern for image evaluation is output and taken as an [evaluation image 4]. The photoreceptor is left as it is for 24 hours in a high temperature and high humidity (28° C., 60% RH) environment, and then the pattern for image evaluation is output and taken as an [evaluation image 5]. The photoreceptor is returned to a low temperature and low humidity (20° C., 30% RH) environment, 20000 sheets of black solid patterns are output again, and the pattern for image evaluation is output and taken as an [evaluation image 6].

<Ghost Evaluation>

The [evaluation image 3] and [evaluation image 5] are compared with the [evaluation image 2] and [evaluation image 4] respectively, and the degree of image quality deterioration is evaluated by visual observation. A++ indicates the best characteristic.

A+: as excellent as FIG. 16A

A: though image quality is as excellent as FIG. 16A, ghost occurs slightly.

B: ghost is slightly noticeable as FIG. 16B.

C: ghost is clearly confirmed as FIG. 16C.

TABLE 8

| | Charge transporting layer 2B-2 Charge transport material (A) of exemplary embodiment of the invention | Evaluation result | | | |
|---|---|---|---|---|---|
| | | Image stability | Electrical characteristics | Mechanical strength | Ghost |
| Example 2-1 | I'-15 | A | A | A | A |
| Comparative Example 2-1 | AC-1 | B | B | B | A |
| Comparative Example 2-2 | AC-2 | C | C | B | C |
| Example 2-2 | I'-17 | A | A | A | A |
| Example 2-3 | I'-23 | A | A | A | A |
| Example 2-4 | I'-27 | A | A | A | A |
| Example 2-5 | I'-30 | A | A | A | A |
| Example 2-6 | I'-32 | A | A | A+ | A |
| Example 2-7 | I'-34 | A+ | A | A+ | A |
| Example 2-8 | I'-36 | A | A+ | A | A |
| Example 2-9 | I'-43 | A++ | A+ | A+ | A+ |
| Example 2-10 | I'-46 | A++ | A+ | A | A+ |
| Example 2-11 | I'-53 | A++ | A+ | A+ | A+ |
| Example 2-12 | I'-48 | A++ | A+ | A+ | A+ |
| Example 2-13 | I'-40 | A++ | A+ | A+ | A+ |
| Example 2-14 | I'-58 | A | A+ | A+ | A |
| Example 2-15 | I'-122 | A+ | A+ | A | A+ |
| Example 2-16 | I'-123 | A+ | A | A+ | A |
| Example 2-17 | I'-124 | A | A | A | A |
| Example 2-18 | I'-125 | A | A | A | A |
| Example 2-19 | I'-126 | A | A | A | A |
| Example 2-20 | I'-127 | A | A | A | A |
| Example 2-21 | I'-43/I'-121 (Weight ratio 95/5) | A++ | A+ | A+ | A+ |
| Example 2-22 | I-43/I-121 (Weight ratio 50/50) | A++ | A+ | A+ | A+ |

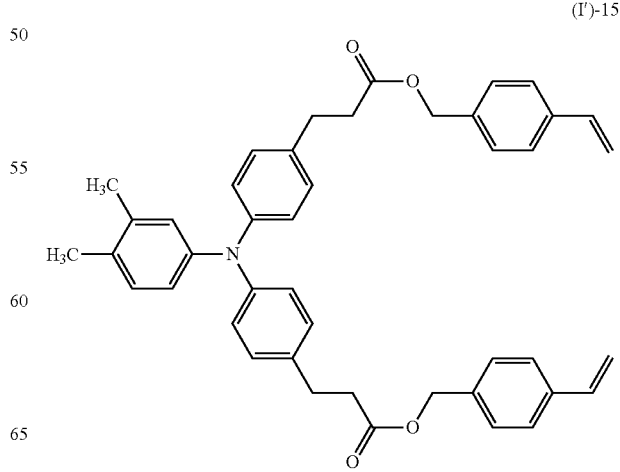

(I')-15

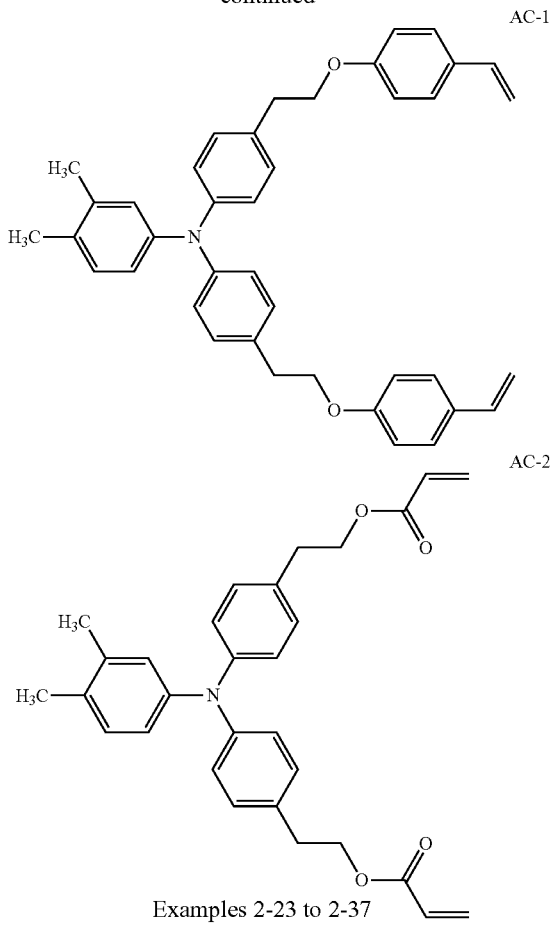

Examples 2-23 to 2-37

(Preparation of Electrophotographic Photoreceptor)

Electrophotographic photoreceptors are obtained in the same manner as that in Example 2-1, except that the charge generating material in charge generating layer 2A, the charge transport agent in charge transporting layer 2B-1, the respective components of the charge transporting layer 2B-2, and types of solvents in Example 2-1 are changed as shown in Table 9. These photoreceptors are taken as photoreceptors 2-23 to 2-37.

The photoreceptors 2-23 to 2-37 are evaluated in the same manner as that in Example 2-1, and the results are shown in Table 9. In addition, the compounds in the table are as follows.

CGM-2: titanyl phthalocyanine
CTM-2: the following compound

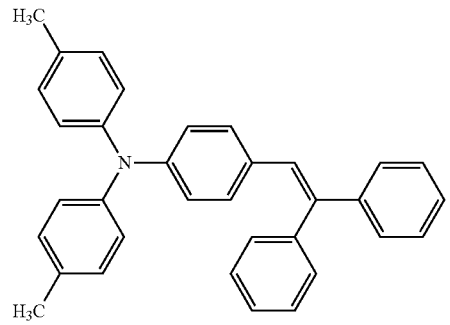 [SMILES: Cc1ccc(N(c2ccc(C)cc2)c2ccc(C=C(c3ccccc3)c3ccccc3)cc2)cc1]

CTM-3: the following compound

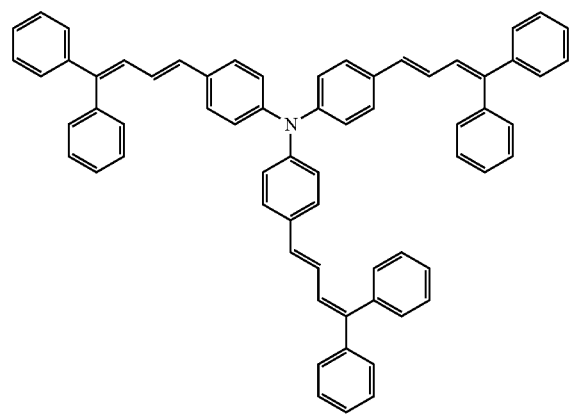 [SMILES: C(/C=C/c1ccc(N(c2ccc(/C=C/C=C(c3ccccc3)c3ccccc3)cc2)c2ccc(/C=C/C=C(c3ccccc3)c3ccccc3)cc2)cc1)=C(c1ccccc1)c1ccccc1]

Monomer-1: A-DCP (bifunctional acrylate monomer manufactured by Shin-Nakamura Chemicals Co., Ltd.)
Monomer-2: A-DPH (hexafunctional acrylate monomer manufactured by Shin-Nakamura Chemicals Co., Ltd.)
Monomer-3: BPE-200 (bifunctional methacrylate monomer manufactured by Shin-Nakamura Chemicals Co., Ltd.)
(Initiator)
V-40: initiator manufactured by Wako Pure Chemical Industries, Ltd. (thermal radical generator)
VE-073: initiator manufactured by Wako Pure Chemical Industries, Ltd. (thermal radical generator)
OTazo-15: initiator manufactured by Otsuka Chemical Co., Ltd. (thermal radical generator)
Perhexyl O: initiator manufactured by Nof Corporation (thermal radical generator)
(Resin)
S-LEC B BX-L: polyvinyl butyral resin manufactured by Sekisui Chemical Co., Ltd.

TABLE 9

| | Charge generating layer 2A Charge generating material | Charge transporting layer 2B-1 Charge transport material Weight ratio in ( ) | Charge transporting layer 2B-2 | | | |
|---|---|---|---|---|---|---|
| | | | Charge transport material (A) of exemplary embodiment of the invention | Initiator | Charge transport material other than (A) | Radical-polymerizable monomer not having charge transport function |
| Example 2-23 | CGM-1 | CTM-1 | I'-27 | VE-073 | None | None |
| Example 2-24 | CGM-1 | CTM-1 | I'-53 | V-40 | None | None |
| Example 2-25 | CGM-1 | CTM-1 | I'-43 | OTazo-15 | None | None |
| Example 2-26 | CGM-1 | CTM-1 | I'-40 | Perhexyl O | None | None |
| Example 2-27 | CGM-1 | CTM-1 | I'-15 | V-601 | None | None |

TABLE 9-continued

| | | | | | | |
|---|---|---|---|---|---|---|
| Example 2-27 | CGM-1 | CTM-1 | I'-53 | V-601 | None | None |
| Example 2-28 | CGM-1 | CTM-1 | I'-43 | V-601 | None | None |
| Example 2-29 | CGM-1 | CTM-1 | I'-53 | V-601 | None | None |
| Example 2-30 | CGM-1 | CTM-1 | I'-23 | V-601 | CTM-2 (15 parts by weight) | None |
| Example 2-31 | CGM-1 | CTM-1 | I'-46 | V-601 | CTM-3 (20 parts by weight) | None |
| Example 2-32 | CGM-1 | CTM-1 | I'-15 | V-601 | None | Monomer-1 (10 parts by weight) |
| Example 2-33 | CGM-1 | CTM-1 | I'-30 | V-601 | None | Monomer-2 (5 parts by weight) |
| Example 2-34 | CGM-1 | CTM-1 | I'-53 | V-601 | None | Monomer-3 (10 parts by weight) |
| Example 2-35 | CGM-1 | CTM-2 | I'-15 | V-601 | None | None |
| Example 2-36 | CGM-1 | CTM-1/CTM-3 (70/30) | I'-43 | V-601 | None | None |
| Example 2-37 | CGM-2 | CTM-1 | I'-53 | V-601 | None | None |

| | Charge transporting layer 2B-2 | | Evaluation result | | | |
|---|---|---|---|---|---|---|
| | Resin | Coating solvent Weight ratio in ( ) | Image stability | Electrical characteristic | Mechanical strength | Ghost |
| Example 2-23 | None | THF/toluene (60/40) | A | A | A | A |
| Example 2-24 | None | THF/toluene (60/40) | A++ | A+ | A+ | A+ |
| Example 2-25 | None | THF/toluene (60/40) | A++ | A+ | A+ | A+ |
| Example 2-26 | None | THF/toluene (60/40) | A++ | A+ | A+ | A+ |
| Example 2-27 | PCZ500 | THF/toluene (60/40) | A | A | A | A |
| Example 2-27 | BX-L | THF/toluene (60/40) | A++ | A+ | A+ | A+ |
| Example 2-28 | None | n-butyl acetate | A++ | A+ | A+ | A+ |
| xample 2-29 | None | Methyl i-butyl ketone | A++ | A+ | A+ | A+ |
| Example 2-30 | None | THF/toluene (60/40) | A | A | A | A |
| Example 2-31 | None | THF/toluene (60/40) | A++ | A+ | A | A+ |
| Example 2-32 | None | THF/toluene (60/40) | A | A | A | A |
| Example 2-33 | None | THF/toluene (60/40) | A | A | A | A |
| Example 2-34 | None | THF/toluene (60/40) | A++ | A+ | A+ | A+ |
| Example 2-35 | None | THF/toluene (60/40) | A | A | A | A |
| Example 2-36 | None | THF/toluene (60/40) | A++ | A+ | A+ | A+ |
| Example 2-37 | None | THF/toluene (60/40) | A++ | A+ | A+ | A+ |

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An electrophotographic photoreceptor comprising:
   a conductive substrate; and
   a photosensitive layer provided on the conductive substrate,
   wherein an uppermost surface layer thereof is a layer including a polymerized or cured film of a composition that contains one or more kinds of charge transport materials (A2) represented by the following General Formula (I'):

wherein in General Formula (I'), F represents a charge transporting skeleton, D represents a group represented by the following General Formula (IV), and m represents an integer of from 1 to 8:

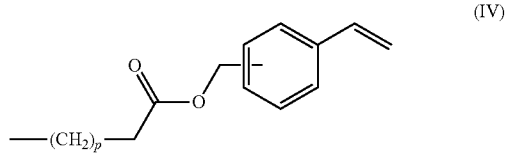

wherein in General Formula (IV), p represents an integer of from 2 to 4.

2. The electrophotographic photoreceptor according to claim 1,
wherein the charge transport material (A2) represented by General Formula (I') is a charge transport material represented by the following General Formula (II'):

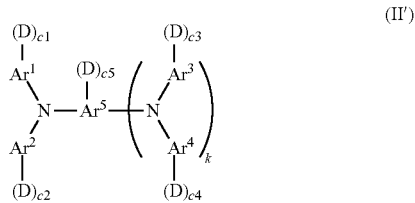

wherein in General Formula (II'), each of $Ar^1$ to $Ar^4$ independently represents a substituted or unsubstituted aryl group, $Ar^5$ represents a substituted or unsubstituted aryl group or a substituted or unsubstituted arylene group, D has the same definition as that of D in General Formula (I'), each of c1 to c5 represents an integer of from 0 to 2, and the sum of c1 to c5 is an integer of from 1 to 8, and k is 0 or 1.

3. The electrophotographic photoreceptor according to claim 1, wherein m in General Formula (I') is an integer of from 2 to 6.

4. The electrophotographic photoreceptor according to claim 3, wherein m in General Formula (I') is an integer of from 3 to 6.

5. The electrophotographic photoreceptor according to claim 4,
wherein m in General Formula (I') is an integer of from 4 to 6.

6. The electrophotographic photoreceptor according to claim 1,
wherein the uppermost surface layer is a layer including a film that is formed by polymerizing or curing the composition containing the charge transport material (A2) by using heat, light, or electron beams.

7. A process cartridge comprising at least the electrophotographic photoreceptor according to claim 1, and being detachable from an image forming apparatus.

8. An image forming apparatus comprising:
electrophotographic photoreceptor according to claim 1;
a charging device that charges the electrophotographic photoreceptor;
a latent image forming device that forms an electrostatic latent image on the surface of the charged electrophotographic photoreceptor;
a developing device that develops the electrostatic latent image formed on the surface of the electrophotographic photoreceptor by using a developer including a toner to form a toner image; and
a transfer device that transfers the toner image formed on the surface of the electrophotographic photoreceptor to a recording medium.

9. A method of producing an electrophotographic photoreceptor according to claim 1 comprising:
forming a coating film by coating a surface to be coated with a coating liquid including a composition that contains the one or more charge transport material (A2) represented by General Formula (I'); and
forming an uppermost surface layer through polymerizing or curing of the coating film by heating the coating film in a condition of from 100° C. to 170° C.

* * * * *